(12) United States Patent
Haurand et al.

(10) Patent No.: US 8,008,304 B2
(45) Date of Patent: *Aug. 30, 2011

(54) SUBSTITUTED PROPIOLIC ACID AMIDES AND THEIR USE FOR PRODUCING DRUGS

(75) Inventors: Michael Haurand, Aachen (DE); Klaus Schiene, Juchen (DE); Sven Kühnert, Düren (DE); Melanie Reich, Aachen (DE); Saskia Zemolka, Aachen (DE)

(73) Assignee: Grüenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/147,003

(22) Filed: Jun. 26, 2008

(65) Prior Publication Data

US 2008/0261996 A1    Oct. 23, 2008

Related U.S. Application Data

(63) Continuation of application No. PCT/EP2006/012481, filed on Dec. 22, 2006.

(30) Foreign Application Priority Data

Dec. 28, 2005    (DE) .................... 10 2005 062 986

(51) Int. Cl.
*A61K 31/50*       (2006.01)
*A61K 31/501*      (2006.01)
*C07D 403/00*      (2006.01)

(52) U.S. Cl. .................. 514/252.13; 544/359
(58) Field of Classification Search .............. None
See application file for complete search history.

(56) References Cited

U.S. PATENT DOCUMENTS

| 7,067,507 | B2 * | 6/2006 | Pulley et al. .................. 514/183 |
| 2004/0006091 | A1 | 1/2004 | Kyle et al. |
| 2008/0269295 | A1 * | 10/2008 | Haurand et al. .............. 514/326 |
| 2009/0176756 | A1 * | 7/2009 | Haurand et al. .......... 514/210.18 |

FOREIGN PATENT DOCUMENTS

| WO | 03 093236 | 11/2003 |
| WO | 2004 014903 | 2/2004 |
| WO | 2004 029044 | 4/2004 |
| WO | 2005 016323 | 2/2005 |
| WO | 2005 035500 | 4/2005 |
| WO | 2006 002981 | 1/2006 |

OTHER PUBLICATIONS

Vippagunta et al. Advanced Drug Delivery Reviews, 2001, 48, 3-26.*
Bach et al. Expert Opinion on Therapeutic Patents, 2007, 17(4), 371-84.*
Jaescke et al. Expert Opinion on Therapeutic Patents, 2008, 18(2), 123-142.*
Constantino et al. Expert Opinion on Therapeutic Targets, 2001, 5(6), 669-83.*
Litten et al. Expert Opinion on Emerging Drugs, 2005, 10(2), pp. 323-343.*
"Pruritus (itching)", http://www.webmd.com/skin-problems-and-treatments/guide/skin-conditions-pruritus, accessed Mar. 31, 2010.*
"Schizophrenia-Prevention", http://www.webmd.com/schizophrenia/tc/schizophrenia-prevention, accessed Dec. 12, 2008.*
"Patient Care—Education—SCI healthy", http://rehab.washington.edu/patientcare/patientinfo/articles/sci_healthy.asp, accessed May 26, 2009.*
Markou. Neuropsychopharmacology, 2009, 34, 817-819.*
Bao et al. Brain Research, 2001, 922, 173-179.*
Mach et al. ChemBioChem, 2004, 5, 508-518.*
Greene, et al; Protective Groups in Organic synthesis; Third Edition, 1999.
Kocienski, Protecting Groups; Third Edition, 2005 Georg Thieme Verlag.
Gennaro edition; Remmington's Pharmaceutical Sciences, 17th Edition, Mack Publishing Company, Easton, PA 1985, in particular in part 8, chapters 76 to 93.

* cited by examiner

*Primary Examiner* — Noble Jarrell
(74) *Attorney, Agent, or Firm* — Norris McLaughlin & Marcus, P.A.

(57) ABSTRACT

The present invention relates to substituted propiolic acid amides, methods for the production thereof, medicaments containing these compounds and the use thereof for producing medicaments.

31 Claims, No Drawings

SUBSTITUTED PROPIOLIC ACID AMIDES AND THEIR USE FOR PRODUCING DRUGS

This application is a continuation of PCT/EP2006/012481, filed on Dec. 22, 2006, which, in turn, claims priority of German Patent Application No. DE 10 2005 062 986.5, filed on Dec. 28, 2005.

The present invention relates to substituted propiolic acid amides, methods for their production, medicaments containing these compounds and their use for producing medicaments.

Pain is one of the basic symptoms in clinics. There is a worldwide need for effective pain treatments. The urgency of the requirement for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

Traditional opioids, such as morphine, are effective in the treatment of severe to very severe pain, but often lead to undesired side effects such as respiratory depression, vomiting, sedation, constipation or development of tolerance. Moreover, they are often not sufficiently effective in the case of neuropathic pain, from which tumour patients in particular often suffer.

One object of the present invention was therefore to provide new compounds which are particularly suitable as active pharmaceutical substances in medicaments, preferably in medicaments for the treatment of pain.

It was surprisingly found that the substituted propiolic acid amides of the general formula I indicated below are suitable for mGluR5 receptor regulation and can therefore be used in particular as active pharmaceutical substances in medicaments for the prevention and/or treatment of disorders or illnesses connected to these receptors or processes.

One subject matter of the present invention is therefore substituted propiolic acid amides of the general formula I,

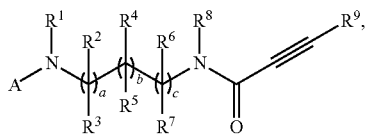

in which
a, b and c, mutually independently, in each case denote 0 or 1, whereby the sum of a, b and c is equal to 1, 2 or 3;
A denotes one of the following residues

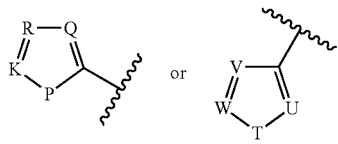

Q and U respectively denote $CR^{10}$ or N;
R and V respectively denote $CR^{11}$ or N;
K and W respectively denote $CR^{12}$ or N;
P and T respectively denote O, S or $NR^{13}$;
with the proviso that compounds are excluded in which P denotes S, Q denotes N, R denotes $CR^{11}$ and K denotes $CR^{12}$ or N;

$R^1$ and $R^8$, mutually independently, in each case denote H; —C(═O)—$R^{28}$; —C(═O)—O—$R^{29}$; —C(═O)—$NH_2$; —C(═O)—NH—$R^{30}$; —C(═O)—$NR^{31}R^{32}$; —S(═O)—$R^{33}$; —S(═O)$_2$—$R^{34}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

$R^2$, $R^3$, $R^4$, $R^5$, $R^6$, $R^7$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$, mutually independently, in each case denote H; F; Cl; Br; I; —$NO_2$; —CN; —$NH_2$; —OH; —SH; —C(═O)—OH; —C(═O)—H; —NH—C(═O)—H; —C(═O)—$R^{28}$; —C(═O)—O—$R^{29}$; —C(═O)—$NH_2$; —C(═O)—NH—$R^{30}$; —C(═O)—$NR^{31}R^{32}$; —S(═O)—$R^{33}$; —S(═O)$_2$—$R^{34}$; —NH—$R^{35}$; —$NR^{36}R^{37}$; —O—C(═O)—$R^{38}$; —NH—C(═O)—$R^{39}$; —$NR^{40}$—C(═O)—$R^{41}$; —O—$R^{42}$; —S—$R^{43}$; —NH—C(═O)—NH—$R^{44}$; —NH—C(═S)—NH—$R^{45}$; —NH—S(═O)$_2$—$R^{46}$; —$NR^{47}$—S(═O)$_2$—$R^{48}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

or $R^2$ and $R^3$ or $R^4$ and $R^5$ or $R^6$ and $R^7$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$, mutually independently, jointly denote a residue selected from the group comprising an oxo group (=O) and a thioxo group (=S);

or $R^1$ and $R^8$ together with the —N—$CR^2R^3$—$(CR^4R^5)_b$—$(CR^6R^7)_c$ group joining them together form a residue of the general formula B,

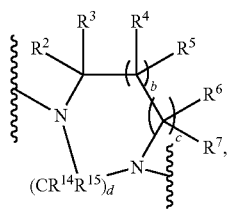

B whereby d denotes 1, 2 or 3 and b denotes 0 or 1 and c denotes 0 or 1;

or $R^1$ and R2 together with the —N—$CR^3$ group joining them together form a residue of the general formula C,

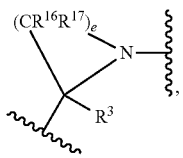

C whereby e denotes 1, 2, 3 or 4 and, in this case, b denotes 0 or 1 and c denotes 0;

or $R^1$ and $R^4$ together with the —N—$CR^2R^3$—$CR^5$ group joining them together form a residue of the general formula D,

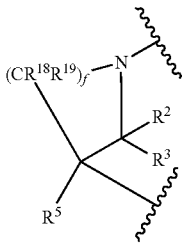

D whereby f denotes 1, 2, 3 or 4, and, in this case, c denotes 0;

or $R^1$ and $R^6$ together with the —N—$CR^2R^3$—$CR^4R^5$—$CR^7$ group joining them together form a residue of the general formula E,

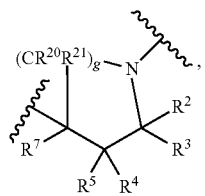

E whereby g denotes 1, 2 or 3;

or $R^6$ and $R^8$ together with the —N—$CR^7$ group joining them together form a residue of the general formula F

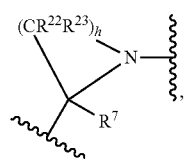

F whereby h denotes 1, 2, 3 or 4 and, in this case, b denotes 0 or 1 and a denotes 0;

or $R^4$ and $R^8$ together with the —N—$CR^6R^7$—$CR^5$ group joining them together form a residue of the general formula G,

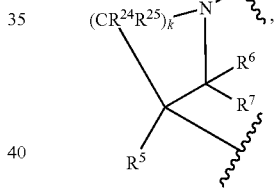

G whereby k denotes 1, 2, 3 or 4, and, in this case, a denotes 0;

or $R^2$ and $R^8$ together with the —N—$CR^6R^7$—$CR^4R^5$—$CR^3$ group joining them together form a residue of the general formula H,

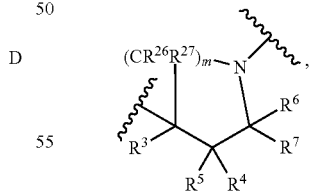

H whereby m denotes 1, 2 or 3;

$R^9$ denotes unsubstituted or substituted aryl or unsubstituted or substituted heteroaryl;

$R^{10}$, $R^{11}$ and $R^{12}$, mutually independently, in each case denote H; F; Cl; Br; I; —$NO_2$; —CN; —$NH_2$; —OH; —SH; —C(=O)—OH; —C(=O)—H; —NH—C(=O)—H; —C(=O)—$R^{28}$; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; —NH—$R^{35}$;

—NR$^{36}$R$^{37}$; —O—C(=O)—R$^{38}$; —NH—C(=O)—R$^{39}$; —NR$^{40}$—C(=O)—R$^{41}$; —O—R$^{42}$; —S—R$^{43}$; —NH—C(=O)—NH—R$^{44}$; —NH—C(=S)—NH—R$^{45}$; —NH—S(=O)$_2$—R$^{46}$; —NR$^{47}$—S(=O)$_2$—R$^{48}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

R$^{13}$ denotes H; —C(=O)—OH; —C(=O)—H; —C(=O)—R$^{28}$; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

and R$^{28}$, R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$ and R$^{48}$, mutually independently, in each case denote unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

The term "alkyl" encompasses, within the meaning of the present invention, acyclic saturated hydrocarbon residues which can be branched or straight-chained and unsubstituted or at least monosubstituted with, as in the case of $C_{1-12}$-alkyl, 1 to 12 (i.e. 1, 2, 3, 4, 5, 6, 7, 8, 9, 10, 11 or 12) C-atoms or with, as in the case of $C_{1-6}$-alkyl, 1 to 6 (i.e. 1, 2, 3, 4, 5 or 6) C-atoms. Provided that one or more of the substituents denote an alkyl residue or have an alkyl residue, which is monosubstituted or multiply substituted, this can preferably be substituted with optionally 1, 2, 3, 4 or 5, particularly preferably with 1, 2 or 3 substituents mutually independently selected from the group comprising F, Cl, Br, I, —NO$_2$, —CN, —OH, —SH, —NH$_2$, —N($C_{1-5}$-alkyl)$_2$, —N($C_{1-5}$-alkyl)(phenyl), —N($C_{1-5}$-alkyl)(CH$_2$-phenyl), —N($C_{1-5}$-alkyl)(CH$_2$—CH$_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—NH$_2$, —C(=O)—NH—$C_{1-5}$-alkyl, —C(=O)—N($C_{1-5}$-alkyl)$_2$, —S(=O)—$C_{1-5}$-alkyl, —S(=O)-phenyl, —S(=O)$_2$—$C_{1-5}$-alkyl, —S(=O)$_2$-phenyl, —S(=O)$_2$—NH$_2$ and —SO$_3$H, whereby the above-mentioned $C_{1-5}$-alkyl residues can in each case be linear or branched and the above-mentioned phenyl residues can be substituted preferably with 1, 2, 3, 4 or 5 substituents mutually independently selected from the group comprising F, Cl, Br, I, —CN, —CF$_3$, —OH, —NH$_2$, —O—CF$_3$, —SH, —O—CH$_3$, —O—$C_2$H$_5$, —O—$C_3$H$_7$, methyl, ethyl, n-propyl, isopropyl, n-butyl, 2-butyl, isobutyl and tert-butyl. Particularly preferred substituents can be mutually independently selected from the group comprising F, Cl, Br, I, —NO$_2$, —CN, —OH, —SH, —NH$_2$, —N(CH$_3$)$_2$, —N($C_2$H$_5$)$_2$ and —N(CH$_3$)($C_2$H$_5$).

By way of example, methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, 2-hexyl, 3-hexyl, n-heptyl, n-octyl, —C(H)(C$_2$H$_5$)$_2$, —C(H)(n-C$_3$H$_7$)$_2$ and —CH$_2$—CH$_2$—C(H)(CH$_3$)—(CH$_2$)$_3$—CH$_3$ are cited as suitable C$_{1-12}$-alkyl residues which can be unsubstituted or monosubstituted or multiply substituted. By way of example, methyl, ethyl, n-propyl, isopropyl, n-butyl, isobutyl, 2-butyl, tert-butyl, n-pentyl, 2-pentyl, 3-pentyl, iso-pentyl, neo-pentyl, n-hexyl, 2-hexyl and 3-hexyl are cited as suitable C$_{1-6}$-alkyl residues.

Multiply substituted alkyl residues refer to such alkyl residues which are multiply substituted, preferably twice or three times, either at various or at the same C-atoms, for example, three times at the same C-atom as in the case of —CF$_3$ or at various points as in the case of —(CHCl)—(CH$_2$F). The multiple substitution can be performed with the same or with different substituents. By way of example, —CF$_3$, —CF$_2$H, —CFH$_2$, —(CH$_2$)—OH, —(CH$_2$)—NH$_2$, —(CH$_2$)—CN, —(CH$_2$)—(CF$_3$), —(CH$_2$)—(CHF$_2$), —(CH$_2$)—(CH$_2$F), —(CH$_2$)—(CH$_2$)—OH, —(CH$_2$)—(CH$_2$)—NH$_2$, —(CH$_2$)—(CH$_2$)—CN, —(CF$_2$)—(CF$_3$), —(CH$_2$)—(CH$_2$)—(CF$_3$) and —(CH$_2$)—(CH$_2$)—(CH$_2$)—OH are cited as suitable substituted alkyl residues.

The term "alkenyl" encompasses, within the meaning of the present invention, acyclic unsaturated hydrocarbon residues which can be branched or straight-chained and unsubstituted or at least monosubstituted and have at least one double-bond, preferably 1, 2 or 3 double-bonds, with as in the case of C$_{2-12}$-alkenyl 2 to 12 (i.e. 2, 3, 4, 5, 6, 7, 8, 9, 10, 11 or 12) C-atoms or with as in the case of C$_{2-6}$-alkenyl 2 to 6 (i.e. 2, 3, 4, 5 or 6) C-atoms. Provided that one or more of the substituents denote an alkenyl residue or have an alkenyl residue which is monosubstituted or multiply substituted, this can preferably be substituted with optionally 1, 2, 3, 4 or 5, particularly preferably with 1, 2 or 3 substituents mutually independently selected from the group comprising F, Cl, Br, I, —NO$_2$, —CN, —OH, —SH, —NH$_2$, —N(C$_{1-5}$-alkyl)$_2$, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, whereby the above-mentioned C$_{1-5}$-alkyl residues can in each case be linear or branched and the above-mentioned phenyl residues can preferably be substituted with 1, 2, 3, 4 or 5 substituents mutually independently selected from the group comprising F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl. Particularly preferred substituents can be selected mutually independently from the group comprising F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$).

By way of example, ethenyl, 1-propenyl, 2-propenyl, 1-butenyl, 2-butenyl, 3-butenyl, 1-pentenyl, 2-pentenyl, 3-pentenyl, 4-pentenyl, hexenyl, —CH=CH—CH=CH—CH$_3$ and —CH$_2$—CH$_2$—CH=CH$_2$ are cited as suitable C$_{2-12}$-alkenyl residues.

Multiply substituted alkenyl residues refer to such alkenyl residues which are multiply substituted, preferably twice, at different or at the same C-atoms, for example, twice at the same C-atom as in the case of —CH=CCl$_2$ or at various points as in the case of —CCl=CH—(CH$_2$)—NH$_2$. The multiple substitution can be performed with the same or with different substituents. By way of example, —CH=CH—(CH$_2$)—OH, —CH=CH—(CH$_2$)—NH$_2$ and —CH=CH—CN are cited as suitable substituted alkenyl residues.

The term "alkynyl" encompasses, within the meaning of the present invention, acyclic unsaturated hydrocarbon residues which can be branched or straight-chained and unsubstituted or at least monosubstituted and have at least one triple-bond, preferably 1 or 2 triple-bonds, with as in the case of C$_{2-12}$-alkynyl 2 to 12 (i.e. 2, 3, 4, 5, 6, 7, 8, 9, 10, 11 or 12) C-atoms or with as in the case of C$_{2-6}$-alkynyl 2 to 6 (i.e. 2, 3, 4, 5 or 6) C-atoms. Provided that one or more of the substituents denote an alkynyl residue or have an alkynyl residue which is monosubstituted or multiply substituted, this can preferably be substituted with optionally 1, 2, 3, 4 or 5, particularly preferably with optionally 1 or 2 substituents mutually independently selected from the group comprising F, Cl, Br, I, —NO$_2$, —CN, —OH, —SH, —NH$_2$, —N(C$_{1-5}$-alkyl)$_2$, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, whereby the above-mentioned C$_{1-5}$-alkyl residues can in each case be linear or branched and the above-mentioned phenyl residues can preferably be substituted with 1, 2, 3, 4 or 5 substituents mutually independently selected from the group comprising F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl. Particularly preferred substituents can be selected mutually independently from the group comprising F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$).

By way of example, ethynyl, 1-propynyl, 2-propynyl, 1-butynyl, 2-butynyl, 3-butynyl, 1-pentynyl, 2-pentynyl, 3-pentynyl, 4-pentynyl and hexynyl are cited as suitable C$_{2-12}$-alkynyl residues.

Multiply substituted alkynyl residues refer to those alkynyl residues which are either multiply substituted at different C-atoms, for example, twice at different C-atoms as in the case of —CHCl—C≡CCl. By way of example, —C≡C—F, —C≡C—Cl and —C≡C—I are cited as suitable substituted alkynyl residues.

The term "heteroalkyl" denotes an alkyl residue as described above in which one or more C-atoms have been replaced in each case by a heteroatom mutually independently selected from the group comprising oxygen, sulphur and nitrogen (NH). Heteroalkyl residues can preferably have 1, 2 or 3 heteroatom(s) mutually independently selected from the group comprising oxygen, sulphur and nitrogen (NH) as the chain member(s). Heteroalkyl residues can preferably be 2- to 12-membered, particularly preferably 2- to 6-membered.

By way of example, —CH$_2$—O—CH$_3$, —CH$_2$—O—C$_2$H$_5$, —CH$_2$—O—CH(CH$_3$)$_2$, —CH$_2$—O—C(CH$_3$)$_3$, —CH$_2$—S—CH$_3$, —CH$_2$—S—C$_2$H$_5$, —CH$_2$—S—CH(CH$_3$)$_2$, —CH$_2$—S—C(CH$_3$)$_3$, —CH$_2$—NH—CH$_3$, —CH$_2$—NH—C$_2$H$_5$, —CH$_2$—NH—CH(CH$_3$)$_2$, —CH$_2$—NH—C(CH$_3$)$_3$, —CH$_2$—CH$_2$—O—CH$_3$, —CH$_2$—CH$_2$—O—C$_2$H$_5$, —CH$_2$—CH$_2$—O—CH(CH$_3$)$_2$, —CH$_2$—CH$_2$—O—C(CH$_3$)$_3$, —CH$_2$—CH$_2$—S—CH$_3$, —CH$_2$—CH$_2$—S—C$_2$H$_5$, —CH$_2$—CH$_2$—S—CH(CH$_3$)$_2$, —CH$_2$—CH$_2$—S—C(CH$_3$)$_3$, —CH$_2$—CH$_2$—NH—CH$_3$, —CH$_2$—CH$_2$—NH—C$_2$H$_5$, —CH$_2$—CH$_2$—NH—CH(CH$_3$)$_2$, —CH$_2$—CH$_2$—NH—C(CH$_3$)$_3$, —CH$_2$—S—CH$_2$—O—CH$_3$, —CH$_2$—O—CH$_2$—O—C$_2$H$_5$, —CH$_2$—O—CH$_2$—O—CH(CH$_3$)$_2$, —CH$_2$—S—CH$_2$—O—C(CH$_3$)$_3$, —CH$_2$—O—CH$_2$—S—CH$_3$, —CH$_2$—O—CH$_2$—S—C$_2$H$_5$, —CH$_2$—O—CH$_2$—S—CH(CH$_3$)$_2$, —CH$_2$—NH—CH$_2$—S—C(CH$_3$)$_3$, —CH$_2$—O—CH$_2$—NH—CH$_3$, —CH$_2$—O—CH$_2$—NH—C$_2$H$_5$, —CH$_2$—O—CH$_2$—NH—CH(CH$_3$)$_2$, —CH$_2$—S—CH$_2$—NH—C(CH$_3$)$_3$ and —CH$_2$—CH$_2$—C(H)(CH$_3$)—(CH$_2$)$_3$—CH$_3$ are cited as suitable heteroalkyl residues which can be unsubstituted or monosubstituted or multiply substituted.

By way of example, —(CH$_2$)—O—(CF$_3$), —(CH$_2$)—O—(CHF$_2$), —(CH$_2$)—O—(CH$_2$F), —(CH$_2$)—S—(CF$_3$), —(CH$_2$)—S—(CHF$_2$), —(CH$_2$)—S—(CH$_2$F), —(CH$_2$)—(CH$_2$)—O—(CF$_3$), —(CF$_2$)—O—(CF$_3$), —(CH$_2$)—(CH$_2$)—S—(CF$_3$) and —(CH$_2$)—(CH$_2$)—(CH$_2$)—O—(CF$_3$) are cited as suitable substituted heteroalkyl residues.

The term "heteroalkenyl" denotes an alkenyl residue as described above in which one or more C-atoms have been replaced in each case by a heteroatom mutually independently selected from the group comprising oxygen, sulphur and nitrogen (NH). Heteroalkenyl residues can preferably have 1, 2 or 3 heteroatom(s) mutually independently selected from the group comprising oxygen, sulphur and nitrogen (NH) as the chain member(s). Heteroalkenyl residues can preferably be 2- to 12-membered, particularly preferably 2- to 6-membered.

By way of example, —CH$_2$—O—CH=CH$_2$, —CH=CH—O—CH=CH—CH$_3$, —CH$_2$—CH$_2$—O—CH=CH$_2$, —CH$_2$—S—CH=CH$_2$, —CH=CH—S—CH=CH—CH$_3$, —CH$_2$—CH$_2$—S—CH=CH$_2$, —CH$_2$—NH—CH=CH$_2$, —CH=CH—NH—CH=CH—CH$_3$ and —CH$_2$—CH$_2$—NH—CH=CH$_2$ are cited as suitable heteroalkenyl residues.

By way of example, —CH$_2$—O—CH=CH—(CH$_2$)—OH, —CH$_2$—S—CH=CH—(CH$_2$)—NH$_2$ and —CH$_2$—NH—CH=CH—CN are cited as suitable substituted heteroalkenyl residues.

The term "heteroalkynyl" denotes an alkynyl residue as described above in which one or more C-atoms have been replaced in each case by a heteroatom mutually independently selected from the group comprising oxygen, sulphur and nitrogen (NH). Heteroalkynyl residues can preferably have 1, 2 or 3 heteroatom(s) mutually independently selected from the group comprising oxygen, sulphur and nitrogen (NH) as the chain member(s). Heteroalkynyl residues can preferably be 2- to 12-membered, particularly preferably 2- to 6-membered.

By way of example, —CH$_2$—O—C≡CH, —CH$_2$—CH$_2$—O—C≡CH, —CH$_2$—O—C≡C—CH$_3$, —CH$_2$—CH$_2$—O—C≡C—CH$_3$, —CH$_2$—S—C≡CH, —CH$_2$—CH$_2$—S—C≡CH, —CH$_2$—S—C≡C—CH$_3$, —CH$_2$—CH$_2$—S—C≡C—CH$_3$ are cited as suitable heteroalkynyl residues.

By way of example, —CH$_2$—O—C≡C—Cl, —CH$_2$—CH$_2$—O—C≡C—I, —CHF—O—C≡C—CH$_3$, —CHF—CH$_2$—O—C≡C—CH$_3$, —CH$_2$—S—C≡C—Cl, —CH$_2$—CH$_2$—S—C≡C—Cl, —CHF—S—C≡C—CH$_3$, —CHF—CH$_2$—S—C≡C—CH$_3$ are cited as suitable substituted heteroalkynyl residues.

The term "cycloalkyl" means, in terms of the present invention, a cyclic saturated hydrocarbon residue with preferably 3, 4, 5, 6, 7, 8 or 9 C-atoms, particularly preferably with 3, 4, 5, 6 or 7 C-atoms, very particularly preferably with 5 or 6 C-atoms, whereby the residue can be unsubstituted or monosubstituted or multiply identically or differently substituted.

By way of example, cyclopropyl, cyclobutyl, cyclopentyl, cyclohexyl, cycloheptyl, cyclooctyl and cyclononyl are cited as suitable C$_{3-9}$-cycloalkyl residues which can be unsubstituted or monosubstituted or multiply substituted. Cyclopropyl, cyclobutyl, cyclopentyl, cyclohexyl and cycloheptyl are cited as suitable C$_{3-7}$-cycloalkyl residues.

The term "cycloalkenyl" means, in terms of the present invention, a cyclic unsaturated hydrocarbon residue with preferably 3, 4, 5, 6, 7, 8 or 9 C-atoms, particularly preferably with 3, 4, 5, 6 or 7 C-atoms, very particularly preferably with 5 or 6 C-atoms, which has at least one double-bond, preferably one double-bond, and can be unsubstituted or monosubstituted or multiply identically or differently substituted.

Cyclobutenyl, cyclopentenyl, cyclohexenyl, cycloheptenyl, cyclononenyl and cyclooctenyl are cited as suitable C$_{3-9}$-cycloalkenyl residues which can be unsubstituted or monosubstituted or multiply substituted. Cyclopentenyl and cyclohexenyl are cited as suitable C$_{5-6}$-cycloalkenyl residues.

The term "heterocycloalkyl" means, in terms of the present invention, a cyclic saturated hydrocarbon residue with preferably 3, 4, 5, 6, 7, 8 or 9 C-atoms, particularly preferably with 3, 4, 5, 6 or 7 C-atoms, very particularly preferably with 5 or 6 C-atoms, in which one or more C-atoms have been replaced in each case by a heteroatom mutually independently selected from the group comprising oxygen, sulphur and nitrogen (NH). Heterocycloalkyl residues can preferably have 1, 2 or 3 heteroatom(s) mutually independently selected from the group comprising oxygen, sulphur and nitrogen (NH) as the ring member(s). A heterocycloalkyl residue can be unsubstituted or monosubstituted or multiply identically or differently substituted. Heterocycloalkyl residues can preferably be 3- to 9-membered, particularly preferably 3- to 7-membered, very particularly preferably 5- to 7-membered.

By way of example, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1,3)-dioxolan-2-yl, isoxazolidinyl, isothioazolidinyl, pyrazolidinyl, oxazolidinyl, (1,2,4)-oxadiazolidinyl, (1,2,4)-thiadiazolidinyl, (1,2,4)-triazolidin-3-yl, (1,3,4)-thiadiazolidin-2-yl, (1,3,4)-triazolidin-1-yl, (1,3,4)-triazoldidin-2-yl, tetrahydropyridazinyl, tetrahydropyrimidinyl, tetrahydropyrazinyl, (1,3,5)-tetrahydrotriazinyl, (1,2,4)-tetrahydrotriazin-1-yl, (1,3)-dithian-2-yl and (1,3)-thiazolidinyl are cited as suitable 3- to 9-membered heterocycloalkyl residues which can be unsubstituted or monosubstituted or multiply substituted. By way of example, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, diazepanyl and (1,3)-dioxolan-2-yl are cited as suitable 5- to 7-membered heterocycloalkyl residues.

The term "heterocycloalkenyl" means, in terms of the present invention, a cyclic unsaturated hydrocarbon residue with preferably 4, 5, 6, 7, 8 or 9 C-atoms, particularly preferably with 4, 5, 6 or 7 C-atoms, very particularly preferably with 5 or 6 C-atoms, which has at least one double-bond, preferably one double-bond, and in which one or more C-atoms have been replaced in each case by a heteroatom mutually independently selected from the group comprising oxygen, sulphur and nitrogen (NH). Heterocycloalkenyl residues can preferably have 1, 2 or 3 heteroatom(s) mutually independently selected from the group comprising oxygen, sulphur and nitrogen (NH) as the ring member(s). A heterocycloalkenyl residue can be unsubstituted or monosubstituted or multiply identically or differently substituted. Heterocycloalkenyl residues can preferably be 4- to 9-membered, particularly preferably 4- to 7-membered, very particularly preferably 5- to 7-membered.

By way of example, (2,3)-dihydrofuranyl, (2,5)-dihydrofuranyl, (2,3)-dihydrothienyl, (2,5)-dihydrothienyl, (2,3)-dihydropyrrolyl, (2,5)-dihydropyrrolyl, (2,3)-dihydroisoxazolyl, (4,5)-dihydroisoxazolyl, (2,5)-dihydroisothiazolyl, (2,3)-dihydropyrazolyl, (4,5)-dihydropyrazolyl, (2,5)-dihydropyrazolyl, (2,3)-dihydrooxazolyl, (4,5)-dihydrooxazolyl, (2,5)-dihydrooxazolyl, (2,3)-dihydrothiazolyl, (4,5)-dihydrothiazolyl, (2,5)-dihydrothiazolyl, (2,3)-dihydroimidazolyl, (4,5)-dihydroimidazolyl, (2,5)-dihydroimidazolyl, (3,4,5,6)-tetrahydropyridin-2-yl, (1,2,5,6)-tetrahydropyridin-1-yl, (1,2)-dihydropyridin-1-yl, (1,4)-dihydropyridin-1-yl, dihydropyranyl and (1,2,3,4)-tetrahydropyridin-1-yl are cited as suitable heterocycloalkenyl residues or as suitable 5- to 7-membered heterocycloalkenyl residues which can be unsubstituted or monosubstituted or multiply substituted.

Cycloalkyl residue, heterocycloalkyl residue, cycloalkenyl residue or heterocycloalkenyl residue can, within the meaning of the present invention, be condensed (annelated) with an unsubstituted or at least monosubstituted mono- or bicyclic ring system. A mono- or bicyclic ring system refers, in the context of the present invention, to mono- or bicyclic hydrocarbon residues which can be saturated, unsaturated or aromatic and can optionally have one or more heteroatoms as ring members. The rings of the above-mentioned mono- or bicyclic ring systems are preferably respectively 4-, 5- or 6-membered and can have in each case preferably optionally 0, 1, 2, 3, 4 or 5 heteroatom(s), particularly preferably optionally 0, 1 or 2 heteroatom(s) as the ring member(s), which are mutually independently selected from the group comprising oxygen, nitrogen and sulphur. Provided that one bicyclic ring system is present, the different rings can, in each case mutually independently, have a different degree of saturation, i.e. be saturated, unsaturated or aromatic.

Provided that one or more substituents have a monocyclic or bicyclic ring system which is monosubstituted or multiply substituted, this ring system can be preferably substituted with optionally 1, 2, 3, 4 or 5, particularly preferably with optionally 1, 2 or 3 substituents, which can be mutually independently selected from the group comprising F, Cl, Br, I, —CN, —NO$_2$, —OH, —SH, —NH$_2$, oxo(=O), thioxo(=S), —C(=O)—OH, $C_{1-5}$-alkyl, —$C_{2-5}$-alkenyl, —$C_{2-5}$-alkynyl, —C≡C—Si(CH$_3$)$_3$, —C≡C—Si(C$_2$H$_5$)$_3$, —(CH$_2$)—O—$C_{1-5}$-alkyl, —S—$C_{1-5}$-alkyl, —S-phenyl, —S—CH$_2$-phenyl, —O—$C_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—$C_{1-5}$-alkyl, —S(=O)—$C_{1-5}$-alkyl, —NH—$C_{1-5}$-alkyl, —N($C_{1-5}$-alkyl)($C_{1-5}$-alkyl), —C(=O)—O—$C_{1-5}$-alkyl, —C(=O)—H, —C(=O)—$C_{1-5}$-alkyl, —CH$_2$—O—C(=O)-phenyl, —O—C(=O)-phenyl, —NH—S(=O)$_2$—$C_{1-5}$-alkyl, —NH—C(=O)—$C_{1-5}$-alkyl, —C(=O)—NH$_2$, —C(=O)—NH—$C_{1-5}$-alkyl, —C(=O)—N($C_{1-5}$-alkyl)$_2$, pyrazolyl, phenyl, furyl (furanyl), thiadiazolyl, thiophenyl (thienyl) and benzyl, whereby the above-mentioned $C_{1-5}$-alkyl residues can in each case be linear or branched and the cyclic substituents or the cyclic residues of these substituents themselves can in each case be substituted with optionally 1, 2, 3, 4 or 5, preferably with optionally 1, 2, 3 or 4 substituents mutually independently selected from the group comprising F, Cl, Br, I, —CN, —CF$_3$, —OH, —NH$_2$, —O—CF$_3$, —SH, —O—$C_{1-5}$-alkyl, —O-phenyl, —O—CH$_2$-phenyl, —(CH$_2$)—O—$C_{1-5}$-alkyl, —S—$C_{1-5}$-alkyl, —S-phenyl, —S—CH$_2$-phenyl, —$C_{1-5}$-alkyl, —$C_{2-5}$-alkenyl, —$C_{2-5}$-alkynyl, —C≡C—Si(CH$_3$)$_3$, —C≡C—Si(C$_2$H$_5$)$_3$, —C(=O)—O—$C_{1-5}$-alkyl and —C(=O)—CF$_3$.

The substituents can be particularly preferably, in each case mutually independently, selected from the group comprising F, Cl, Br, I, —CN, —NO$_2$, —OH, —SH, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —NH$_2$, oxo(=O), —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, phenyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, phenyl, furyl (furanyl), thiadiazolyl, thiophenyl (thienyl) and benzyl, whereby the cyclic substituents or the cyclic residues of these substituents themselves can be substituted with optionally 1, 2, 3, 4 or 5, preferably with 1, 2, 3 or 4 substituents mutually independently selected from the group comprising F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —C(=O)—O—$C_{1-5}$-alkyl and —C(=O)—CF$_3$.

By way of example, (1,2,3,4)-tetrahydrochinolinyl, (1,2,3,4)-tetrahydroisochinolinyl, (2,3)-dihydro-1H-isoindolyl, (1,2,3,4)-tetrahydronaphthyl, (2,3)-dihydro-benzo[1.4]dioxinyl, benzo[1.3]dioxolyl, (3,4)-dihydro-2H-benzo[1.4]oxazinyl and octahydro-pyrrolo[3,4-c]pyrrolyl are cited as a suitable cycloalkyl residue, heterocycloalkyl residue, cycloalkenyl residue or heterocycloalkenyl residue which can be unsubstituted or monosubstituted or multiply substituted and are condensed with a mono- or bicyclic ring system.

Provided that one or more of the substituents denote a cycloalkyl residue, heterocycloalkyl residue, cycloalkenyl residue or heterocycloalkenyl residue or have such a residue which is monosubstituted or multiply substituted, this residue can preferably be substituted with optionally 1, 2, 3, 4 or 5, particularly preferably with optionally 1, 2 or 3 substituents mutually independently selected from the group comprising F, Cl, Br, I, —CN, —CF$_3$, —OH, —NH$_2$, —O—CF$_3$, —SH, —O—$C_{1-5}$-alkyl, —O-phenyl, —O—CH$_2$-phenyl, —(CH$_2$)—O—$C_{1-5}$-alkyl, —S—$C_{1-5}$-alkyl, —S-phenyl, —S—CH$_2$-phenyl, —$C_{1-5}$-alkyl, —$C_{2-5}$-alkenyl, —$C_{2-5}$-alkynyl, —C≡C—Si(CH$_3$)$_3$, —C≡C—Si(C$_2$H$_5$)$_3$, —C(=O)—O—$C_{1-5}$-alkyl, —C(=O)—CF$_3$, —S(=O)$_2$—$C_{1-5}$-alkyl, —S(=O)—$C_{1-5}$-alkyl, —S(=O)$_2$-phenyl, oxo(=O), thioxo(=S), —N($C_{1-5}$-alkyl)$_2$, —N(H)($C_{1-5}$-alkyl), —NO$_2$, —S—CF$_3$, —C(=O)—OH, —NH—S(=O)$_2$—$C_{1-5}$-alkyl, —NH—C(=O)—$C_{1-5}$-alkyl, —C(=O)—H, —C(=O)—$C_{1-5}$-alkyl, —C(=O)—NH$_2$, —C(=O)—N($C_{1-5}$-alkyl)$_2$, —C(=O)—N(H)($C_{1-5}$-alkyl) and phenyl, whereby the above-mentioned $C_{1-5}$-alkyl residues can in each case be linear or branched and the phenyl residues can be respectively unsubstituted or substituted with 1, 2, 3, 4 or 5, preferably with 1, 2, 3 or 4 substituents mutually independently selected from the group comprising F, Cl, Br, I, —CN, —CF$_3$, —OH, —NH$_2$, —O—CF$_3$, —SH, —O—$C_{1-5}$-alkyl, —O-phenyl, —O—CH₂-phenyl, —(CH₂)—O—C₁₋₅-alkyl, —S—C₁₋₅-alkyl, —S-phenyl, —S—CH₂-phenyl, —C₁₋₅-alkyl, —C₂₋₅-alkenyl, —C₂₋₅-alkynyl, —C≡C—Si(CH₃)₃, —C≡C—Si(C₂H₅)₃, —C(=O)—O—C₁₋₅-alkyl and —C(=O)—CF₃.

The substituents can be particularly preferably, in each case mutually independently, selected from the group comprising F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH₃)₃, —C≡C—Si(C₂H₅)₃, —OH, oxo, thioxo, —O—CH₃, —O—C₂H₅, —O—C₃H₇, —(CH₂)—O—CH₃, —(CH₂)—O—C₂H₅, —NH₂, —N(CH₃)₂, —N(C₂H₅)₂, —NH—CH₃, —NH—C₂H₅, —NO₂, —CF₃, —O—CF₃, —S—CF₃, —SH, —S—CH₃, —S—C₂H₅, —S(=O)—CH₃, —S(=O)₂—CH₃, —S(=O)—C₂H₅, —S(=O)₂—C₂H₅, —NH—S(=O)₂—CH₃, —C(=O)—OH, —C(=O)—H; —C(=O)—CH₃, —C(=O)—C₂H₅, —C(=O)—N(CH₃)₂, —C(=O)—NH—CH₃, —C(=O)—NH₂, —NH—C(=O)—CH₃, —NH—C(=O)—C₂H₅, —C(=O)—O—CH₃, —C(=O)—O—C₂H₅, —C(=O)—O—C(CH₃)₃ and phenyl, whereby the phenyl residue can be substituted with 1, 2, 3, 4 or 5, preferably 1, 2 or 3 substituents mutually independently selected from the group comprising F, Cl, Br, I, —CN, —CF₃, —OH, —NH₂, —O—CF₃, —SH, —O—CH₃, —O—C₂H₅, —O—C₃H₇, methyl, ethyl, n-propyl, isopropyl, n-butyl, 2-butyl, tert-butyl, ethenyl, allyl, ethynyl, propynyl, —C≡C—Si(CH₃)₃, —C≡C—Si(C₂H₅)₃, —C(=O)—O—C₁₋₅-alkyl and —C(=O)—CF₃.

The term "aryl" means, in the context of the present invention, a mono- or polycyclic, preferably a mono- or bicyclic, aromatic hydrocarbon residue with preferably 6, 10 or 14 C-atoms. An aryl residue can be unsubstituted or monosubstituted or multiply identically or differently substituted. By way of example, phenyl-, 1-naphthyl, 2-naphthyl and anthracenyl are cited as suitable aryl residues. An aryl residue is particularly preferably a phenyl residue.

The term "heteroaryl" means, in the context of the present invention, a monocyclic or polycyclic, preferably a mono-, bi- or tricyclic, aromatic hydrocarbon residue with preferably 5, 6, 7, 8, 9, 10, 11, 12, 13 or 14 C-atoms, particularly preferably with 5, 6, 9, 10, 13 or 14 C-atoms, very particularly preferably with 5 or 6 C-atoms, in which one or more C-atoms have in each case been replaced by a heteroatom mutually independently selected from the group comprising oxygen, sulphur and nitrogen (NH). Heteroaryl residues can preferably have 1, 2, 3, 4 or 5, particularly preferably 1, 2 or 3 heteroatom(s) mutually independently selected from the group comprising oxygen, sulphur and nitrogen (NH) as the ring member(s). A heteroaryl residue can be unsubstituted or monosubstituted or multiply identically or differently substituted.

By way of example, indolizinyl, benzimidazolyl, tetrazolyl, triazinyl, isoxazolyl, phthalazinyl, carbazolyl, carbolinyl, diaza-naphthyl, thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, pyrimidinyl, indazolyl, chinoxalinyl, chinazolinyl, chinolinyl, naphthridinyl and isochinolinyl are cited as suitable heteroaryl residues.

Aryl or heteroaryl residues can, in the context of the present invention, be condensed (annelated) with a mono- or bicyclic ring system.

(2,3)-dihydrobenzo[b]thiophenyl, (2,3)-dihydro-1H-indenyl, indolinyl, (2,3)-dihydrobenzofuranyl, (2,3)-dihydrobenzo[d]oxazolyl, benzo[d][1,3]dioxolyl, benzo[d][1,3]oxathiolyl, isoindolinyl, (1,3)-dihydroisobenzofuranyl, (1,3)-dihydrobenzo[c]thiophenyl, (1,2,3,4)-tetrahydronaphthyl, (1,2,3,4)-tetrahydrochinolinyl, chromanyl, thiochromanyl, (1,2,3,4)-tetrahydroisochinolinyl, (1,2,3,4)-tetrahydrochinoxalinyl, (3,4)-dihydro-2H-benzo[b][1,4]oxazinyl, (3,4)-dihydro-2H-benzo[b][1,4]thiazinyl, (2,3)-dihydrobenzo[b][1,4]dioxinyl, (2,3)-dihydrobenzo[b][1,4]oxathiinyl, (6,7,8,9)-tetrahydro-5H-benzo[7]annulenyl, (2,3,4,5)-tetrahydro-1H-benzo[b]azepinyl and (2,3,4,5)-tetrahydro-1H-benzo[c]azepinyl are cited as examples of aryl residues which are condensed with a mono- or bicyclic ring system.

Unless indicated otherwise, provided that one or more of the substituents denote an aryl or heteroaryl residue or have an aryl or heteroaryl residue which is monosubstituted or multiply substituted, these aryl or heteroaryl residues can preferably be substituted with optionally 1, 2, 3, 4 or 5, particularly preferably with optionally 1, 2 or 3 substituents mutually independently selected from the group comprising F, Cl, Br, I, —CN, —NO₂, —OH, —SH, —NH₂, —C(=O)—OH, —C₁₋₅-alkyl, —(CH₂)—O—C₁₋₅-alkyl, —C₂₋₅-alkenyl, —C₂₋₅-alkynyl, —C≡C—Si(CH₃)₃, —C≡C—Si(C₂H₅)₃, —S—C₁₋₅-alkyl, —S-phenyl, —S—CH₂-phenyl, —O—C₁₋₅-alkyl, —O-phenyl, —O—CH₂-phenyl, —CF₃, —CHF₂, —CH₂F, —O—CF₃, —O—CHF₂, —O—CH₂F, —C(=O)—CF₃, —S—CF₃, —S—CHF₂, —S—CH₂F, —S(=O)₂-phenyl, —S(=O)₂—C₁₋₅-alkyl, —S(=O)—C₁₋₅-alkyl, —NH—C₁₋₅-alkyl, N(C₁₋₅-alkyl)₂, —C(=O)—O—C₁₋₅-alkyl, —C(=O)—O-phenyl, —C(=O)—H; —C(=O)—C₁₋₅-alkyl, —CH₂—O—C(=O)-phenyl, —O—C(=O)—C₁₋₅-alkyl, —O—C(=O)-phenyl, —NH—S(=O)₂—C₁₋₅-alkyl, —NH—C(=O)—C₁₋₅-alkyl, —C(=O)—NH₂, —C(=O)—NH—C₁₋₅-alkyl, —C(=O)—N(C₁₋₅-alkyl)₂, —C(=O)—N(C₁₋₅-alkyl)(phenyl), —C(=O)—NH-phenyl, cyclopropyl, cyclobutyl, cyclopentyl, cyclohexyl, pyrazolyl, phenyl, furyl (furanyl), thiazolyl, thiadiazolyl, thiophenyl (thienyl), benzyl and phenethyl, whereby the above-mentioned C₁₋₅-alkyl residues can in each case be linear or branched and the cyclic substituents or the cyclic residues of these substituents themselves can be substituted with optionally 1, 2, 3, 4 or 5, preferably with optionally 1, 2, 3 or 4 substituents mutually independently selected from the group comprising F, Cl, Br, I, —CN, —NO₂, —OH, —SH, —NH₂, —C(=O)—OH, —C₁₋₅-alkyl, —(CH₂)—O—C₁₋₅-alkyl, —C₂₋₅-alkenyl, —C₂₋₅-alkynyl, —C≡C—Si(CH₃)₃, —C≡C—Si(C₂H₅)₃, —S—C₁₋₅-alkyl, —S-phenyl, —S—CH₂-phenyl, —O—C₁₋₅-alkyl, —O-phenyl, —O—CH₂-phenyl, —CF₃, —CHF₂, —CH₂F, —O—CF₃, —O—CHF₂, —O—CH₂F, —C(=O)—CF₃, —S—CF₃, —S—CHF₂ and —S—CH₂F.

The substituents can be particularly preferably, in each case mutually independently selected from the group comprising F, Cl, Br, I, —CN, —NO₂, —OH, —SH, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH₃)₃, —C≡C—Si(C₂H₅)₃, —CH₂—O—CH₃, —CH₂—O—C₂H₅, —OH, —SH, —NH₂, —C(=O)—OH, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —O—C(CH₃)₃, —CF₃, —CHF₂, —CH₂F, —O—CF₃, —O—CHF₂, —O—CH₂F, —C(=O)—CF₃, —S—CF₃, —S—CHF₂, —S—CH₂F, —S(=O)₂-phenyl, pyrazolyl, phenyl, —N(CH₃)₂, —N(C₂H₅)₂, —NH—CH₃, —NH—C₂H₅, —CH₂—O—C(=O)-phenyl, —NH—S(=O)₂—CH₃, —C(=O)—O—CH₃, —C(=O)—O—C₂H₅, —C(=O)—

O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, —C(=O)—O—CH(CH$_3$)$_2$, —C(=O)—O—(CH$_2$)$_3$—CH$_3$, —C(=O)—O-phenyl, —O—C(=O)—CH$_3$, —O—C(=O)—C$_2$H$_5$, —C(=O)—NH—C$_2$H$_5$, —C(=O)—NH—C(CH$_3$)$_3$, —C(=O)—N(C$_2$H$_5$)$_2$, —C(=O)—NH-phenyl, —C(=O)—N(CH$_3$)-phenyl, —C(=O)—N(C$_2$H$_5$)-phenyl, cyclopropyl, cyclobutyl, cyclopentyl, cyclohexyl, phenyl, furyl (furanyl), thiadiazolyl, thiophenyl (thienyl) and benzyl, whereby the cyclic substituents or the cyclic residues of these substituents themselves can in each case be substituted with optionally 1, 2, 3, 4, or 5, preferably with optionally 1, 2, 3 or 4 substituents mutually independently selected from the group comprising F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

A substituted aryl residue can very particularly preferably be selected from the group comprising 2-methyl-phenyl, 3-methyl-phenyl, 4-methyl-phenyl, 2-fluoro-phenyl, 3-fluoro-phenyl, 4-fluoro-phenyl, 2-cyano-phenyl, 3-cyano-phenyl, 4-cyano-phenyl, 2-hydroxy-phenyl, 3-hydroxy-phenyl, 4-hydroxy-phenyl, 2-amino-phenyl, 3-amino-phenyl, 4-amino-phenyl, 2-dimethylamino-phenyl, 3-dimethylamino-phenyl, 4-dimethylamino-phenyl, 2-methylamino-phenyl, 3-methylamino-phenyl, 4-methylamino-phenyl, 2-acetyl-phenyl, 3-acetyl-phenyl, 4-acetyl-phenyl, 2-methylsulfinyl-phenyl, 3-methylsulfinyl-phenyl, 4-methylsulfinyl-phenyl, 2-methylsulfonyl-phenyl, 3-methylsulfonyl-phenyl, 4-methylsulfonyl-phenyl, 2-methoxy-phenyl, 3-methoxy-phenyl, 4-methoxy-phenyl, 2-chloro-phenyl, 3-chloro-phenyl, 4-chloro-phenyl, 2-ethoxy-phenyl, 3-ethoxy-phenyl, 4-ethoxyphenyl, 2-trifluoromethyl-phenyl, 3-trifluoromethyl-phenyl, 4-trifluoromethyl-phenyl, 2-difluoromethyl-phenyl, 3-difluoromethyl-phenyl, 4-difluoromethyl-phenyl, 2-fluoromethyl-phenyl, 3-fluoromethyl-phenyl, 4-fluoromethyl-phenyl, 2-nitro-phenyl, 3-nitro-phenyl, 4-nitro-phenyl, 2-ethyl-phenyl, 3-ethyl-phenyl, 4-ethyl-phenyl, 2-propyl-phenyl, 3-propyl-phenyl, 4-propyl-phenyl, 2-isopropyl-phenyl, 3-isopropyl-phenyl, 4-isopropyl-phenyl, 2-tert-butyl-phenyl, 3-tert-butyl-phenyl, 4-tert-butyl-phenyl, 2-carboxyphenyl, 3-carboxy-phenyl, 4-carboxyphenyl, 2-ethenyl-phenyl, 3-ethenyl-phenyl, 4-ethenyl-phenyl, 2-ethynyl-phenyl, 3-ethynyl-phenyl, 4-ethynyl-phenyl, 2-allyl-phenyl, 3-allyl-phenyl, 4-allyl-phenyl, 2-trimethylsilanylethynyl-phenyl, 3-trimethylsilanylethynyl-phenyl, 4-trimethylsilanylethynyl-phenyl, 2-formyl-phenyl, 3-formyl-phenyl, 4-formyl-phenyl, 2-acetamino-phenyl, 3-acetamino-phenyl, 4-acetamino-phenyl, 2-dimethylaminocarbonyl-phenyl, 3-dimethylaminocarbonyl-phenyl, 4-dimethylaminocarbonyl-phenyl, 2-methoxymethyl-phenyl, 3-methoxymethyl-phenyl, 4-methoxymethyl-phenyl, 2-ethoxymethyl-phenyl, 3-ethoxymethyl-phenyl, 4-ethoxymethyl-phenyl, 2-aminocarbonyl-phenyl, 3-aminocarbonyl-phenyl, 4-aminocarbonyl-phenyl, 2-methylaminocarbonyl-phenyl, 3-methylaminocarbonyl-phenyl, 4-methylaminocarbonyl-phenyl, 2-carboxymethylester-phenyl, 3-carboxymethylester-phenyl, 4-carboxymethylester-phenyl, 2-carboxyethylester-phenyl, 3-carboxyethylester-phenyl, 4-carboxyethylester-phenyl, 2-carboxy-tert-butylester-phenyl, 3-carboxy-tert-butylester-phenyl, 4-carboxy-tert-butylester-phenyl, 2-methylmercapto-phenyl, 3-methylmercapto-phenyl, 4-methylmercapto-phenyl, 2-ethylmercapto-phenyl, 3-ethylmercapto-phenyl, 4-ethylmercapto-phenyl, 2-biphenyl, 3-biphenyl, 4-biphenyl, 2-bromophenyl, 3-bromophenyl, 4-bromophenyl, 2-iodophenyl, 3-iodophenyl, 4-iodophenyl, 2-trifluoromethoxy-phenyl, 3-trifluoromethoxy-phenyl, 4-trifluoromethoxy-phenyl, 2-fluoro-3-trifluoromethylphenyl, 2-fluoro-4-methyl-phenyl, (2,3)-difluorophenyl, (2,3)-dimethyl-phenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluoro-phenyl, 2-chloro-4-nitro-phenyl, 2-chloro-4-methyl-phenyl, 2-chloro-5-trifluoromethyl-phenyl, 2-chloro-5-methoxy-phenyl, 2-bromo-5-trifluoromethyl-phenyl, 2-bromo-5-methoxy-phenyl, (2,4)-dibromo-phenyl, (2,4)-dimethyl-phenyl, 2-fluoro-4-trifluoromethyl-phenyl, (2,5)-difluoro-phenyl, 2-fluoro-5-trifluoromethyl-phenyl, 5-fluoro-2-trifluoromethyl-phenyl, 5-chloro-2-trifluoromethyl-phenyl, 5-bromo-2-trifluoromethyl-phenyl, (2,5)-dimethoxy-phenyl, (2,5)-bis-trifluoromethyl-phenyl, (2,5)-dichloro-phenyl, (2,5)-dibromo-phenyl, 2-methoxy-5-nitro-phenyl, 2-fluoro-6-trifluoromethyl-phenyl, (2,6)-dimethoxy-phenyl, (2,6)-dimethyl-phenyl, (2,6)-dichloro-phenyl, 2-chloro-6-fluoro-phenyl, 2-bromo-6-chloro-phenyl, 2-bromo-6-fluoro-phenyl, (2,6)-difluoro-phenyl, (2,6)-difluoro-3-methyl-phenyl, (2,6)-dibromo-phenyl, (2,6)-dichlorophenyl, 3-chloro-2-fluoro-phenyl, 3-chloro-5-methyl-phenyl, (3,4)-dichlorophenyl, (3,4)-dimethyl-phenyl, 3-methyl-4-methoxy-phenyl, 4-chloro-3-nitro-phenyl, (3,4)-dimethoxy-phenyl, 4-fluoro-3-trifluoromethylphenyl, 3-fluoro-4-trifluoromethyl-phenyl, (3,4)-difluoro-phenyl, 3-cyano-4-fluoro-phenyl, 3-cyano-4-methyl-phenyl, 3-cyano-4-methoxy-phenyl, 3-bromo-4-fluoro-phenyl, 3-bromo-4-methyl-phenyl, 3-bromo-4-methoxy-phenyl, 4-chloro-2-fluoro-phenyl, 4-chloro-3-trifluoromethyl, 4-bromo-3-methyl-phenyl, 4-bromo-5-methyl-phenyl, 3-chloro-4-fluoro-phenyl, 4-fluoro-3-nitrophenyl, 4-bromo-3-nitro-phenyl, (3,4)-dibromo-phenyl, 4-chloro-3-methyl-phenyl, 4-bromo-3-methyl-phenyl, 4-fluoro-3-methyl-phenyl, 3-fluoro-4-methyl-phenyl, 3-fluoro-5-methyl-phenyl, 2-fluoro-3-methyl-phenyl, 4-methyl-3-nitro-phenyl, (3,5)-dimethoxy-phenyl, (3,5)-dimethyl-phenyl, (3,5)-bis-trifluoromethyl-phenyl, (3,5)-difluoro-phenyl, (3,5)-dinitro-phenyl, (3,5)-dichloro-phenyl, 3-fluoro-5-trifluoromethyl-phenyl, 5-fluoro-3-trifluoromethyl-phenyl, (3,5)-dibromo-phenyl, 5-chloro-4-fluoro-phenyl, 5-chloro-4-fluoro-phenyl, 5-bromo-4-methyl-phenyl, (2,3,4)-trifluorophenyl, (2,3,4)-trichlorophenyl, (2,3,6)-trifluoro-phenyl, 5-chloro-2-methoxy-phenyl, (2,3)-difluoro-4-methyl, (2,4,5)-trifluoro-phenyl, (2,4,5)-trichloro-phenyl, (2,4)-dichloro-5-fluoro-phenyl, (2,4,6)-trichloro-phenyl, (2,4,6)-trimethylphenyl, (2,4,6)-trifluoro-phenyl, (2,4,6)-trimethoxy-phenyl, (3,4,5)-trimethoxy-phenyl, (2,3,4,5)-tetrafluoro-phenyl, 4-methoxy-(2,3,6)-trimethyl-phenyl, 4-methoxy-(2,3,6)-trimethyl-phenyl, 4-chloro-2,5-dimethyl-phenyl, 2-chloro-6-fluoro-3-methyl-phenyl, 6-chloro-2-fluoro-3-methyl, (2,4,6)-trimethylphenyl and (2,3,4,5,6)-pentafluoro-phenyl.

A substituted heteroaryl residue can very particularly preferably be selected from the group comprising 3-methyl-pyrid-2-yl, 4-methyl-pyrid-2-yl, 5-methyl-pyrid-2-yl, 6-methyl-pyrid-2-yl, 2-methyl-pyrid-3-yl, 4-methyl-pyrid-3-yl, 5-methyl-pyrid-3-yl, 6-methyl-pyrid-3-yl, 2-methyl-pyrid-4-yl, 3-methyl-pyrid-4-yl, 3-fluoro-pyrid-2-yl, 4-fluoro-pyrid-2-yl, 5-fluoro-pyrid-2-yl, 6-fluoro-pyrid-2-yl, 3-chloro-pyrid-2-yl, 4-chloro-pyrid-2-yl, 5-chloro-pyrid-2-yl, 6-chloro-pyrid-2-yl, 3-trifluoromethyl-pyrid-2-yl, 4-trifluoromethyl-pyrid-2-yl, 5-trifluoromethyl-pyrid-2-yl, 6-trifluoromethyl-pyrid-2-yl, 3-methoxy-pyrid-2-yl, 4-methoxy-pyrid-2-yl, 5-methoxy-pyrid-2-yl, 6-methoxy-pyrid-2-yl, 4-methyl-thiazol-2-yl, 5-methyl-thiazol-2-yl, 4-trifluoromethyl-thiazol-2-yl, 5-trifluoromethyl-thiazol-2-yl, 4-chloro-thiazol-2-yl, 5-chloro-thiazol-2-yl, 4-bromo-thiazol-2-yl, 5-bromo-thiazol-2-yl, 4-fluoro-thiazol-2-yl, 5-fluoro-thiazol-2-yl, 4-cyano-thiazol-2-yl, 5-cyano-thiazol-2-yl, 4-methoxy-thiazol-2-yl, 5-methoxy-thiazol-2-yl, 4-methyl-oxazol-2-yl, 5-methyl-oxazol-2-yl, 4-trifluoromethyl-oxazol-2-yl, 5-trifluoromethyl-oxazol-2-yl, 4-chloro-oxazol-2-yl, 5-chloro-oxazol-2-yl, 4-bromo-oxazol-2-yl, 5-bromo-oxazol-2-yl, 4-fluoro-oxazol-2-yl, 5-fluoro-oxazol-2-yl, 4-cyano-oxazol-2-yl, 5-cyano-oxazol-2-yl, 4-methoxy-oxazol-2-yl, 5-methoxy-oxazol-2-yl, 2-methyl-(1,2,4)-thiadiazol-5-yl, 2-trifluoromethyl-(1,2,4)-thiadiazol-5-yl, 2-chloro-(1,2,4)-thiadiazol-5-yl, 2-fluoro-(1,2,4)-thiadiazol-5-yl, 2-methoxy-(1,2,4)-thiadiazol-5-yl, 2-cyano-(1,2,4)-thiadiazol-5-yl, 2-methyl-(1,2,4)-oxadiazol-5-yl, 2-trifluoromethyl-(1,2,4)-oxadiazol-5-yl, 2-chloro-(1,2,4)-oxadiazol-5-yl, 2-fluoro-(1,2,4)-oxadiazol-5-yl, 2-methoxy-(1,2,4)-oxadiazol-5-yl and 2-cyano-(1,2,4)-oxadiazol-5-yl.

The term "alkylene" encompasses, in the context of the present invention, acyclic saturated hydrocarbon chains which connect an aryl, heteroaryl, cycloalkyl, heterocycloalkyl, cycloalkenyl or heterocycloalkenyl residue to the compounds of the general formula I or to another substituent. Alkylene chains can be branched or straight-chained and unsubstituted or at least monosubstituted with as in the case of $C_{1-12}$-alkylene 1 to 12 (i.e. 1, 2, 3, 4, 5, 6, 7, 8, 9, 10, 11 or 12) C-atoms, with as in the case of $C_{1-6}$-alkylene 1 to 6 (i.e. 1, 2, 3, 4, 5 or 6) C-atoms or with as in the case of $C_{1-3}$-alkylene 1 to 3 (i.e. 1, 2 or 3) C-atoms. $C_{1-6}$-alkylene groups such as —(CH$_2$)—, —(CH$_2$)$_2$—, —C(H)(CH$_3$)—, —(CH$_2$)$_3$—, —(CH$_2$)$_4$—, —(CH$_2$)$_5$—, —C(CH$_3$)$_2$—, —C(H)(CH$_3$)—, —C(H)(C(H)(CH$_3$)$_2$)— and C(C$_2$H$_5$)(H)— are cited by way of example. —(CH$_2$)—, —(CH$_2$)$_2$— and —(CH$_2$)$_3$— are cited by way of example as a suitable $C_{1-3}$-alkylene group.

The term "alkenylene" encompasses, in the context of the present invention, acyclic unsaturated hydrocarbon chains which connect an aryl, heteroaryl, cycloalkyl, heterocycloalkyl, cycloalkenyl or heterocycloalkenyl residue to the compounds of the general formula I or to another substituent. Alkenylene chains have at least one double-bond, preferably 1, 2 or 3 double-bonds, and can be branched or straight-chained and unsubstituted or at least monosubstituted with as in the case of $C_{2-12}$-alkenylene 2 to 12 (i.e. 2, 3, 4, 5, 6, 7, 8, 9, 10, 11 or 12) C-atoms, with as in the case of $C_{2-6}$-alkenylene 2 to 6 (i.e. 2, 3, 4, 5 or 6) C-atoms or with as in the case of $C_{2-3}$-alkenylene 2 to 3 (i.e. 2 or 3) C-atoms. $C_{2-3}$-alkenylene groups such as —CH═CH— and —CH$_2$—CH═CH— are cited by way of example.

The term "alkynylene" encompasses, in the context of the present invention, acyclic unsaturated hydrocarbon chains which connect an aryl, heteroaryl, cycloalkyl, heterocycloalkyl, cycloalkenyl or heterocycloalkenyl residue to the compounds of the general formula I or to another substituent. Alkynylene chains have at least one triple-bond, preferably 1 or 2 triple-bonds, and can be branched or straight-chained and unsubstituted or at least monosubstituted with as in the case of $C_{2-12}$-alkynylene 2 to 12 (i.e. 2, 3, 4, 5, 6, 7, 8, 9, 10, 11 or 12) C-atoms, with as in the case of $C_{2-6}$-alkynylene 2 to 6 (i.e. 2, 3, 4, 5 or 6) C-atoms or with as in the case of $C_{2-3}$-alkynylene 2 to 3 (i.e. 2 or 3) C-atoms. $C_{2-3}$-alkynylene groups such as —C≡C— and —CH$_2$—C≡C— are cited by way of example.

The term "heteroalkylene" denotes an alkylene chain as described above, in which one or more C-atoms have in each case been replaced by a heteroatom mutually independently selected from the group comprising oxygen, sulphur and nitrogen (NH). Heteroalkylene groups can preferably have 1, 2 or 3 heteroatom(s), particularly preferably one heteroatom, selected from the group comprising oxygen, sulphur and nitrogen (NH) as the chain member(s). Heteroalkylene groups can preferably be 2- to 12-membered, particularly preferably 2- to 6-membered, very particularly preferably 2- or 3-membered.

Heteroalkylene groups such as —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —CH$_2$—NH—CH$_2$—, —CH$_2$—NH— and —CH$_2$—CH$_2$—NH—CH$_2$—CH$_2$ are cited by way of example.

The term "heteroalkenylene" denotes an alkenylene chain as described above, in which one or more C-atoms have in each case been replaced by a heteroatom mutually independently selected from the group comprising oxygen, sulphur and nitrogen (NH). Heteroalkenylene groups can preferably have 1, 2 or 3 heteroatom(s), particularly preferably 1 heteroatom, selected from the group comprising oxygen, sulphur and nitrogen (NH) as the chain member(s). Heteroalkenylene groups can preferably be 2- to 12-membered, particularly preferably 2- to 6-membered, very particularly preferably 2- or 3-membered. Heteroalkenylene groups such as —CH═CH—NH—, —CH═CH—O— and —CH═CH—S— are cited by way of example.

Provided that one or more of the substituents denote an alkylene, alkenylene, alkynylene, heteroalkylene or heteroalkenylene group or have such a group which is monosubstituted or multiply substituted, this group can preferably be substituted with optionally 1, 2, 3, 4 or 5, particularly preferably with optionally 1, 2 or 3 substituents mutually independently selected from the group comprising phenyl, F, Cl, Br, I, —NO$_2$, —CN, —OH, —O-phenyl, —O—CH$_2$-phenyl, —SH, —S-phenyl, —S—CH$_2$-phenyl, —NH$_2$, —N(C$_{1-5}$-alkyl)$_2$, —NH-phenyl, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(═O)—H, —C(═O)—C$_{1-5}$-alkyl, —C(═O)-phenyl, —C(═S)—C$_{1-5}$-alkyl, —C(═S)-phenyl, —C(═O)—OH, —C(═O)—O—C$_{1-5}$-alkyl, —C(═O)—O-phenyl, —C(═O)—NH$_2$, —C(═O)—NH—C$_{1-5}$-alkyl, —C(═O)—N(C$_{1-5}$-alkyl)$_2$, —S(═O)—C$_{1-5}$-alkyl, —S(═O)-phenyl, —S(═O)$_2$—C$_{1-5}$-alkyl, —S(═O)$_2$-phenyl, —S(═O)$_2$—NH$_2$ and —SO$_3$H, whereby the above-mentioned C$_{1-5}$-alkyl residues can in each case be linear or branched and the above-mentioned phenyl residues can be substituted with 1, 2, 3, 4 or 5, preferably with 1, 2, 3 or 4 substituents mutually independently selected from the group comprising F, Cl, Br, I, —CN, —NO$_2$, —OH, —SH, —NH$_2$, —C(═O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$ and —S—CH$_2$F.

Alkylene, alkenylene, alkynylene, heteroalkylene or heteroalkenylene groups can particularly preferably be substituted with 1, 2 or 3 substituents mutually independently selected from the group comprising phenyl, F, Cl, Br, I, —NO$_2$, —CN, —OH, —O-phenyl, —SH, —S-phenyl, —NH$_2$, —N(CH$_3$)$_2$, —N(C$_2$H$_5$)$_2$ and —N(CH$_3$)(C$_2$H$_5$), whereby the phenyl residue can be substituted with 1, 2, 3, 4 or 5 substituents mutually independently selected from the group comprising F, Cl, Br, I, —OH, —SH, —NO$_2$, —CN, —O—CH$_3$, —O—CF$_3$ and —O—C$_2$H$_5$.

Provided that compounds of the general formula I have several substituents selected from the group comprising R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$ and R$^{27}$ with the same designation, each of these substituents can be in each case selected independently of other substituents with the same designation of the substituents.

For example, the following residue

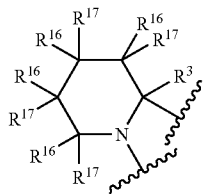

can denote this residue after selection of the corresponding substituents

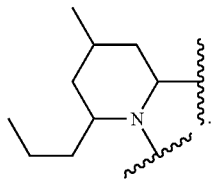

Propiolic acid amides of the general formula I indicated above are preferred, in which a, b and c, mutually independently, in each case denote 0 or 1, whereby the sum of a, b and c is equal to 1, 2 or 3;

A denotes one of the following residues

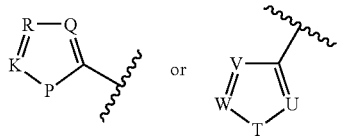

Q and U respectively denote CR$^{10}$ or N;
R and V respectively denote CR$^{11}$ or N;
K and W respectively denote CR$^{12}$ or N;
P and T respectively denote O, S or NR$^{13}$;
with the proviso that compounds are excluded in which P denotes S, Q denotes N, R denotes CR$^{11}$ and K denotes CR$^{12}$ or N;
R$^1$ and R$^8$, mutually independently, in each case denote H; —C(=O)—R$^{28}$; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

R$^2$, R$^3$, R$^4$, R$^5$, R$^6$, R$^7$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$ and R$^{27}$, mutually independently, in each case denote H; F; Cl; Br; I; —NO$_2$; —CN; —NH$_2$; —OH; —SH; —C(=O)—OH; —C(=O)—H; —NH—C(=O)—H; —C(=O)—R$^{28}$; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; —NH—R$^{35}$; —NR$^{36}$R$^{37}$; —O—C(=O)—R$^{38}$; —NH—C(=O)—R$^{39}$; —NR$^{40}$—C(=O)—R$^{41}$; —O—R$^{42}$; —S—R$^{43}$; —NH—C(=O)—NH—R$^{44}$; —NH—C(=S)—NH—R$^{45}$; —NH—S(=O)$_2$—R$^{46}$; —NR$^{47}$—S(=O)$_2$—R$^{48}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

or R$^2$ and R$^3$ or R$^4$ and R$^5$ or R$^6$ and R$^7$ or R$^{14}$ and R$^{15}$ or R$^{16}$ and R$^{17}$ or R$^{18}$ and R$^{19}$ or R$^{20}$ and R$^{21}$ or R$^{22}$ and R$^{23}$ or R$^{24}$ and R$^{25}$ or R$^{26}$ and R$^{27}$, mutually independently, jointly denote a residue selected from the group comprising an oxo group (=O) and a thioxo group (=S);

or R¹ and R⁸ together with the —N—CR²R³—(CR⁴R⁵)_b— (CR⁶R⁷)_c group joining them together form a residue of the general formula B,

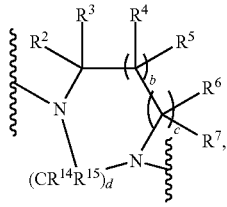

B whereby d denotes 1, 2 or 3 and b denotes 0 or 1 and c denotes 0 or 1;
or R¹ and R2 together with the —N—CR³ group joining them together form a residue of the general formula C,

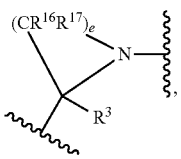

C whereby e denotes 1, 2, 3 or 4 and, in this case, b denotes 0 or 1 and c denotes 0;
or R¹ and R⁴ together with the —N—CR²R³—CR⁵ group joining them together form a residue of the general formula D,

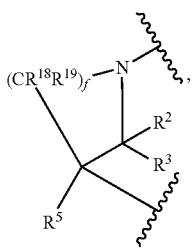

D whereby f denotes 1, 2, 3 or 4, and, in this case, c denotes 0;
or R¹ and R⁶ together with the —N—CR²R³—CR⁴R⁵—CR⁷ group joining them together form a residue of the general formula E,

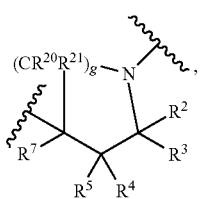

E whereby g denotes 1, 2 or 3;
or R⁶ and R⁸ together with the —N—CR⁷ group joining them together form a residue of the general formula F

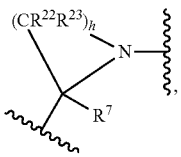

F whereby h denotes 1, 2, 3 or 4 and, in this case, b denotes 0 or 1 and a denotes 0;
or R⁴ and R⁸ together with the —N—CR⁶R⁷—CR⁵ group joining them together form a residue of the general formula G,

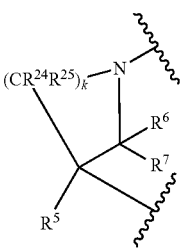

G whereby k denotes 1, 2, 3 or 4, and, in this case, a denotes 0;
or R² and R⁸ together with the —N—CR⁶R⁷—CR⁴R⁵—CR³ group joining them together form a residue of the general formula H,

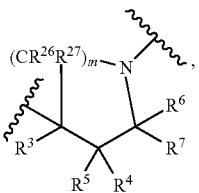

H whereby m denotes 1, 2 or 3;
R⁹ denotes unsubstituted or substituted aryl or unsubstituted or substituted heteroaryl;
R¹⁰, R¹¹ and R¹², mutually independently, in each case denote H; F; Cl; Br; I; —NO₂; —CN; —NH₂; —OH; —SH; —C(=O)—OH; —C(=O)—H; —NH—C(=O)—H; —C(=O)—R²⁸; —C(=O)—O—R²⁹; —C(=O)—NH₂; —C(=O)—NH—R³⁰; —C(=O)—NR³¹R³²; —S(=O)—R³³; —S(=O)₂—R³⁴; —NH—R³⁵; —NR³⁶R³⁷; —O—C(=O)—R³⁸; —NH—C(=O)—R³⁹; —NR⁴⁰—C(=O)—R⁴¹; —O—R⁴²; —S—R⁴³; —NH—C(=O)—NH—R⁴⁴; —NH—C(=S)—NH—R⁴⁵; —NH—S(=O)₂—R⁴⁶; —NR⁴⁷—S(=O)₂—R⁴⁸; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

$R^{13}$ denotes H; —C(=O)—OH; —C(=O)—H; —C(=O)—$R^{28}$; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

and $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$, mutually independently, in each case denote unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

whereby the above-mentioned alkyl residues are in each case branched or straight-chained and have 1, 2, 3, 4, 5, 6, 7, 8, 9, 10, 11 or 12 carbon atoms as chain members;

the above-mentioned alkenyl residues are in each case branched or straight-chained and have 2, 3, 4, 5, 6, 7, 8, 9, 10, 11 or 12 carbon atoms as chain members;

the above-mentioned alkynyl residues are in each case branched or straight-chained and have 2, 3, 4, 5, 6, 7, 8, 9, 10, 11 or 12 carbon atoms as chain members;

the above-mentioned heteroalkyl residues, heteroalkenyl residues and heteroalkynyl residues are in each case 2-, 3-, 4-, 5-, 6-, 7-, 8-, 9-, 10-, 11- or 12-membered;

the above-mentioned heteroalkyl residues, heteroalkenyl residues and heteroalkynyl residues in each case have optionally 1, 2 or 3 heteroatom(s) mutually independently selected from the group comprising oxygen, sulphur and nitrogen as the chain member(s);

the above-mentioned alkyl residues, alkenyl residues, alkynyl residues, heteroalkyl residues, heteroalkenyl residues and heteroalkynyl residues can in each case be substituted with optionally 1, 2, 3, 4 or 5 substituents mutually independently selected from the group comprising F, Cl, Br, I, —$NO_2$, —CN, —OH, —SH, —$NH_2$, —N($C_{1-5}$-alkyl)$_2$, —N($C_{1-5}$-alkyl)(phenyl), —N($C_{1-5}$-alkyl)($CH_2$-phenyl), —N($C_{1-5}$-alkyl)($CH_2$—$CH_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—$NH_2$, —C(=O)—NH—$C_{1-5}$-alkyl, —C(=O)—N($C_{1-5}$-alkyl)$_2$, —S(=O)—$C_{1-5}$-alkyl, —S(=O)-phenyl, —S(=O)$_2$—$C_{1-5}$-alkyl, —S(=O)$_2$-phenyl, —S(=O)$_2$—$NH_2$ and —$SO_3H$, whereby the phenyl residues can be substituted with 1, 2, 3, 4 or 5 substituents mutually independently selected from the group comprising F, Cl, Br, I, —CN, —$CF_3$, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl and tert-butyl;

the above-mentioned cycloalkyl residues in each case have 3, 4, 5, 6, 7, 8 or 9 carbon atoms as ring members;

the above-mentioned cycloalkenyl residues in each case have 3, 4, 5, 6, 7, 8 or 9 carbon atoms as ring members;

the above-mentioned heterocycloalkyl residues are in each case 3-, 4-, 5-, 6-, 7-, 8- or 9-membered;

the above-mentioned heterocycloalkenyl residues are in each case 4-, 5-, 6-, 7-, 8- or 9-membered;

the above-mentioned heterocycloalkyl residues and heterocycloalkenyl residues in each case have optionally 1, 2 or 3 heteroatom(s) mutually independently selected from the group comprising oxygen, sulphur and nitrogen (NH) as the ring member(s);

the above-mentioned cycloalkyl residues, heterocycloalkyl residues, cycloalkenyl residues or heterocycloalkenyl residues can in each case be substituted with optionally 1, 2, 3, 4 or 5 substituents mutually independently selected from the group comprising F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —S—CH$_2$-phenyl, —S—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl, —C(=O)—CF$_3$, —S(=O)$_2$—C$_{1-5}$-alkyl, —S(=O)—C$_{1-5}$-alkyl, —S(=O)$_2$-phenyl, oxo(=O), thioxo(=S), —N(C$_{1-5}$-alkyl)$_2$, —N(H)(C$_{1-5}$-alkyl), —NO$_2$, —S—CF$_3$, —C(=O)—OH, —NH—C(=O)—C$_{1-5}$-alkyl, —C(=O)—H, —C(=O)—C$_{1-5}$-alkyl, —C(=O)—NH$_2$, —C(=O)—N(C$_{1-5}$-alkyl)$_2$, —C(=O)—N(H)(C$_{1-5}$-alkyl) and phenyl, whereby the phenyl residues can respectively be unsubstituted or substituted with 1, 2, 3, 4 or 5 substituents mutually independently selected from the group comprising F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl and —C(=O)—CF$_3$, whereby the above-mentioned phenyl residues can preferably be substituted with 1, 2, 3, 4 or 5 substituents mutually independently selected from the group comprising F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl;

the above-mentioned alkylene residues are in each case branched or straight-chained and have 1, 2, 3, 4, 5, 6, 7, 8, 9, 10, 11 or 12 carbon atoms as chain members;

the above-mentioned alkenylene residues are in each case branched or straight-chained and have 2, 3, 4, 5, 6, 7, 8, 9, 10, 11 or 12 carbon atoms as chain members;

the above-mentioned alkynylene residues are in each case branched or straight-chained and have 2, 3, 4, 5, 6, 7, 8, 9, 10, 11 or 12 carbon atoms as chain members;

the above-mentioned heteroalkylene residues and heteroalkenylene residues are in each case 2-, 3-, 4-, 5-, 6-, 7-, 8-, 9-, 10-, 11- or 12-membered;

the above-mentioned heteroalkylene and heteroalkenylene groups have in each case optionally 1, 2 or 3 heteroatom(s) mutually independently selected from the group comprising oxygen, sulphur and nitrogen (NH) as the chain member(s);

the above-mentioned alkylene, alkenylene, alkynylene, heteroalkylene or heteroalkenylene group can in each case be unsubstituted or substituted with optionally 1, 2, 3, 4 or 5 substituents mutually independently selected from the group comprising phenyl, F, Cl, Br, I, —NO$_2$, —CN, —OH, —O-phenyl, —O—CH$_2$-phenyl, —SH, —S-phenyl, —S—CH$_2$-phenyl, NH$_2$, —N(C$_{1-5}$-alkyl)$_2$, —NH-phenyl, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, whereby the phenyl residues can be substituted with 1, 2, 3, 4 or 5 substituents mutually independently selected from the group comprising F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

the above-mentioned aryl residues are mono- or bicyclic and have 6, 10 or 14 carbon atoms;

the above-mentioned heteroaryl residues are mono-, bi- or tricyclic and 5-, 6-, 7-, 8-, 9-, 10-, 11-, 12-, 13- or 14-membered;

the above-mentioned 5- to 14-membered heteroaryl residues in each case have optionally 1, 2, 3, 4 or 5 heteroatom(s) mutually independently selected from the group comprising oxygen, sulphur and nitrogen (NH) as ring member(s);

and the above-mentioned aryl residues and heteroaryl residues can in each case be substituted with optionally 1, 2, 3, 4 or 5 substituents mutually independently selected from the group comprising F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, N(C$_{1-5}$-alkyl)$_2$, —C(=O)—O—C$_{1-5}$-alkyl, —C(=O)—O-phenyl, —C(=O)—H, —C(=O)—C$_{1-5}$-alkyl, —CH$_2$—O—C(=O)-phenyl, —O—C(=O)-phenyl, —O—C(=O)—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, —C(=O)—N(C$_{1-5}$-alkyl)(phenyl), —C(=O)—NH-phenyl, cyclopropyl, cyclobutyl, cyclopentyl, cyclohexyl, pyrazolyl, phenyl, furyl (furanyl), thiazolyl, thiadiazolyl, thiophenyl (thienyl), benzyl and phenethyl, whereby the cyclic substituents or the cyclic residues of these substituents themselves can be substituted with optionally 1, 2, 3, 4 or 5 substituents mutually independently selected from the group comprising F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are particularly preferred, in which A denotes a residue selected from the group comprising

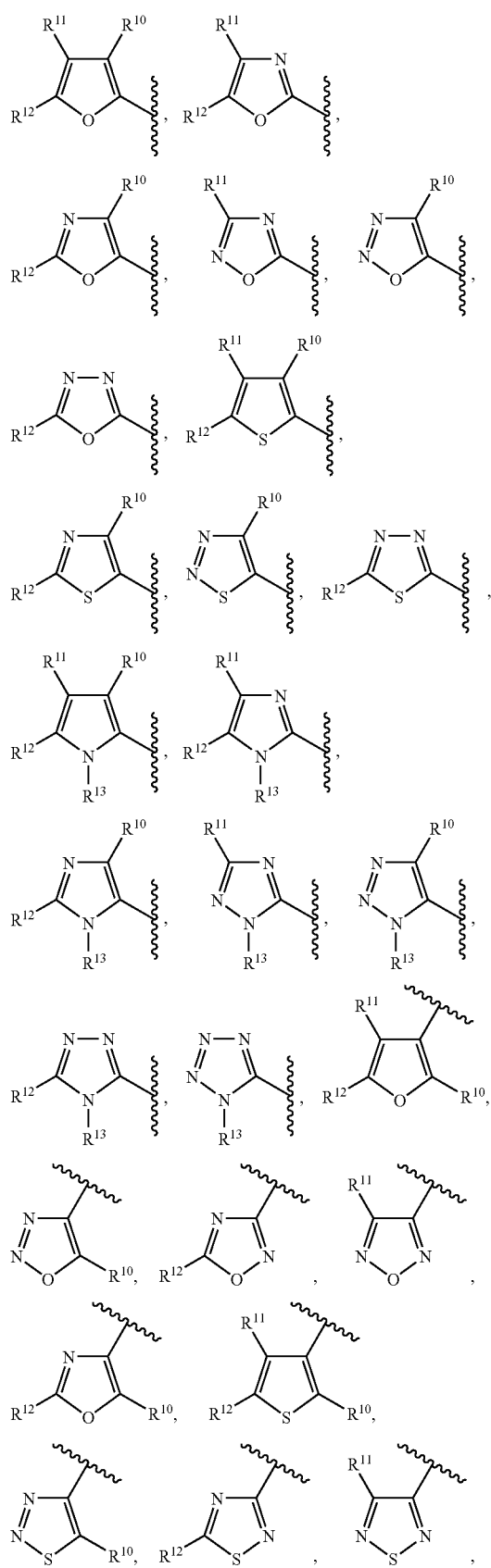
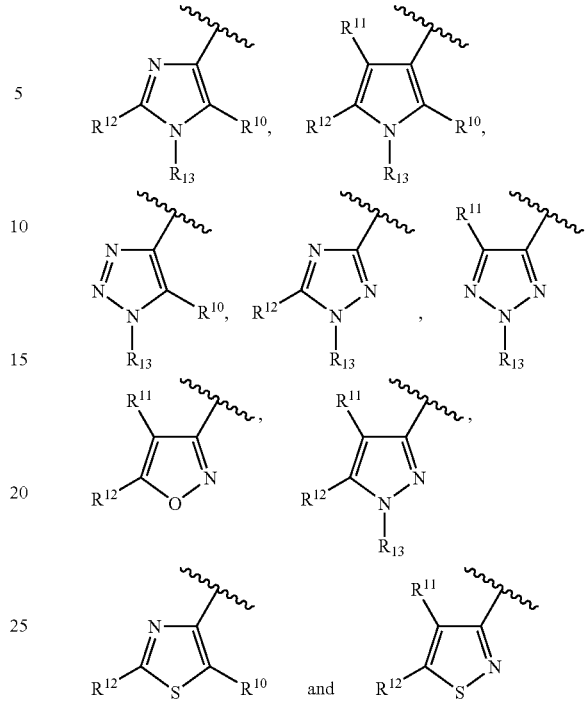

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are likewise particularly preferred, in which $R^1$ and $R^8$, mutually independently, in each case denote H; —C(=O)—$R^{28}$; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; $C_{1-6}$-alkyl, which is unsubstituted or substituted with optionally 1, 2, 3, 4 or 5 substituents mutually independently selected from the group comprising F, Cl, Br, I, —$NO_2$, —CN, —OH, —SH and —$NH_2$; $C_{3-8}$-cycloalkyl, which is unsubstituted or substituted with optionally 1, 2, 3, 4 or 5 substituents mutually independently selected from the group comprising F, Cl, Br, I, —$NO_2$, —CN, —OH, —SH and —$NH_2$; or a phenyl residue, which can be bound in each case via a $C_{1-3}$-alkylene-, $C_{2-3}$-alkenylene- or $C_{2-3}$-alkynylene group and/or is unsubstituted or substituted with 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, —O—$CH_3$, —O—$C_2H_5$ and —O—$C_3H_7$;

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are furthermore particularly preferred, in which $R^2$, $R^3, R^4, R^5, R^6, R^7, R^{14}, R^{15}, R^{16}, R^{17}, R^{18}, R^{19}, R^{20}, R^{21}, R^{22}, R^{23}, R^{24}, R^{25}, R^{26}$ and $R^{27}$, mutually independently, in each case denote H; F; Cl; Br; I; —NO$_2$; —CN; —NH$_2$; —OH; —SH; —C(═O)—OH; —C(═O)—R$^{28}$; —C(═O)—O—R$^{29}$; —NH—R$^{35}$; —NR$^{36}$R$^{37}$; —O—R$^{42}$; —S—R$^{43}$; C$_{1-6}$-alkyl, which is unsubstituted or substituted with optionally 1, 2, 3, 4 or 5 substituents mutually independently selected from the group comprising F, Cl, Br, I, —NO$_2$, —CN, —OH, —SH and —NH$_2$; C$_{3-7}$-cycloalkyl, C$_{5-6}$-cycloalkenyl, 5- to 7-membered heterocycloalkyl or 5- to 7-membered heterocycloalkenyl, which can be bound in each case via a C$_{1-3}$-alkylene-, C$_{2-3}$-alkenylene -or C$_{2-3}$-alkynylene group and/or unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denote a residue selected from the group comprising phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, chinolinyl, isochinolinyl and chinazolinyl, which can be bound in each case via a C$_{1-3}$-alkylene, C$_{2-3}$-alkenylene or C$_{2-3}$ alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

or $R^2$ and $R^3$ or $R^4$ and $R^5$ or $R^6$ and $R^7$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$, mutually independently, jointly in each case denote a residue selected from the group comprising an oxo group (═O) and a thioxo group (═S);

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are likewise particularly preferred, in which R$^1$ and R$^8$ jointly with the —N—CR$^2$R$^3$—(CR$^4$R$^5$)$_b$—(CR$^6$R$^7$)$_c$ group joining them together form a residue selected from the group comprising

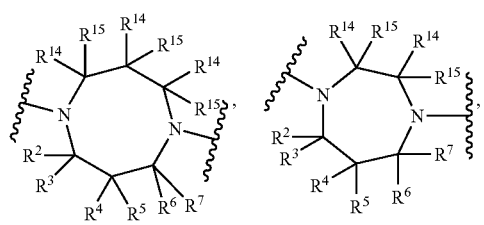

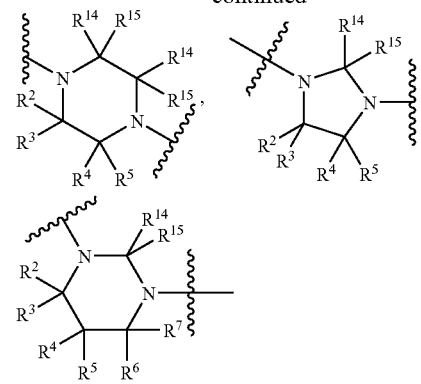

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are furthermore particularly preferred, in which R$^1$ and R$^2$ together with the —N—CR$^3$ group joining them together form a residue selected from the group comprising

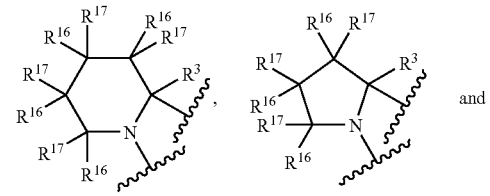

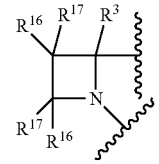

whereby, in this case, b denotes and c denotes 0;

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are likewise particularly preferred, in which R$^1$ and R$^4$ together with the —N—CR$^2$R$^3$—CR$^5$ group joining them together form a residue selected from the group comprising

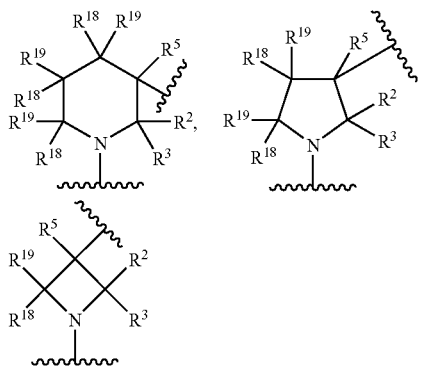

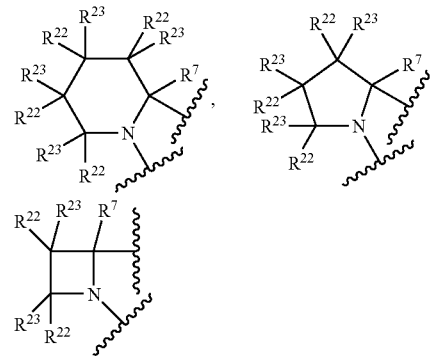

whereby, in this case, c denotes 0;

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are furthermore particularly preferred, in which $R^1$ and $R^6$ together with the —N—$CR^2R^3$—$CR^4R^5$—$CR^7$ group joining them together form a residue selected from the group comprising whereby, in this case, b denotes 1 and a denotes 0;

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are furthermore particularly preferred, in which $R^4$ and $R^8$ together with the —N—$CR^6R^7$—$CR^5$ group joining them together form a residue selected from the group comprising

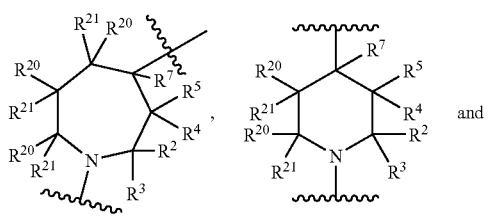

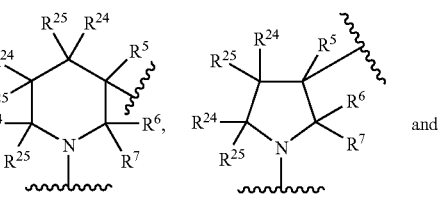

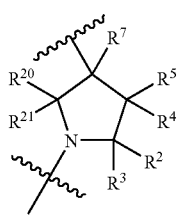

whereby, in this case, a denotes 0;

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are likewise particularly preferred, in which $R^6$ and $R^8$ together with the —N—$CR^7$ group joining them together form a residue selected from the group comprising Propiolic acid amides of the above-mentioned general formula I are likewise particularly preferred, in which $R^2$ and $R^8$ together with the —N—$CR^6R^7$—$CR^4R^5$—$CR^3$ group joining them together form a residue selected from the group comprising

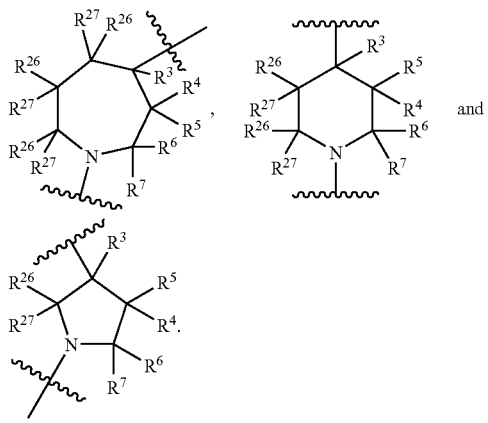

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are furthermore particularly preferred, in which $R^9$ denotes a residue selected from the group comprising phenyl, naphthyl, anthracenyl, furyl, thienyl, pyrazolyl, pyrazinyl, pyrimidinyl, pyridazinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, chinolinyl, isochinolinyl and chinazolinyl, which is in each case unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, ethenyl, allyl, ethynyl, propynyl, cyclopropyl, cyclobutyl, cyclopentyl, cyclohexyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H, —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are likewise particularly preferred, in which $R^{10}$, $R^{11}$ and $R^{12}$, mutually independently, in each case denote H; F; Cl; Br; I; —NO$_2$; —CN; —NH$_2$; —OH; —SH; —C(=O)—OH; —C(=O)—H; —NH—C(=O)—H; —C(=O)—R$^{28}$; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; —NH—R$^{35}$; —NR$^{36}$R$^{37}$; —O—C(=O)—R$^{38}$; —NH—C(=O)—R$^{39}$; —NR$^{40}$—C(=O)—R$^{41}$; —O—R$^{42}$; —S—R$^{43}$—NH—C(=O)—NH—R$^{44}$; —NH—C(=S)—NH—R$^{45}$; —NH—S(=O)$_2$—R$^{46}$; —NR$^{47}$—S(=O)$_2$—R$^{48}$; C$_{1-6}$-alkyl, which is unsubstituted or substituted with optionally 1, 2, 3, 4 or 5 substituents mutually independently selected from the group comprising F, Cl, Br, I, —NO$_2$, —CN, —OH, —SH and —NH$_2$; C$_{2-6}$-alkenyl; C$_{2-6}$-alkynyl; C$_{3-7}$-cycloalkyl, C$_{5-6}$-cycloalkenyl, 5- to 7-membered heterocycloalkyl or 5- to 7-membered heterocycloalkenyl, which can in each case be bound via a C$_{1-3}$-alkylene, C$_{2-3}$-alkenylene or C$_{2-3}$-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denote a residue selected from the group comprising phenyl, naphthyl, anthracenyl, thienyl, furyl, pyridinyl, thiazolyl, thiadiazolyl, oxazolyl, oxadiazolyl and isoxazolyl, which in each case can be bound via a C$_{1-3}$-alkylene-, C$_{2-3}$-alkenylene- or C$_{2-3}$-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$;

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are furthermore particularly preferred, in which $R^{13}$ denotes H; —C(=O)—R$^{28}$; —C(=O)—H; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; C$_{1-6}$-alkyl, which is unsubstituted or substituted with optionally 1, 2, 3, 4 or 5 substituents mutually independently selected from the group comprising F, Cl, Br, I, —NO$_2$, —CN, —OH, —SH and —NH$_2$; C$_{3-7}$-cycloalkyl, C$_{5-6}$-cycloalkenyl, 5- to 7-membered heterocycloalkyl or 5- to 7-membered heterocycloalkenyl, which in each case can be bound via a C$_{1-3}$-alkylene, C$_{2-3}$-alkenylene or C$_{2-3}$-alkynylene group and/or is unsubstituted or is substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denotes a residue selected from the group comprising phenyl, naphthyl, anthracenyl, thienyl, furyl, pyridinyl, thiazolyl, thiadiazolyl, oxazolyl, oxadiazolyl and isoxazolyl, which in each case can be bound via a $C_{1-3}$-alkylene, $C_{2-3}$-alkenylene or $C_{2-3}$-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$;

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Propiolic acid amides of the above-mentioned general formula I are likewise particularly preferred, in which $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$, mutually independently, in each case denote $C_{1-6}$-alkyl, which is unsubstituted or substituted with optionally 1, 2, 3, 4 or 5 substituents mutually independently selected from the group comprising F, Cl, Br, I, —NO$_2$, —CN, —OH, —SH and —NH$_2$; $C_{3-7}$-cycloalkyl, $C_{5-6}$-cycloalkenyl, 5- to 7-membered heterocycloalkyl or 5- to 7-membered heterocycloalkenyl, which can in each case be bound via a $C_{1-3}$-alkylene, $C_{2-3}$-alkenylene or $C_{2-3}$-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denote a residue selected from the group comprising phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, chinolinyl, isochinolinyl and chinazolinyl, which in each case can be bound via a $C_{1-3}$-alkylene, $C_{2-3}$-alkenylene or $C_{2-3}$-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —NH—S(=O)$_2$—CH$_3$, —C(=O)—OH, —C(=O)—CH$_3$, —C(=O)—C$_2$H$_5$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$ and —C(=O)—O—C$_2$H$_5$;

and in each case the remaining residues have the above-mentioned meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates Substituted propiolic acid amides of the above-mentioned formula I are particularly preferred, in which a, b and c, mutually independently, in each case denote 0 or 1, whereby the sum of a, b and c is equal to 1, 2 or 3;

A denotes a residue selected from the group comprising

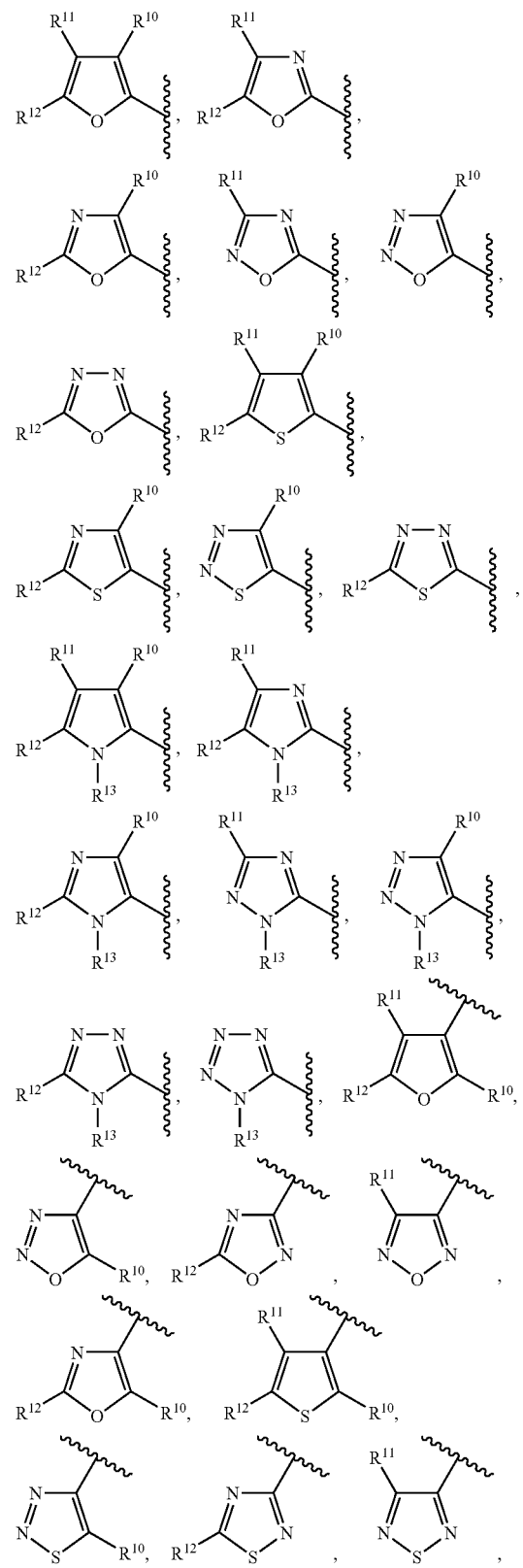

-continued

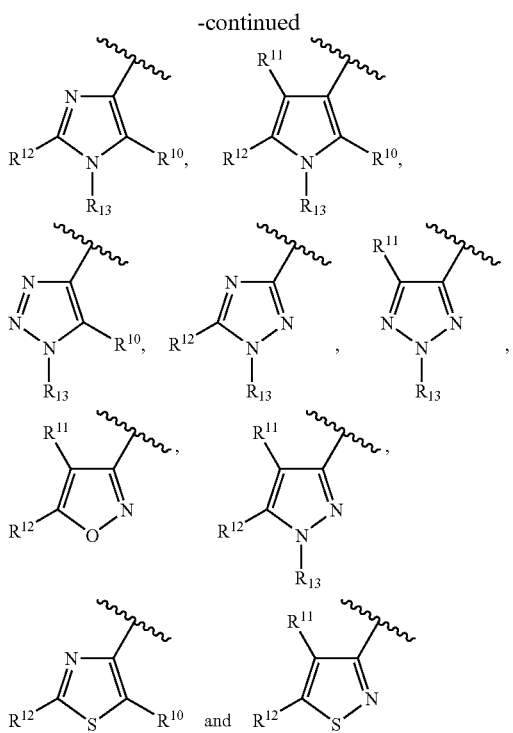

R$^1$ and R$^8$, mutually independently, in each case denote H; —C(=O)—R$^{28}$; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; C$_{1-6}$-alkyl, which is unsubstituted or substituted with optionally 1, 2, 3, 4 or 5 substituents mutually independently selected from the group comprising F, Cl, Br, I, —NO$_2$, —CN, —OH, —SH and —NH$_2$;

C$_{3-8}$-cycloalkyl, which is unsubstituted or substituted with optionally 1, 2, 3, 4 or 5 substituents mutually independently selected from the group comprising F, Cl, Br, I, —NO$_2$, —CN, —OH, —SH and —NH$_2$;

or a phenyl residue, which in each case can be bound via a C$_{1-3}$-alkylene, C$_{2-3}$-alkenylene or C$_{2-3}$-alkynylene group and/or is unsubstituted or substituted with 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

R$^2$, R$^3$, R$^4$, R$^5$, R$^6$, R$^7$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$ and R$^{27}$, mutually independently, in each case denote H; F; Cl; Br; I; —NO$_2$; —CN; —NH$_2$; —OH; —SH; —C(=O)—OH; —C(=O)—R$^{28}$; —C(=O)—O—R$^{29}$; —NH—R$^{35}$; —NR$^{36}$R$^{37}$; —O—R$^{42}$; —S—R$^{43}$; C$_{1-6}$-alkyl, which is unsubstituted or substituted with optionally 1, 2, 3, 4 or 5 substituents mutually independently selected from the group comprising F, Cl, Br, I, —NO$_2$, —CN, —OH, —SH and —NH$_2$;

C$_{3-7}$-cycloalkyl, C$_{5-6}$-cycloalkenyl, 5- to 7-membered heterocycloalkyl or 5- to 7-membered heterocycloalkenyl, which in each case can be bound via a C$_{1-3}$-alkylene, C$_{2-3}$-alkenylene or C$_{2-3}$-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or a residue selected from the group comprising phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, chinolinyl, isochinolinyl and chinazolinyl, which in each case can be bound via a C$_{1-3}$-alkylene, C$_{2-3}$-alkenylene or C$_{2-3}$-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

or R$^2$ and R$^3$ or R$^4$ and R$^5$ or R$^6$ and R$^7$ or R$^{14}$ and R$^{15}$ or R$^{16}$ and R$^{17}$ or R$^{18}$ and R$^{19}$ or R$^{20}$ and R$^{21}$ or R$^{22}$ and R$^{23}$ or R$^{24}$ and R$^{25}$ or R$^{26}$ and R$^{27}$, mutually independently, jointly in each case denote a residue selected from the group comprising an oxo group (=O) and a thioxo group (=S);

or R$^1$ and R$^8$ together with the —(CR$^4$R$^5$)$_b$—(CR$^6$R$^7$)$_c$ group joining them together form a residue selected from the group comprising

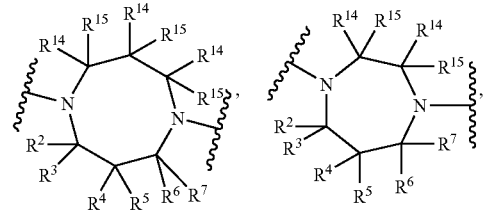

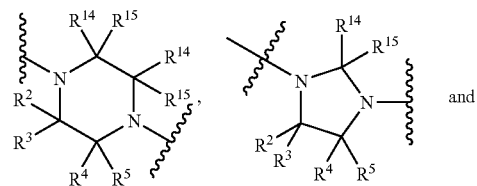

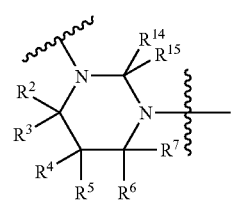

or R$^1$ and R$^2$ together with the —N—CR$^3$ group joining them together form a residue selected from the group comprising

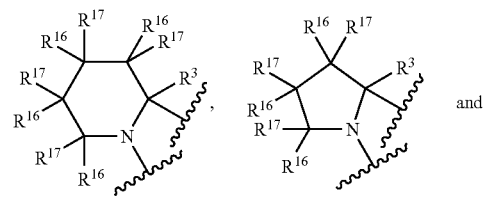

-continued

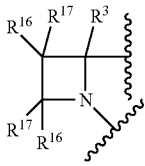

whereby, in this case, b denotes 1 and c denotes 0;

or $R^1$ and $R^4$ together with the $-N-CR^2R^3-CR^5$ group joining them together form a residue selected from the group comprising

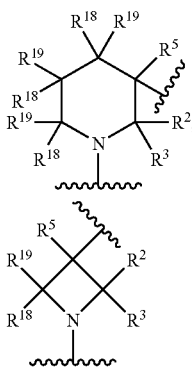 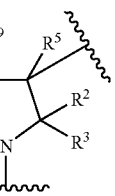 and

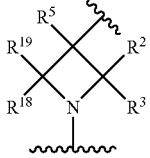

whereby, in this case, c denotes 0;

$R^1$ and $R^6$ together with the $-N-CR^2R^3-CR^4R^5-CR^7$ group joining them together form a residue selected from the group comprising

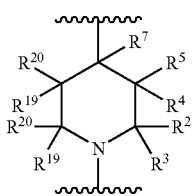 and 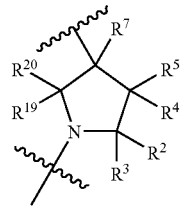

$R^6$ and $R^8$ together with the $-N-CR^7$ group joining them together form a residue selected from the group comprising

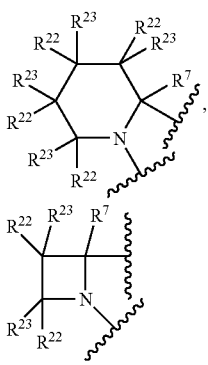 and 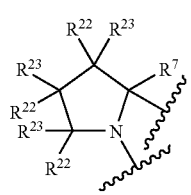

whereby, in this case, b denotes 1 and a denotes 0;

or $R^4$ and $R^8$ together with the $-N-CR^6R^7-CR^5$ group joining them together form a residue selected from the group comprising

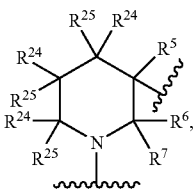 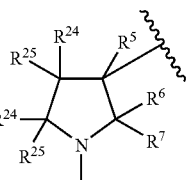 and

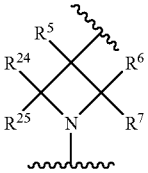

whereby, in this case, a denotes 0;

or $R^2$ and $R^8$ together with the $-N-CR^6R^7-CR^4R^5-CR^3$ group joining them together form a residue selected from the group comprising

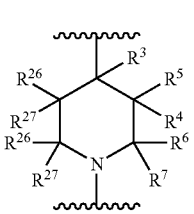 and 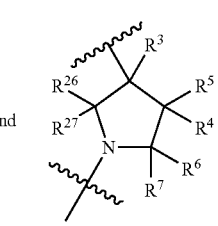

$R^9$ denotes a residue selected from the group comprising phenyl, naphthyl, anthracenyl, furyl, thienyl, pyrazolyl, pyrazinyl, pyrimidinyl, pyridazinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, chinolinyl, isochinolinyl and chinazolinyl, which in each case is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, ethenyl, allyl, ethynyl, propynyl, cyclopropyl, cyclobutyl, cyclopentyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

$R^{10}$, $R^{11}$ and $R^{12}$, mutually independently, in each case denote H; F; Cl; Br; I; —NO$_2$; —CN; —NH$_2$; —OH; —SH; —C(=O)—OH; —C(=O)—H; —NH—C(=O)—H; —C(=O)—R$^{28}$; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; —NH—R$^{35}$; —NR$^{36}$R$^{37}$; —O—C(=O)—R$^{38}$; —NH—C(=O)—R$^{39}$;

—NR⁴⁰—C(=O)—R⁴¹; —O—R⁴²; —S—R⁴³—NH—C(=O)—NH—R⁴⁴; —NH—C(=S)—NH—R⁴⁵; —NH—S(=O)₂—R⁴⁶; —NR⁴⁷—S(=O)₂—R⁴⁸; C₁₋₆-alkyl, which is unsubstituted or substituted with optionally 1, 2, 3, 4 or 5 substituents mutually independently selected from the group comprising F, Cl, Br, I, —NO₂, —CN, —OH, —SH and —NH₂; C₂₋₆-alkenyl; C₂₋₆-alkynyl; C₃₋₇-cycloalkyl, C₅₋₆-cycloalkenyl, 5- to 7-membered heterocycloalkyl or 5- to 7-membered heterocycloalkenyl, which in each case can be bound via a C₁₋₃-alkylene, C₂₋₃-alkenylene or C₂₋₃-alkynylene group and/or is unsubstituted or is substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, oxo, thioxo, —O—CH₃, —O—C₂H₅, —O—C₃H₇, —NH₂, —N(CH₃)₂, —N(C₂H₅)₂, —NH—CH₃, —NH—C₂H₅, —NO₂, —CF₃, —O—CF₃, —S—CF₃, —SH, —S—CH₃ and —S—C₂H₅; or a residue selected from the group comprising phenyl, naphthyl, anthracenyl, thienyl, furyl, pyridinyl, thiazolyl, thiadiazolyl, oxazolyl, oxadiazolyl and isoxazolyl, which in each case can be bound via a C₁₋₃-alkylene, C₂₋₃-alkenylene or C₂₋₃-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, isobutyl, 2-butyl, tert-butyl, —OH, —SH, —NH₂, —C(=O)—OH, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —CF₃, —CHF₂, —CH₂F and —O—CF₃;

$R^{13}$ denotes H; —C(=O)—R²⁸; —C(=O)—H; —C(=O)—O—R²⁹; —C(=O)—NH₂; —C(=O)—NH—R³⁰; —C(=O)—NR³¹R³²; —S(=O)—R³³; —S(=O)₂—R³⁴; C₁₋₆-alkyl, which is unsubstituted or substituted with optionally 1, 2, 3, 4 or 5 substituents mutually independently selected from the group comprising F, Cl, Br, I, —NO₂, —CN, —OH, —SH and —NH₂; C₃₋₇-cycloalkyl, C₅₋₆-cycloalkenyl, 5- to 7-membered heterocycloalkyl or 5- to 7-membered heterocycloalkenyl, which in each case can be bound via a C₁₋₃-alkylene, C₂₋₃-alkenylene or C₂₋₃-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, oxo, thioxo, —O—CH₃, —O—C₂H₅, —O—C₃H₇, —NH₂, —N(CH₃)₂, —N(C₂H₅)₂, —NH—CH₃, —NH—C₂H₅, —NO₂, —CF₃, —O—CF₃, —S—CF₃, —SH, —S—CH₃ and —S—C₂H₅; or a residue selected from the group comprising phenyl, naphthyl, anthracenyl, thienyl, furyl, pyridinyl, thiazolyl, thiadiazolyl, oxazolyl, oxadiazolyl and isoxazolyl, which in each case can be bound via a C₁₋₃-alkylene, C₂₋₃-alkenylene or C₂₋₃-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, isobutyl, 2-butyl, tert-butyl, —OH, —SH, —NH₂, —C(=O)—OH, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —CF₃, —CHF₂, —CH₂F and —O—CF₃;

and $R^{28}, R^{29}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}$ and $R^{48}$, mutually independently, in each case denote C₁₋₆-alkyl, which is unsubstituted or substituted with optionally 1, 2, 3, 4 or 5 substituents mutually independently selected from the group comprising F, Cl, Br, I, —NO₂, —CN, —OH, —SH and —NH₂; C₃₋₇-cycloalkyl, C₅₋₆-cycloalkenyl, 5- to 7-membered heterocycloalkyl or 5- to 7-membered heterocycloalkenyl, which can in each case be bound via a C₁₋₃-alkylene, C₂₋₃-alkenylene or C₂₋₃-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, oxo, thioxo, —O—CH₃, —O—C₂H₅, —O—C₃H₇, —NH₂, —N(CH₃)₂, —N(C₂H₅)₂, —NH—CH₃, —NH—C₂H₅, —NO₂, —CF₃, —O—CF₃, —S—CF₃, —SH, —S—CH₃ and —S—C₂H₅; or a residue selected from the group comprising phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, chinolinyl, isochinolinyl and chinazolinyl, which in each case can be bound via a C₁₋₃-alkylene, C₂₋₃-alkenylene or C₂₋₃-alkynylene group and/or is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, —OH, —O—CH₃, —O—C₂H₅, —O—C₃H₇, —NH₂, —N(CH₃)₂, —N(C₂H₅)₂, —NH—CH₃, —NH—C₂H₅, —NO₂, —CF₃, —O—CF₃, —S—CF₃, —SH, —NH—S(=O)₂—CH₃, —C(=O)—OH, —C(=O)—CH₃, —C(=O)—C₂H₅, —C(=O)—N(CH₃)₂, —C(=O)—NH—CH₃, —NH—C(=O)—CH₃, —NH—C(=O)—C₂H₅, —C(=O)—O—CH₃ and —C(=O)—O—C₂H₅;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted propiolic acid amides of the above-mentioned general formula I are likewise particularly preferred, in which a, b and c, mutually independently, in each case denote 0 or 1, whereby the sum of a, b and c is equal to 1, 2 or 3;

A denotes a residue selected from the group comprising

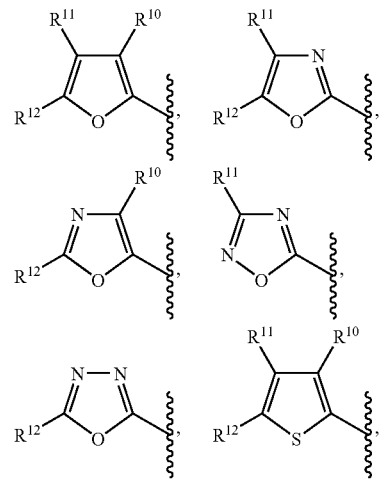

-continued

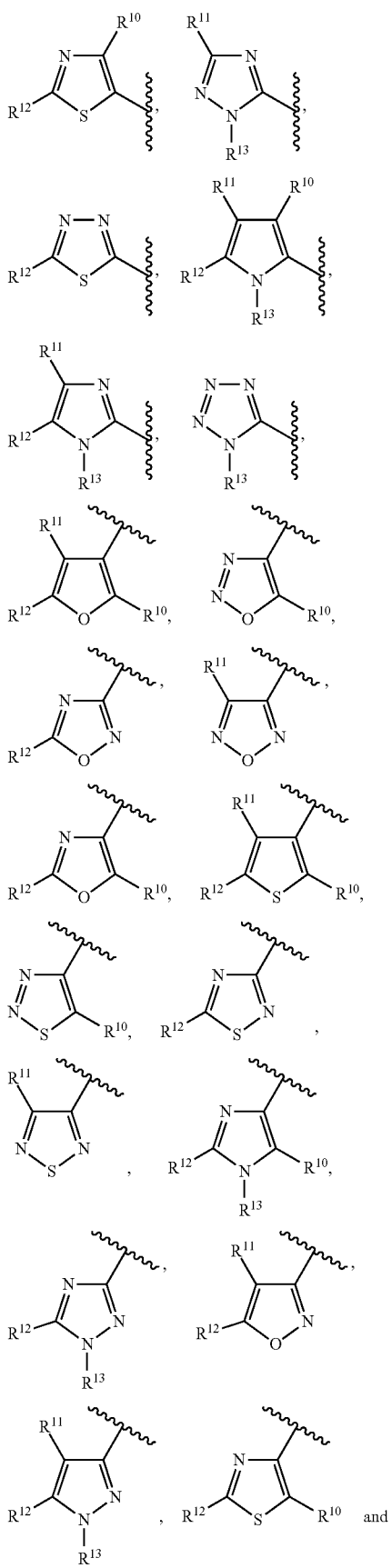

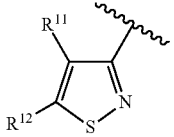

$R^1$ and $R^8$, mutually independently, in each case denote H; —C(=O)—$R^{28}$; —C(=O)—O—$R^{29}$; S(=O)—$R^{33}$; —S(=O)$_2$—$R^{34}$; an alkyl residue selected from the group comprising methyl, ethyl, n-propyl, isopropyl, n-butyl, 2-butyl, isobutyl, tert-butyl, n-pentyl and n-hexyl; a cycloalkyl residue selected from the group comprising cyclopropyl, cyclobutyl, cyclopentyl and cyclohexyl; or a benzyl or phenethyl residue, which is unsubstituted or is substituted with 1, 2, 3, 4 or 5 substituents mutually independently selected from the group comprising F, Cl, Br, methyl, ethyl, n-propyl, isopropyl, n-butyl, 2-butyl, isobutyl, tert-butyl, —OH, —O—$CH_3$, —O—$C_2H_5$ and —O—$C_3H_7$;

$R^2, R^3, R^4, R^5, R^6, R^7, R^{14}, R^{15}, R^{16}, R^{17}, R^{18}, R^{19}, R^{20}, R^{21}, R^{22}, R^{23}, R^{24}, R^{25}, R^{26}$ and $R^{27}$, mutually independently, in each case denote H; F; Cl; Br; I; —$NH_2$; —OH; —SH; —CN; —$NO_2$; —$CF_3$; —NH—$R^{35}$; —$NR^{36}R^{37}$; —O—$R^{42}$; —S—$R^{43}$; an alkyl residue selected from the group comprising methyl, ethyl, n-propyl, isopropyl, n-butyl, 2-butyl, isobutyl, tert-butyl, n-pentyl and n-hexyl; or a residue selected from the group comprising cyclopropyl, cyclobutyl, cyclopentyl and cyclohexyl;

or $R^2$ and $R^3$ or $R^4$ and $R^5$ or $R^6$ and $R^7$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$, mutually independently, jointly in each case denote a residue selected from the group comprising an oxo group (=O) and a thioxo group (=S);

or $R^1$ and $R^8$ together with the —N—$CR^2R^3$—$(CR^4R^5)_b$—$(CR^6R^7)_c$ group joining them together form a residue selected from the group comprising

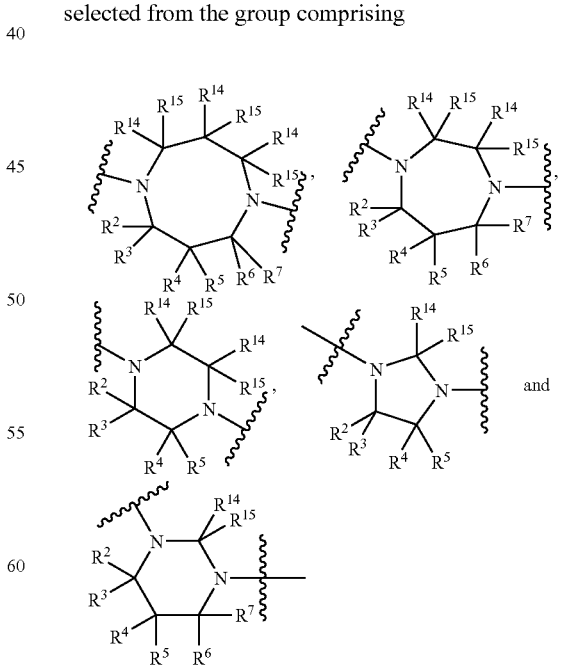

or $R^1$ and $R^2$ together with the —N—$CR^3$ group joining them together form a residue selected from the group comprising

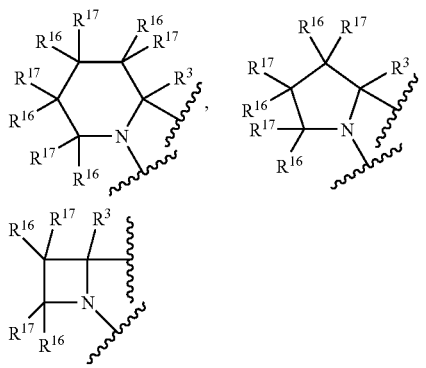

whereby, in this case, b denotes 1 and c denotes 0;
or R¹ and R⁴ together with the —N—CR²R³—CR⁵ group joining them together form a residue selected from the group comprising

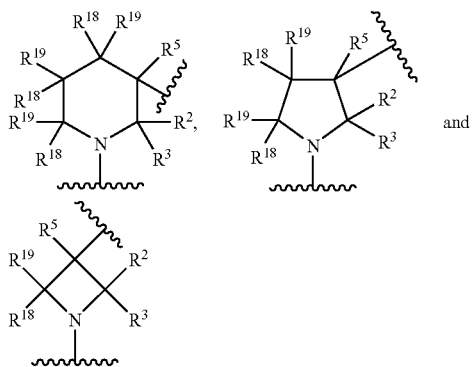

whereby, in this case, c denotes 0;
R¹ and R⁶ together with the —N—CR²R³—CR⁴R⁵—CR⁷ group joining them together form a residue selected from the group comprising

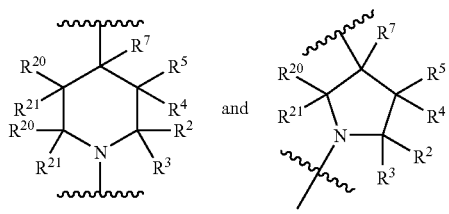

or R⁶ and R⁸ together with the —N—CR⁷ group joining them together form a residue selected from the group comprising

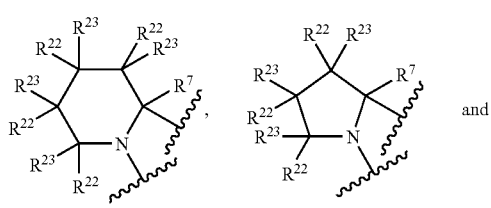

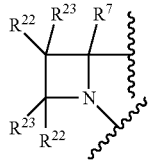

-continued whereby, in this case, b denotes 1 and a denotes 0;
or R⁴ and R⁸ together with the —N—CR⁶R⁷—CR⁵ group joining them together form a residue selected from the group comprising

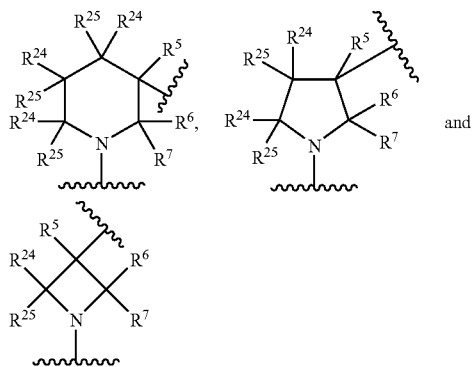

whereby, in this case, a denotes 0;
or R² and R⁸ together with the —N—CR⁶R⁷—CR⁴R⁵—CR³ group joining them together form a residue selected from the group comprising R⁹ denotes a residue selected from the group comprising phenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl and imidazolyl, which in each case is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, ethenyl, allyl, ethynyl, propynyl, cyclopropyl, cyclobutyl, —C≡C—Si(CH₃)₃, —C≡C—Si(C₂H₅)₃, —CH₂—O—CH₃, —CH₂—O—C₂H₅, —OH, —O—CH₃, —O—C₂H₅, —O—C₃H₇, —S—CH₃, —S—C₂H₅, —S(=O)—CH₃, —S(=O)₂—CH₃, —S(=O)—C₂H₅, —S(=O)₂—C₂H₅, —NH₂, —N(CH₃)₂, —N(C₂H₅)₂, —NH—CH₃, —NH—C₂H₅, —NO₂, —CF₃, —CH₂F, —CHF₂, —O—CF₃, —S—CF₃, —SH, —NH—S(=O)₂—CH₃, —C(=O)—OH, —C(=O)—H; —C(=O)—CH₃, —C(=O)—C₂H₅, —C(=O)—NH₂, —C(=O)—N(CH₃)₂, —C(=O)—NH—CH₃, —NH—C(=O)—CH₃, —NH—C(=O)—C₂H₅, —C(=O)—O—CH₃, —C(=O)—O—C₂H₅, —C(=O)—O—C(CH₃)₃ and phenyl;

$R^{10}$, $R^{11}$ and $R^{12}$, mutually independently, in each case denote H; F; Cl; Br; I; —$CF_3$; —$NO_2$; —CN; —C(=O)—OH; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; —O—$R^{42}$; —S—$R^{43}$; an alkyl residue selected from the group comprising methyl, ethyl, n-propyl, isopropyl, n-butyl, 2-butyl, isobutyl and tert-butyl; a residue selected from the group comprising ethenyl, ethynyl, allyl and propynyl; a residue selected from the group comprising cyclopropyl, cyclobutyl and cyclopentyl; or a residue selected from the group comprising phenyl, benzyl, phenethyl, oxadiazolyl, 2-pyridyl, 3-pyridyl, 4-pyridyl, 2-thienyl, 3-thienyl, 2-furyl and 3-furyl, which in each case is unsubstituted or substituted with optionally 1, 2, 3, 4 or 5 substituents mutually independently selected from the group comprising F, Cl, Br, methyl, ethyl, n-propyl, isopropyl, n-butyl, 2-butyl, isobutyl, tert-butyl, —OH, —O—$CH_3$, —O—$C_2H_5$ and —O—$C_3H_7$;

$R^{13}$ denotes H; —C(=O)—$R^{28}$; —C(=O)—H; —C(=O)—O—$R^{29}$; —S(=O)—$R^{33}$; —S(=O)$_2$—$R^{34}$; an alkyl residue selected from the group comprising methyl, ethyl, n-propyl, isopropyl, n-butyl, 2-butyl, isobutyl and tert-butyl; a residue selected from the group comprising cyclopropyl, cyclobutyl, cyclopentyl and cyclohexyl; or a residue selected from the group comprising phenyl, benzyl, phenethyl, oxadiazolyl, 2-pyridyl, 3-pyridyl, 4-pyridyl, 2-thienyl, 3-thienyl, 2-furyl and 3-furyl, which in each case can be bound via a $C_{1-3}$-alkylene group and/or is unsubstituted or substituted with optionally 1, 2, 3, 4 or 5 substituents mutually independently selected from the group comprising F, Cl, Br, methyl, ethyl, n-propyl, isopropyl, n-butyl, 2-butyl, isobutyl, tert-butyl, —OH, —O—$CH_3$, —O—$C_2H_5$ and —O—$C_3H_7$;

and $R^{28}$, $R^{29}$, $R^{30}$, $R^{31}$, $R^{32}$, $R^{33}$, $R^{34}$, $R^{35}$, $R^{36}$, $R^{37}$, $R^{42}$ and $R^{43}$, mutually independently, in each case denote an alkyl residue selected from the group comprising methyl, ethyl, n-propyl, isopropyl, n-butyl, 2-butyl, isobutyl, tert-butyl, n-pentyl and n-hexyl; —$CF_3$; —$C_2F_5$; —$CH_2$—$CF_3$; or a phenyl, benzyl or phenethyl residue, which is unsubstituted or substituted with 1, 2, 3, 4 or 5 substituents mutually independently selected from the group comprising F, Cl, Br, methyl, ethyl, n-propyl, isopropyl, n-butyl, 2-butyl, isobutyl, tert-butyl, —OH, —O—$CH_3$, —O—$C_2H_5$ and —O—$C_3H_7$;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted propiolic acid amides of the above-mentioned general formula I are very particularly preferred, in which a, b and c, mutually independently, in each case denote 0 or 1, wherein the sum of a, b and c is equal to 1, 2 or 3;

A denotes a residue selected from the group comprising

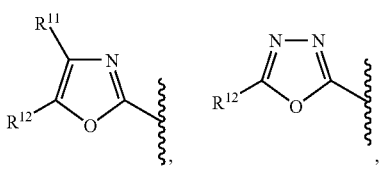

-continued

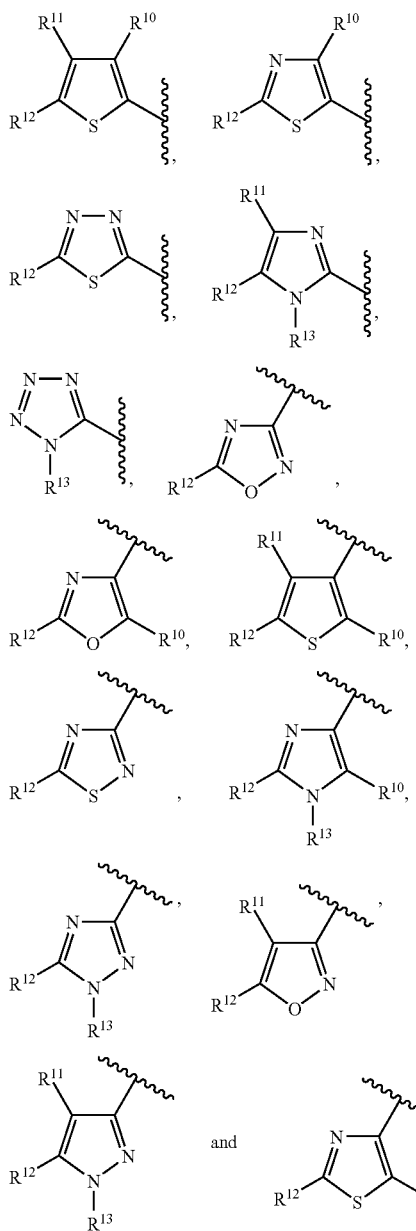

$R^1$ and $R^8$, mutually independently, in each case denote H; —C(=O)—$R^{28}$; —C(=O)—O—$R^{29}$; an alkyl residue selected from the group comprising methyl, ethyl, n-propyl, isopropyl, n-butyl, 2-butyl, isobutyl, tert-butyl, n-pentyl and n-hexyl; or a cyclopropyl residue;

$R^2$, $R^3$, $R^4$, $R^5$, $R^6$, $R^7$, $R^{14}$, $R^{15}$, $R^{16}$, $R^{17}$, $R^{18}$, $R^{19}$, $R^{22}$, $R^{23}$, $R^{24}$ and $R^{25}$, mutually independently, in each case denote H; F; Cl; Br; I; —$NH_2$; —OH; —SH; —CN; —$NO_2$; —$CF_3$; —NH—$R^{35}$; —$NR^{36}R^{37}$; —O—$R^{42}$; —S—$R^{43}$; an alkyl residue selected from the group comprising methyl, ethyl, n-propyl, isopropyl, n-butyl, 2-butyl, isobutyl, tert-butyl, n-pentyl and n-hexyl or a cyclopropyl residue;

or $R^1$ and $R^8$ together with the —N—$CR^2R^3$—$(CR^4R^5)_b$—$(CR^6R^7)_c$ group joining them together form a residue selected from the group comprising

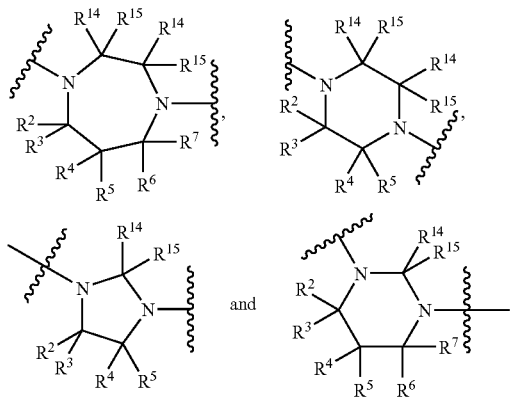

or $R^1$ and $R^2$ together with the —N—$CR^3$ group joining them together form a residue selected from the group comprising

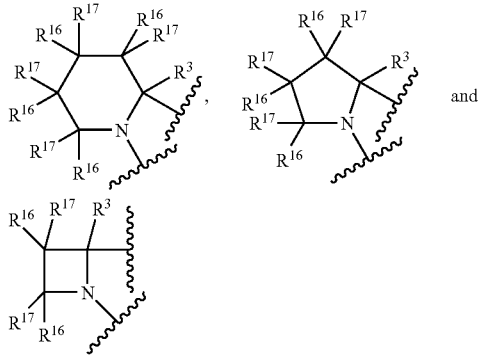

whereby, in this case, b denotes 1 and c denotes 0;
or $R^1$ and $R^4$ together with the —N—$CR^2R^3$—$CR^5$ group joining them together form a residue selected from the group comprising

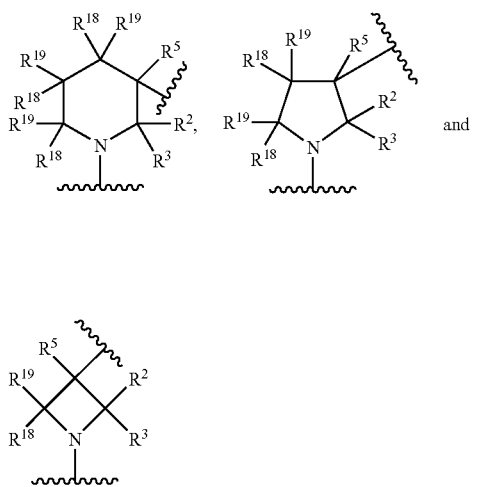

whereby, in this case, c denotes 0;
or $R^6$ and $R^8$ together with the —N—$CR^7$ group joining them together form a residue selected from the group comprising

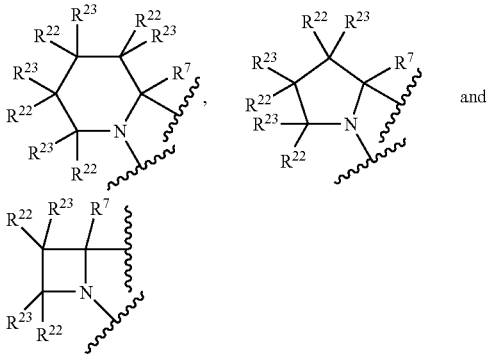

whereby, in this case, b denotes 1 and a denotes 0;
or $R^4$ and $R^8$ together with the —N—$CR^6R^7$—$CR^5$ group joining them together form a residue selected from the group comprising

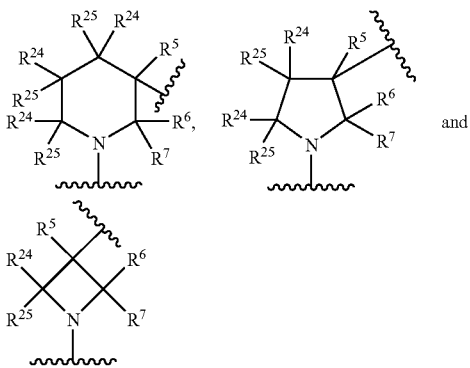

whereby, in this case, a denotes 0;
$R^9$ denotes a residue selected from the group comprising phenyl, thienyl, pyrazolyl, pyrazinyl, pyridazinyl, pyrimidinyl, pyridinyl, thiazolyl and thiadiazolyl, which in each case is unsubstituted or substituted with optionally 1, 2, 3, 4 or 5 substituents mutually independently selected from the group comprising F, Cl, Br, I, —CN, methyl, ethyl, n-propyl, isopropyl, n-butyl, 2-butyl, isobutyl, tert-butyl, ethenyl, allyl, ethynyl, propynyl, cyclopropyl, cyclobutyl, —C≡C—Si($CH_3$)$_3$, —C≡C—Si($C_2H_5$)$_3$, —$CH_2$—O—$CH_3$, —$CH_2$—O—$C_2H_5$, —OH, —O—$CH_3$, —O—$C_2H_5$, —O—$C_3H_7$, —S—$CH_3$, —S—$C_2H_5$, —S(═O)—$CH_3$, —S(═O)$_2$—$CH_3$, —S(═O)—$C_2H_5$, —S(═O)$_2$—$C_2H_5$, —$NH_2$, —N($CH_3$)$_2$, —N($C_2H_5$)$_2$, —NH—$CH_3$, —NH—$C_2H_5$, —$NO_2$, —$CF_3$, —$CH_2F$, —$CHF_2$, —O—$CF_3$, —S—$CF_3$, —SH, —NH—S(═O)$_2$—$CH_3$, —C(═O)—OH, —C(═O)—H; —C(═O)—$CH_3$, —C(═O)—$C_2H_5$, —C(═O)—$NH_2$, —C(═O)—N($CH_3$)$_2$, —C(═O)—NH—$CH_3$, —NH—C(═O)—$CH_3$, —NH—C(═O)—$C_2H_5$, —C(═O)—O—$CH_3$, —C(═O)—O—$C_2H_5$, —C(═O)—O—C($CH_3$)$_3$ and phenyl;

$R^{10}$, $R^{11}$ and $R^{12}$, mutually independently, in each case denote H; F; Cl; Br; I; —$CF_3$; —$NO_2$; —CN; —C(═O)—OH; —C(═O)—O—$R^{29}$; —C(═O)—$NH_2$; —O—$R^{42}$; —S—$R^{43}$; ethenyl; ethynyl; cyclopropyl or an alkyl residue selected from the group comprising methyl, ethyl, n-propyl, isopropyl, n-butyl, 2-butyl, isobutyl and tert-butyl;

$R^{13}$ denotes H; —C(=O)—$R^{28}$; —C(=O)—H; —C(=O)—O—$R^{29}$; —S(=O)—$R^{33}$; —S(=O)$_2$—$R^{34}$; cyclopropyl; cyclobutyl; or an alkyl residue selected from the group comprising methyl, ethyl, n-propyl, isopropyl, n-butyl, 2-butyl, isobutyl and tert-butyl;

and $R^{28}$, $R^{29}$, $R^{33}$, $R^{34}$, $R^{35}$, $R^{36}$, $R^{37}$, $R^{42}$ and $R^{43}$, mutually independently, in each case denote an alkyl residue selected from the group comprising methyl, ethyl, n-propyl, isopropyl, n-butyl, 2-butyl, isobutyl, tert-butyl, n-pentyl and n-hexyl; —CF$_3$; —C$_2$F$_5$; —CH$_2$—CF$_3$; or a phenyl, benzyl or phenethyl residue, which is unsubstituted or substituted with 1, 2, 3, 4 or 5 substituents mutually independently selected from the group comprising F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted propiolic acid amides of the above-mentioned general formula I are likewise very particularly preferred, in which a, b and c, mutually independently, in each case denote 0 or 1, whereby the sum of a, b and c is equal to 1 or 2;

A denotes a residue selected from the group comprising

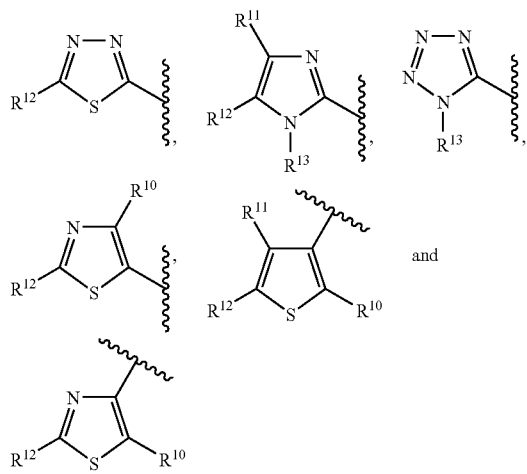

$R^1$ and $R^8$, mutually independently, in each case denote H; —C(=O)—$R^{28}$; an alkyl residue selected from the group comprising methyl, ethyl, n-propyl, isopropyl, n-butyl, 2-butyl, isobutyl, tert-butyl, n-pentyl and n-hexyl; or a cyclopropyl residue;

$R^2$, $R^3$, $R^4$, $R^5$, $R^6$, $R^7$, $R^{14}$, $R^{15}$, $R^{16}$, $R^{17}$, $R^{22}$, $R^{23}$, $R^{24}$ and $R^{25}$, mutually independently, in each case denote H; F; Cl; Br; I; —CN; —NO$_2$; —CF$_3$; —O—$R^{42}$; an alkyl residue selected from the group comprising methyl, ethyl, n-propyl, isopropyl, n-butyl, 2-butyl, isobutyl, tert-butyl, n-pentyl and n-hexyl or a cyclopropyl residue;

or $R^1$ and $R^8$ together with the —N—CR$^2$R$^3$—CR$^4$R$^5$ group joining them together form the following residue

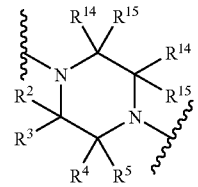

or $R^1$ and $R^2$ together with the —N—CR$^3$ group joining them together form a residue selected from the group comprising

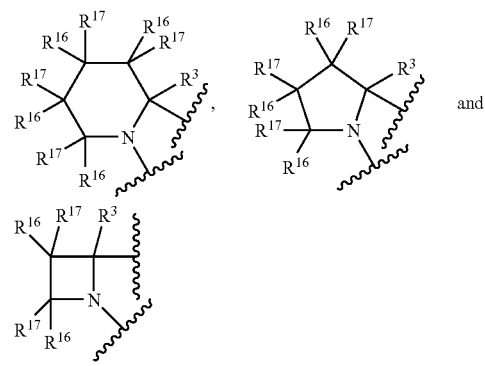

whereby, in this case, b denotes 1 and c denotes 0;

or $R^6$ and $R^8$ together with the —N—CR$^7$ group joining them together form a residue selected from the group comprising

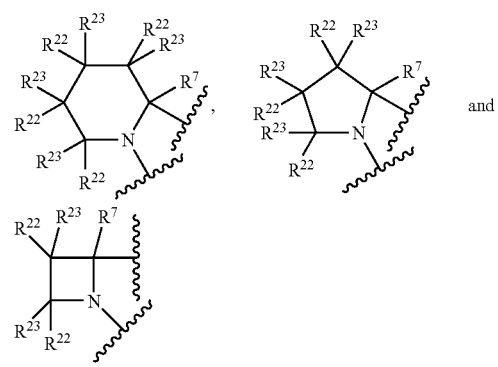

whereby, in this case, b denotes 1 and a denotes 0;

$R^9$ denotes a residue selected from the group comprising phenyl and thienyl, which in each case is unsubstituted or substituted with 1 or 2 substituents mutually independently selected from the group comprising F, Cl, Br, I, —CN, methyl, ethyl, n-propyl, isopropyl, n-butyl, 2-butyl, isobutyl, tert-butyl, ethenyl, ethynyl, cyclopropyl, —O—CH$_3$, —O—C$_2$H$_5$, —O—C$_3$H$_7$, —NO$_2$, —CF$_3$ and —O—CF$_3$;

$R^{10}$, $R^{11}$ and $R^{12}$, mutually independently, in each case denote H; F; Cl; Br; —CF$_3$; —NO$_2$; —CN; —O—$R^{42}$; an alkyl residue selected from the group comprising methyl, ethyl, n-propyl, isopropyl, isobutyl and tert-butyl; ethenyl; ethynyl or cyclopropyl;

$R^{13}$ denotes H; —C(=O)—H; —C(=O)—$R^{28}$; cyclopropyl; or an alkyl residue selected from the group comprising methyl, ethyl, n-propyl, isopropyl, n-butyl, 2-butyl, isobutyl and tert-butyl;

and $R^{28}$ and $R^{42}$, mutually independently, in each case denote an alkyl residue selected from the group comprising methyl, ethyl, n-propyl, isopropyl, n-butyl, 2-butyl, isobutyl and tert-butyl; or —$CF_3$;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted propiolic acid amides of the above-mentioned general formula I are furthermore very particularly preferred, in which a, b and c, mutually independently, in each case denote 0 or 1, whereby the sum of a, b and c is equal to 2;

A denotes a residue selected from the group comprising

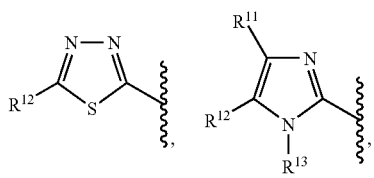

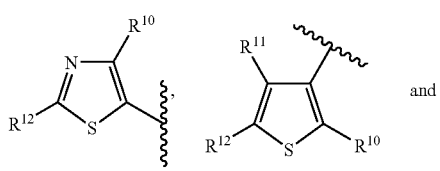 and

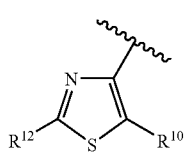

$R^1$ and $R^8$, mutually independently, in each case denote H, —C(=O)—$CH_3$, methyl, isopropyl or cyclopropyl;

$R^2$, $R^3$, $R^4$, $R^5$, $R^6$, $R^7$, $R^{14}$, $R^{15}$, $R^{16}$, $R^{17}$, $R^{22}$ and $R^{23}$, mutually independently, in each case denote H or an alkyl residue selected from the group comprising methyl, ethyl, n-propyl, isopropyl, n-butyl, 2-butyl, isobutyl, tert-butyl, n-pentyl and n-hexyl;

or $R^1$ and $R^8$ together with the —N—$CR^2R^3$—$CR^4R^5$ group joining them together form the following residue

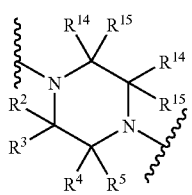

or $R^1$ and $R^2$ together with the —N—$CR^3$ group joining them together form the following residue

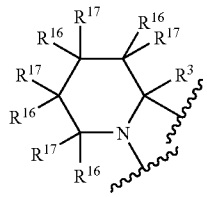

whereby, in this case, b denotes 1 and c denotes 0;

or $R^6$ and $R^8$ together with the —N—$CR^7$ group joining them together form the following residue

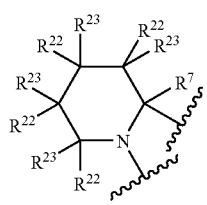

whereby, in this case, b denotes 1 and a denotes 0;

$R^9$ denotes a phenyl residue, which in each case is unsubstituted or substituted with 1 or 2 substituents mutually independently selected from the group comprising F, Cl, Br, I, —CN, methyl, ethyl, n-propyl, isopropyl, n-butyl, 2-butyl, isobutyl, tert-butyl, ethenyl, ethynyl, cyclopropyl, —O—$CH_3$, —O—$C_2H_5$, —O—$C_3H_7$, —$NO_2$, —$CF_3$ and —O—$CF_3$;

$R^{10}$, $R^{11}$ and $R^{12}$, mutually independently, in each case denote H; F; Cl; Br; —$CF_3$; —$NO_2$; —CN; —O—$CF_3$; an alkyl residue selected from the group comprising methyl, ethyl, n-propyl, isopropyl, isobutyl and tert-butyl; ethenyl; ethynyl or cyclopropyl;

and $R^{13}$ denotes H or an alkyl residue selected from the group comprising methyl, ethyl, n-propyl, isopropyl, n-butyl, 2-butyl, isobutyl and tert-butyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted propiolic acid amides of the above-mentioned general formula I are furthermore very particularly preferred, in which a, b and c, mutually independently, in each case denote 0 or 1, whereby the sum of a, b and c is equal to 2;

A denotes a residue selected from the group comprising

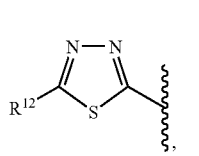 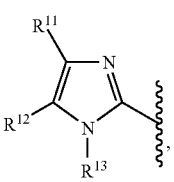

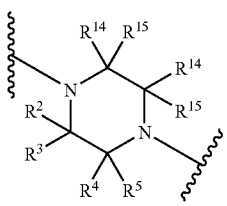

R¹ and R⁸, mutually independently, in each case denote H, methyl or isopropyl;

R², R³, R⁴, R⁵, R⁶, R⁷, R¹⁴ and R¹⁵, mutually independently, in each case denote H or an alkyl residue selected from the group comprising methyl and ethyl;

or R¹ and R⁸ together with the —N—CR²R³—CR⁴R⁵ group joining them together form the following residue R⁹ denotes a phenyl residue, which in each case is unsubstituted or substituted with 1 or 2 substituents mutually independently selected from the group comprising F, Cl, Br, I and —CN;

R¹⁰, R¹¹ and R¹², mutually independently, in each case denote H; or an alkyl residue selected from the group comprising methyl, ethyl, n-propyl, isopropyl, isobutyl and tert-butyl;

and R¹³ denotes H or an alkyl residue selected from the group comprising methyl, ethyl, n-propyl, isopropyl, n-butyl, 2-butyl, isobutyl and tert-butyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted propiolic acid amides of the above-mentioned general formula I are most preferred selected from the group comprising compounds according to one or more of Claims 1 to 21 selected from the group comprising

[1] 1-(3-phenyl-propiolyl)-4-(thiophen-3-yl)-piperazine,

[2] 1-(3-phenyl-propiolyl)-4-(thiazol-4-yl)-piperazine,

[3] 1-(3-phenyl-propiolyl)-4-(1-methyl-imidazol-2-yl)-piperazine,

[4] (R)-2-methyl-1-(3-(3-chloro-phenyl)-propiolyl)-4-(thiazol-4-yl)-piperazine,

[5] 2-methyl-1-(3-(3-chloro-phenyl)-propiolyl)-4-(1,3,4-thiadiazol-2-yl)-piperazine,

[6] 3-(3-chlorophenyl)-N-(2-(methyl(1,3,4-thiadiazol-2-yl)amino)ethyl)propiolamide,

[7] 3-(3-chlorophenyl)-N-(2-(methyl(thiazol-5-yl)amino)ethyl)propiolamide and

[8] 3-(3-chlorophenyl)-N-(2-(methyl(1-methyl-1H-imidazol-2-yl)amino)ethyl)propiolamide;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted propiolic acid amides of the above-mentioned general formula I are likewise particularly preferred, which, after 60 minutes of incubation in 450 μg protein from pig brain homogenate at a temperature between 20° C. and 25° C. in a concentration of less than 2000 nM, preferably of less than 1000 nM, particularly preferably of less than 700 nM, very particularly preferably of less than 100 nM, even more preferably of less than 30 nM, bring about a 50-percent displacement of [³H]-2-methyl-6-(3-methoxyphenyl)-ethynylpyridine which is present in a concentration of 5 nM.

Thereby, the determination of the displacement of [³H]-2-methyl-6-(3-methoxyphenyl)-ethynylpyridine is performed as described in the section Pharmacological Methods, I. Method for determining the inhibition of [³H]-MPEP-bonding in the mGluR5 receptor bonding assay.

A further subject matter of the present invention is a method for producing compounds of the general formula I indicated above according to which at least one compound of the general formula II,

A-X, in which A has the above-mentioned meaning and X denotes a leaving group, preferably a halogen residue or a sulphonic acid ester, is transferred with at least one compound of the general formula III,

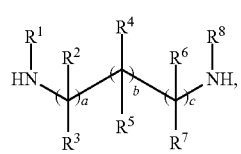

III in which a, b, c, R¹, R², R³, R⁴, R⁵, R⁶, R⁷ and R⁸ have the above-mentioned meaning, optionally in a reaction medium, optionally in the presence of at least one base, preferably in the presence of at least one base selected from the group comprising triethylamine, sodium hydrogencarbonate, dimethylaminopyridine, potassium carbonate and sodium hydroxide, and/or at least one metallo-organic compound and/or at least one metal hydride reagent, preferably in the presence of at least one metallo-organic compound or one metal hydride reagent selected from the group comprising n-butyllithium, phenyllithium, sodium hydride, potassium hydride and sodium amide, or in the presence of at least one copper salt, preferably in the presence of at least one copper salt selected from the group comprising copper(I) chloride and copper(I) iodide, and optionally in the presence of at least one metal, preferably in the presence of copper, preferably at a temperature of −70° C. to 300° C., particularly preferably of −70° C. to 150° C., into a corresponding compound of the general formula IV, optionally in the form of a corresponding salt,

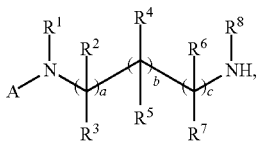

in which a, b, c, A, $R^1$, $R^2$, $R^3$, $R^4$, $R^5$, $R^6$, $R^7$ and $R^8$ have the above-mentioned meaning, and this is optionally purified and/or isolated;

or at least one compound of the general formula II is transferred with at least one compound of the general formula V,

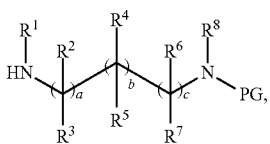

in which a, b, c, $R^1$, $R^2$, $R^3$, $R^4$, $R^5$, $R^6$, $R^7$ and $R^8$ have the above-mentioned meaning and PG denotes a protective group, preferably a protective group selected from the group comprising tert-butyloxy-carbonyl, benzyl, benzyloxycarbonyl and 9-fluoroenylmethyloxycarbonyl, optionally in a reaction medium, optionally in the presence of at least one base, preferably in the presence of at least one base selected from the group comprising triethylamine, sodium hydrogencarbonate, dimethylaminopyridine, potassium carbonate and sodium hydroxide, and/or at least one metallo-organic compound and/or at least one metal hydride reagent, preferably in the presence of at least one metallo-organic compound or one metal hydride reagent selected from the group comprising n-butyllithium, phenyllithium, sodium hydride, potassium hydride and sodium amide, or in the presence of at least one copper salt, preferably in the presence of at least one copper salt selected from the group comprising copper(I) chloride and copper(I) iodide, and optionally in the presence of at least one metal, preferably in the presence of copper, or in the presence of at least one catalyst, preferably in the presence of at least one palladium catalyst selected from the group comprising bis(dibenzylidenacetone)palladium [Pd(dba)$_2$]; tris(dibenzylidenacetone)dipalladium [Pd$_2$dba$_3$]; dichlorobis(tri-o-tolylphosphine)palladium [Pd(P(o-Tol)$_3$)$_2$Cl$_2$]; palladiumchloride [PdCl$_2$]; palladiumacetate [Pd(OAc)$_2$]; palladiumtrifluoroacetate [Pd(O$_2$CCF$_3$)$_2$]; tetrakistriphenylphosphinepalladium [Pd(PPh$_3$)$_4$]; bistriphenylphosphinepalladiumdichloride [Pd(PPh$_3$)$_2$Cl$_2$]; bistriphenylphosphinepalladiumacetate [Pd(PPh$_3$)$_2$(OAc)$_2$] and dichloro[1,1'-bis(diphenylphosphino)ferrocene]palladium [Pd(dppf)Cl$_2$], optionally in the presence of at least one ligand, preferably in the presence of at least one ligand selected from the group comprising (±)-2,2'-bis(diphenylphosphino)-1,1'-binaphthalene (BINAP), diphenylphosphinoferrocene (dppf), tri-tert.-butylphosphine [P(tBu)$_3$], triphenylphosphine [P(Ph)$_3$], tri-orthotolylphosphine [P(oTol)$_3$], tri-2-furylphosphin [P(2-furyl)$_3$], dicyclohexyl-(2',6'-dimethoxybiphenyl-2-yl)phosphine, dicyclohexyl-(2',6'-diisopropoxybiphenyl-2-yl)phosphine and biphenyl-2-yldicyclohexylphosphine, optionally in the presence of at least one organic or inorganic base selected from the group potassium-tert-butoxide, sodium-tert-butoxide, tri-potassium phosphate, caesium carbonate, lithiumbis(trimethylsilyl)amide, sodiumbis(trimethylsilyl)amide and potassiumbis(trimethylsilyl)amide, preferably at a temperature of −70° C. to 300° C. into at least one compound of the general formula VI,

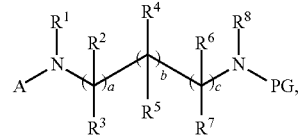

in which a, b, c, A, $R^1$, $R^2$, $R^3$, $R^4$, $R^5$, $R^6$, $R^7$, $R^8$ and PG have the above-mentioned meaning, and this is optionally purified and/or isolated;

or at least one compound of the general formula VII,

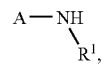

in which $R^1$ and A have the above-mentioned meaning, is transferred with at least one compound of the general formula VIII,

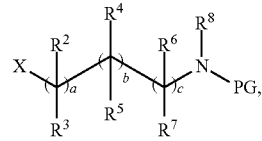

in which a, b, c, $R^2$, $R^3$, $R^4$, $R^5$, $R^6$, $R^7$, $R^8$ and PG have the above-mentioned meaning and X denotes a leaving group, preferably a halogen residue or a sulphonic acid ester, particularly preferably a chlorine or bromine residue, optionally in a reaction medium, optionally in the presence of at least one base, preferably in the presence of at least one base selected from the group comprising potassium-tert-butoxide, sodium hydroxide, potassium hydroxide, dimethylamine and triethylamine, particularly preferably in the presence of diethylamin, or optionally in the presence of at least one metallo-organic compound, preferably in the presence of at least one metallo-organic compound selected from the group comprising methyllithium and butyllithium or optionally in the presence of at least one metal hydride compound, particularly preferably in the presence of sodium hydride, preferably at a temperature of −70° C. to 300° C., particularly preferably of −70° C. to 150° C., into at least one corresponding compound of the general formula VI and this is optionally purified and/or isolated;

and at least one compound of the general formula VI, in the event that PG denotes a tert-butoxycarbonyl- or 9-fluorenylmethyloxycarbonyl group, is transferred in a reaction medium, in the presence of at least one acid, preferably in the presence of at least one acid selected from the group comprising hydrochloric acid and trifluoroacetic acid, preferably at a temperature between −70° C. and 100° C. or, in the event that PG denotes a benzyl group or benzyloxycarbonyl group, in a reaction medium, in the presence of hydrogen and in the presence of at least one catalyst, preferably in the presence of palladium on coal, preferably at a temperature between −70° C. and 100° C. into at least one corresponding compound of the general formula IV, optionally in the form of a corresponding salt, and this is optionally purified and/or isolated;

and at least one compound of the general formula IV is transferred into at least one corresponding compound of the general formula I, optionally in the form of a corresponding salt by conversion with at least one compound of the general formula $R^9$—C≡C—C(=O)—OH, in which $R^9$ has the above-mentioned meaning, in a reaction medium, optionally in the presence of at least one suitable coupling agent, optionally in the presence of at least one base, preferably in the presence of at least one base selected from the group comprising triethylamine, pyridine, dimethylaminopyridine, diisopropylethylamine and N-methyl-morpholine, preferably at a temperature of −70° C. to 100° C., or by conversion with at least one compound of the general formula $R^9$—C≡C—C(=O)—X, in which $R^9$ has the above-mentioned meaning and X denotes a leaving group, preferably a halogen residue, particularly preferably a chlorine or bromine residue, in a reaction medium, optionally in the presence of at least one base, preferably in the presence of at least one base selected from the group comprising triethylamine, dimethylaminopyridine, pyridine and diisopropylethylamine, preferably at a temperature of −70° C. to 100° C.,

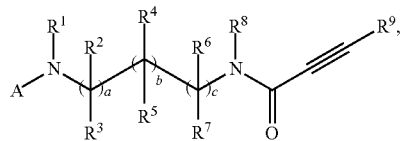

I in which a, b, c, A, $R^1$, $R^2$, $R^3$, $R^4$, $R^5$, $R^6$, $R^7$, $R^8$ and $R^9$ have the above-mentioned meaning, and this is optionally purified and/or isolated;

or at least one compound of the general formula IV is transferred into at least one corresponding compound of the general formula IX, optionally in the form of a corresponding salt by conversion with propionic acid [HC≡C—C(=O)—OH] in a reaction medium, optionally in the presence of at least one suitable coupling agent, optionally in the presence of at least one base, preferably in the presence of at least one base selected from the group comprising triethylamine, pyridine, dimethylaminopyridine, diisopropylethylamine and N-methyl-morpholine, preferably at a temperature of −70° C. to 100° C., or by conversion with at least one compound of the general formula HC≡C—C(=O)—X, in which X denotes a leaving group, preferably a halogen residue, particularly preferably a chlorine or bromine residue, in a reaction medium, optionally in the presence of at least one base, preferably in the presence of at least one base selected from the group comprising triethylamine, dimethylaminopyridine, pyridine and diisopropylethylamine, preferably at a temperature of −70° C. to 100° C.,

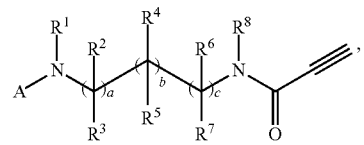

IX in which a, b, c, A, $R^1$, $R^2$, $R^3$, $R^4$, $R^5$, $R^6$, $R^7$ and $R^8$ have the above-mentioned meaning, and this is optionally purified and/or isolated, and at least one compound of the general formula IX is transferred into at least one corresponding compound of the general formula I, optionally in the form of a corresponding salt by conversion with at least one compound of the general formula $R^9$—X, in which $R^9$ has the above-mentioned meaning and X denotes a leaving group, preferably a halogen residue or a sulphonic acid ester, particularly preferably iodine, bromine or triflate, in a reaction medium, optionally in the presence of at least one catalyst, preferably in the presence of at least one palladium catalyst selected from the group comprising palladium chloride [PdCl$_2$], palladium acetate [Pd(OAc)$_2$], tetrakistriphenylphosphine palladium [Pd(PPh$_3$)$_4$], bistriphenylphosphine palladium dichloride [Pd(PPh$_3$)$_2$Cl$_2$] and bistriphenylphosphine palladium acetate [Pd(PPh$_3$)$_2$(OAc)$_2$], optionally in the presence of at least one ligand, preferably in the presence of at least one ligand selected from the group comprising triphenylphosphine, triphenylarsine and tri-2-furyl-phosphine, optionally in the presence of at least one inorganic salt, preferably in the presence of at least one inorganic salt selected from the group comprising lithium chloride and zinc chloride, optionally in the presence of at least one copper salt, preferably in the presence of copper iodide, optionally in the presence of at least one organic or inorganic base, preferably in the presence of at least one base selected from the group comprising triethylamine, [1,4]-diazabicyclo-[2.2.2]-octane, diisopropylamine, diisopropylethylamine, potassium carbonate and sodium hydrogencarbonate, preferably at a temperature between −70° C. and 300° C., and this is optionally purified and/or isolated.

A method for producing a compound of the general formula I is likewise a subject matter of the present invention, in which formula I at least one compound of the general formula III,

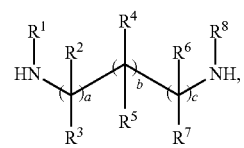

III in which a, b, c, $R^1$, $R^2$, $R^3$, $R^4$, $R^5$, $R^6$, $R^7$ and $R^8$ have the above-mentioned meaning, is transferred by conversion with at least one compound of the general formula $R^9$—C≡C—C(=O)—OH, in which $R^9$ has the above-mentioned meaning, in a reaction medium, optionally in the presence of at least one suitable coupling agent, optionally in the presence of at least one base, preferably in the presence of at least one base selected from the group comprising triethylamine, pyridine, dimethylaminopyridine, diisopropylethylamine and N-methyl-morpholine, preferably at a temperature of −70° C. to 100° C., or by conversion with at least one compound of the general formula $R^9$—C≡C—C(=O)—X, wherein $R^9$ has the above-mentioned meaning and X denotes a leaving group, preferably a halogen residue, particularly preferably a chlorine or bromine residue, in a reaction medium, optionally in the presence of at least one base, preferably in the presence of at least one base selected from the group comprising triethylamine, dimethylaminopyridine, pyridine and diisopropylethylamine, preferably at a temperature of −70° C. to 100° C., into at least one corresponding compound of the general formula XI, optionally in the form of a corresponding salt,

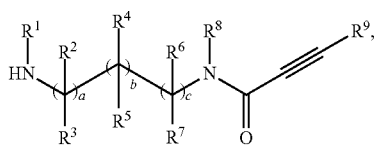

XI in which a, b, c, $R^1$, $R^2$, $R^3$, $R^4$, $R^5$, $R^6$, $R^7$, $R^8$ and $R^9$ have the above-mentioned meaning, and this is optionally purified and/or isolated;

or at least one compound of the general formula V,

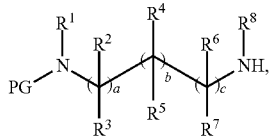

V in which a, b, c, $R^1$, $R^2$, $R^3$, $R^4$, $R^5$, $R^6$, $R^7$ and $R^8$ have the above-mentioned meaning and PG denotes a protective group, preferably a protective group selected from the group comprising tert-butyloxy-carbonyl, benzyl, benzyloxycarbonyl and 9-fluorenylmethyloxycarbonyl, is transferred by conversion with at least one compound of the general formula $R^9$—C≡C—C(=O)—OH, in which $R^9$ has the above-mentioned meaning, in a reaction medium, optionally in the presence of at least one suitable coupling agent, optionally in the presence of at least one base, preferably in the presence of at least one base selected from the group comprising triethylamine, pyridine, dimethylaminopyridine, diisopropylethylamine and N-methyl-morpholine, preferably at a temperature of −70° C. to 100° C., or by conversion with at least one compound of the general formula $R^9$—C≡C—C(=O)—X, in which $R^9$ has the above-mentioned meaning and X denotes a leaving group, preferably a halogen residue, particularly preferably a chlorine or bromine residue, in a reaction medium, optionally in the presence of at least one base, preferably in the presence of at least one base selected from the group comprising triethylamine, dimethylaminopyridine, pyridine and diisopropylethylamine, preferably at a temperature of −70° C. to 100° C., into at least one corresponding compound of the general formula XII, optionally in the form of a corresponding salt,

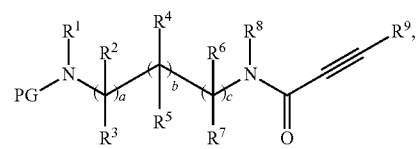

XII in which a, b, c, $R^1$, $R^2$, $R^3$, $R^4$, $R^5$, $R^6$, $R^7$, $R^8$, $R^9$ and PG have the above-mentioned meaning, and this is optionally purified and/or isolated;

and at least one compound of the general formula XII, in the event that PG denotes a tert-butoxycarbonyl or 9-fluorenylmethyloxycarbonyl group, is transferred into at least one corresponding compound of the general formula XI, optionally in the form of a corresponding slat, in a reaction medium, in the presence of at least one acid, preferably in the presence of at least one acid selected from the group comprising hydrochloric acid and trifluoroacetic acid, preferably at a temperature between −70° C. and 100° C. or, in the event that PG denotes a benzyl or benzyloxycarbonyl group, in a reaction medium, in the presence of hydrogen and in the presence of at least one catalyst, preferably in the presence of palladium on coal, preferably at a temperature between −70° C. and 100° C., and this is optionally purified and/or isolated; and at least one compound of the general formula XI is transferred into at least one corresponding compound of the general formula I, optionally in the form of a corresponding salt by conversion with at least one compound of the general formula

A-X, in which residue A has the above-mentioned meaning and X denotes a leaving group, preferably a halogen residue or a sulphonic acid ester, in a reaction medium, optionally in the presence of at least one base, preferably in the presence of at least one base selected from the group comprising triethylamine, sodium hydrogencarbonate, dimethylaminopyridine, potassium carbonate and sodium hydroxide, and/or at least one metallo-organic compound and/or at least one metal hydride reagent, preferably in the presence of at least one metallo-organic compound or one metal hydride reagent selected from the group comprising n-butyllithium, phenyllithium, sodium hydride, potassium hydride and sodium amide, or in the presence of at least one copper salt, preferably in the presence of at least one copper salt selected from the group comprising copper(I) chloride and copper(I) iodide, and optionally in the presence of at least one metal, preferably in the presence of copper, or in the presence of at least one catalyst, preferably in the presence of at least one palladium catalyst selected from the group comprising bis(dibenzylidenacetone)palladium [Pd(dba)$_2$]; tris(dibenzylidenacetone)dipalladium [Pd$_2$dba$_3$]; dichlorobis(tri-o-tolylphosphine)palladium [Pd(P(o-Tol)$_3$)$_2$Cl$_2$]; palladium chloride [PdCl$_2$]; palladium acetate [Pd(OAc)$_2$]; palladium trifluoroacetate [Pd(O$_2$CCF$_3$)$_2$]; tetrakistriphenylphosphine palladium [Pd(PPh$_3$)$_4$]; bistriphenylphosphine palladium-dichloride [Pd(PPh$_3$)$_2$Cl$_2$]; bistriphenylphosphine palladium acetate [Pd(PPh$_3$)$_2$(OAc)$_2$] and dichloro[1,1'-bis(diphenylphosphino)ferrocene]palladium [Pd(dppf)Cl$_2$], optionally in the presence of at least one ligand, preferably in the presence of at least one ligand selected from the group comprising (±)-2,2'-bis(diphenylphosphino)-1,1'-binaphthalene (BINAP), diphenylphosphinoferrocene (dppf), tri-tert.-butylphosphine [P(tBu)$_3$], triphenylphosphine [P(Ph)$_3$], triortho-tolylphosphine [P(oTol)₃], tri-2-furylphosphine [P(2-furyl)₃], dicyclohexyl-(2',6'-dimethoxybiphenyl-2-yl)phosphine, dicyclohexyl-(2',6'-diisopropoxybiphenyl-2-yl)phosphine and biphenyl-2-yldicyclohexylphosphine, optionally in the presence of at least one organic or inorganic base selected from the group potassium-tert-butoxide, sodium-tert-butoxide, tri-potassium phosphate, caesium carbonate, lithiumbis(trimethylsilyl)amide, sodiumbis(trimethylsilyl)amide and potassiumbis(trimethylsilyl)amide, preferably at a temperature of −70° C. to 300° C.,

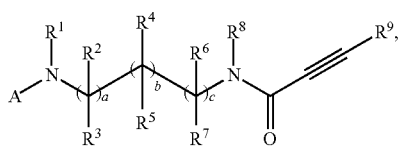

in which a, b, c, A, $R^1$, $R^2$, $R^3$, $R^4$, $R^5$, $R^6$, $R^7$, $R^8$ and $R^9$ have the above-mentioned meaning, and this is optionally purified and/or isolated.

A method according to the invention for producing substituted propiolic acid amides of the above-mentioned general formula I is also indicated in following Diagram 1.

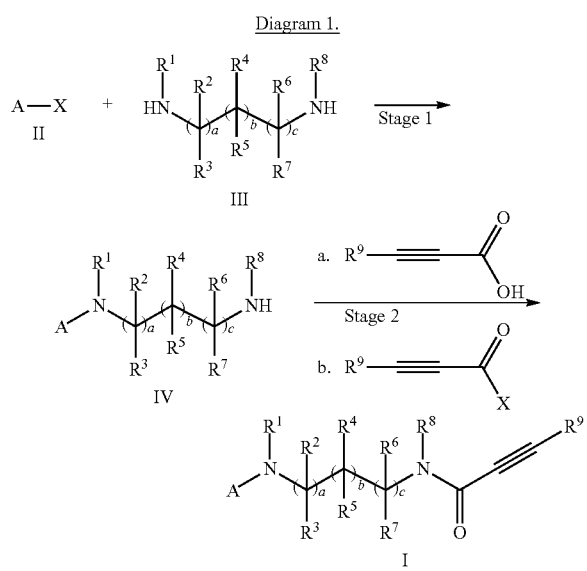

In stage 1, compounds of the above-mentioned general formula II, in which X denotes a leaving group, preferably a halogen residue or a sulphonic acid ester selected from the group comprising mesylate, triflate and tosylate, particularly preferably a chlorine or bromine atom, are converted with compounds of the above-mentioned general formula III, optionally in a reaction medium, preferably selected from the group comprising methanol, ethanol, isopropanol, n-butanol, diethylether, tetrahydrofuran, dichloromethane, chloroform, dimethylformamide, acetonitrile, pyridine, dioxane, ethylacetate, dimethylsulphoxide, toluol and corresponding mixtures, particularly preferably in a reaction medium selected from the group comprising methanol, ethanol and n-butanol, optionally in the presence of at least one organic or inorganic base, preferably selected from the group comprising triethylamine, sodium hydrogencarbonate, dimethylaminopyridine, potassium carbonate and sodium hydroxide, and/or optionally in the presence of at least one metal salt, preferably a copper salt, particularly preferably copper(I) iodide or copper (I) chloride, and optionally in the presence of at least one metal, preferably copper, and/or optionally in the presence of at least one metallo-organic compound or a metal hydride reagent, preferably selected from the group comprising n-butyllithium, phenyllithium, sodium hydride, potassium hydride and sodium amide, preferably at temperatures of −70° C. to 300° C., particularly preferably at temperatures of −70° C. to 150° C., to yield compounds of the general formula IV.

In stage 2, compounds of the above-mentioned general formula IV are converted with carboxylic acids of the above-mentioned general formula $R^9$—C≡C—C(=O)—OH in a reaction medium, preferably selected from the group comprising diethylether, tetrahydrofuran, acetonitrile, methanol, ethanol, (1,2)-dichloroethane, dimethylformamide, dichloromethane and corresponding mixtures, optionally in the presence of at least one coupling agent, preferably selected from the group comprising 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), PL-EDC (polymer-bound N-benzyl-3-((ethylimino)methyleneamino)-N,N-dimethylpropane-1-aminium chloride), 1,1'-carbonyl-diimidazol (CDI), N-[(dimethylamino)-1H-1,2,3-triazolo[4,5-b]pyridino-1-ylmethylene]-N-methylmethanaminium hexafluorophosphate N-oxide (HATU), O-(benzotriazol-1-yl)-N,N,N', N'-tetramethyluroniom hexafluorophosphate (HBTU), O-(benzotriazol-1-yl)-N,N,N',N'-tetramethyluronium-tetrafluoroborate (TBTU), 1-hydroxy-7-azabenzotriazol (HOAt) and polymer-bound carbodiimide resin (PS-carbodiimide resin, PSii), particularly preferably in the presence of a coupling agent selected from the group comprising TBTU, EDCI and PL-EDC, optionally in the presence of at least one organic base, preferably selected from the group comprising triethylamine, pyridine, dimethylaminopyridine, N-methylmorpholine, [1,4]-diazabicyclo-[2.2.2]-octane (DABCO), 1,8-diazabicyclo[5.4.0]andec-7-en (DBU), 1,5-diazabicyclo [4.3.0]non-5-en (DBN) and diisopropylethylamine, preferably in the presence of diisopropylethylamine or triethylamine, preferably at temperatures of −70° C. to 250° C. to yield compounds of the general formula I.

Alternatively, compounds of the above-mentioned general formula IV are converted with carboxylic acid derivatives of the above-mentioned general formula $R^9$—C≡C—C(=O)—X, in which X denotes a leaving group, preferably a halogen residue, particularly preferably chlorine or bromine, in a reaction medium, preferably selected from the group comprising diethylether, tetrahydrofuran, acetonitrile, methanol, ethanol, dimethylformamide, dichloromethane, 1,2-dichloroethane and corresponding mixtures, optionally in the presence of an organic or inorganic base, preferably selected from the group comprising triethylamine, dimethylaminopyridine, pyridine and diisopropylamine, at temperatures of −70° C. to 250° C. to yield compounds of the general formula I.

A further method according to the invention for producing compounds of the general formula IV is also indicated in following Diagram 2.

Diagram 2.

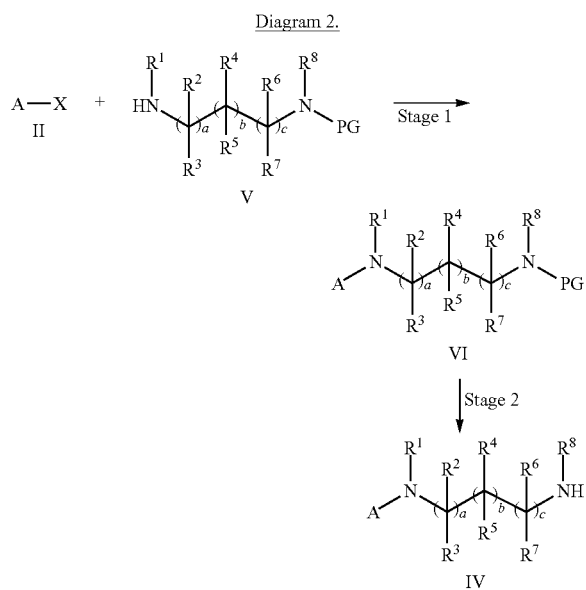

In stage 1, compounds of the above-mentioned general formula II, in which X denotes a leaving group, preferably a halogen residue or a sulphonic acid ester selected from the group comprising mesylate, triflate and tosylate, particularly preferably a chlorine or bromine atom, are converted with compounds of the above-mentioned general formula V, in which PG denotes a protective group, preferably a protective group selected from the group comprising tert-butyloxy-carbonyl, benzyloxycarbonyl, benzyl and 9-fluorenylmethyloxycarbonyl, optionally in a reaction medium, preferably selected from the group comprising methanol, ethanol, isopropanol, n-butanol, diethylether, tetrahydrofuran, dichloromethane, chloroform, dimethylformamide, acetonitrile, pyridine, dioxane, ethylacetate, dimethylsulphoxide, toluol and corresponding mixtures, particularly preferably in a reaction medium selected from the group comprising methanol, ethanol and n-butanol, optionally in the presence of at least one organic or inorganic base, preferably selected from the group comprising triethylamine, sodium hydrogencarbonate, dimethylaminopyridine, potassium carbonate and sodium hydroxide, and/or optionally in the presence of at least one metal salt, preferably a copper salt, particularly preferably copper(I) iodide or copper(I) chloride, and optionally in the presence of at least one metal, preferably copper, and/or optionally in the presence of at least einer metallo-organic compound or a metal hydride reagent, preferably selected from the group comprising n-butyllithium, phenyllithium, sodium hydride, potassium hydride and sodium amide, preferably at temperatures of −70° C. to 300° C., particularly preferably at temperatures of −70° C. to 150° C., to yield compounds of the general formula VI.

Alternatively, in stage 1, compounds of the general formula II, in which X denotes a leaving group, preferably a halogen residue or a sulphonic acid ester selected from the group comprising mesylate, triflate and tosylate, particularly preferably a chlorine, bromine, iodine atom or triflate, are converted with compounds of the above-mentioned general formula V, optionally in a reaction medium, preferably in a reaction medium selected from the group comprising benzol, toluol, xylol, trimethylbenzol, tetrahydrofuran, dimethoxyethane, dioxane and corresponding mixtures, particularly preferably in a reaction medium selected from the group comprising toluol, xylol and trimethylbenzol, optionally in the presence of at least one catalyst, preferably in the presence of at least one catalyst selected from the group comprising bis(dibenzylidenacetone)palladium [Pd(dba)$_2$], tris(dibenzylidenacetone)dipalladium [Pd$_2$dba$_3$], dichlorobis(tri-o-tolylphosphine)palladium [Pd(P(o-Tol)$_3$)$_2$Cl$_2$], palladium chloride [PdCl$_2$], palladium acetate [Pd(OAc)$_2$], palladium trifluoroacetate [Pd(O$_2$CCF$_3$)$_2$], tetrakistriphenylphosphine palladium [Pd(PPh$_3$)$_4$], bistriphenylphosphine palladium-dichloride [Pd(PPh$_3$)$_2$Cl$_2$], bistriphenylphosphine palladium acetate [Pd(PPh$_3$)$_2$(OAc)$_2$] and dichloro[1,1'-bis(diphenylphosphino)ferrocene]palladium [Pd(dppf)Cl$_2$], particularly preferably in the presence of a catalyst selected from the group comprising [Pd(dba)$_2$], [Pd$_2$dba$_3$], [Pd(P(o-Tol)$_3$)$_2$Cl$_2$], [Pd(O$_2$CCF$_3$)$_2$], [Pd(PPh$_3$)$_4$] and [Pd(OAc)$_2$], optionally in the presence of at least one ligand, preferably in the presence of at least one ligand selected from the group comprising (±)-2,2'-bis(diphenylphosphino)-1,1'-binaphthalene (BINAP), diphenylphosphinoferrocene (dppf), tri-tert.-butylphosphine [P(tBu)$_3$], triphenylphosphine [P(Ph)$_3$], tri-ortho-tolylphosphine [P(oTol)$_3$], tri-2-furylphosphine [P(2-furyl)$_3$], sterically demanding biarylphosphine ligands (Buchwald ligands) such as dicyclohexyl(2',6'-dimethoxybiphenyl-2-yl)phosphine, dicyclohexyl(2',6'-diisopropoxybiphenyl-2-yl)phosphine and biphenyl-2-yldicyclohexylphosphine, particularly preferably in the presence of at least one ligand selected from the group comprising [P(tBu)$_3$], dicyclohexyl(2',6'-dimethoxybiphenyl-2-yl)phosphine and dicyclohexyl(2',6'-diisopropoxybiphenyl-2-yl)phosphin, optionally in the presence of at least one organic or inorganic base selected from the group comprising potassium-tert-butoxide (KOtBu), sodium-tert-butoxide (NaOtBu), tri-potassium phosphate (K$_3$PO$_4$), caesium carbonate (Cs$_2$CO$_3$), lithiumbis(trimethylsilyl)amide [LiN(SiMe$_3$)$_2$], sodium bis(trimethylsilyl)amide [NaN(SiMe$_3$)$_2$] and potassium bis(trimethylsilyl)amide [KN(SiMe$_3$)$_2$], preferably at a temperature between −70° C. and 300° C. into a compound of the general formula IV. Compounds of the general formula II are particularly preferably converted with compounds of the general formula V in 1,2,4-trimethylbenzol in the presence of Pd(dba)$_2$Cl$_2$, [P(tBu)$_3$] and NaOtBu to yield compounds of the general formula VI.

In stage 2, compounds of the general formula VI, in the event that PG denotes a tert-butoxycarbonyl or 9-fluorenyl-methyloxycarbonyl group, is transferred in a reaction medium, preferably in a reaction medium selected from the group comprising methanol, ethylacetate, ethanol, isopropanol, n-butanol, diethylether, dioxane, tetrahydrofuran, chloroform, dichloromethane, dimethylformamide, acetonitrile, pyridine, dimethylsulphoxide, toluol and corresponding mixtures, in the presence of at least one acid, preferably in the presence of at least one acid selected from the group comprising hydrochloric acid and trifluoroacetic acid, preferably at a temperature between −70° C. and 100° C. or, in the event that PG denotes a benzyl group or benzyloxycarbonyl group, in a reaction medium, preferably in a reaction medium selected from the group comprising methanol, ethylacetate, ethanol, isopropanol, n-butanol, diethylether, dioxane, tetrahydrofuran, chloroform, dichloromethane, dimethylformamide, acetonitrile, pyridine, dimethylsulphoxide, toluol and corresponding mixtures, in the presence of hydrogen and in the presence of at least one catalyst, preferably in the presence of palladium on coal, preferably at a temperature between −70° C. and 100° C. into a corresponding compound of the general formula IV.

Suitable methods for removing the above-mentioned protective groups can also be found in the Monographs Protective Groups in Organic Synthesis, T. W. Greene et al., 3rd edition, 1999, Wiley, New York and Protecting Groups, P. J. Kocienski, 3rd edition, 2004, Georg Thieme Verlag, Stuttgart 2004. The corresponding parts of the references are hereby regarded as part of the disclosure.

A further method according to the invention for producing substituted propiolic acid amides of the above-mentioned general formula I is also indicated in following Diagram 3.

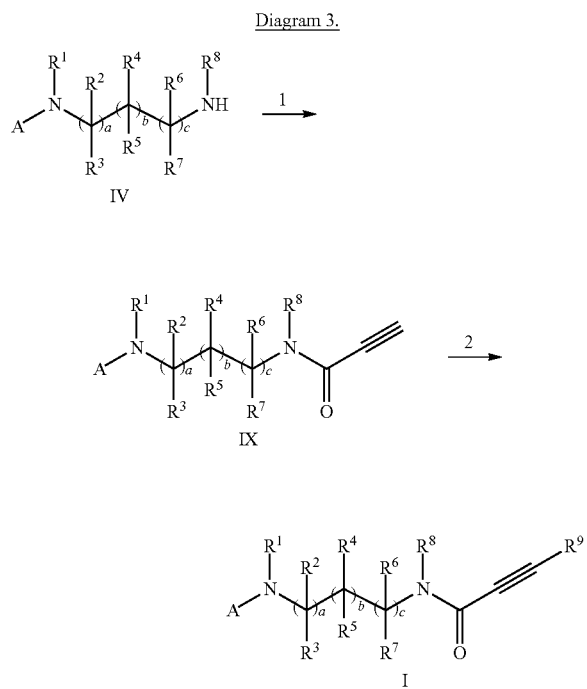

In stage 1, compounds of the above-mentioned general formula IV are converted with propiolic acid H—C≡C—C(=O)—OH or with carbonic acid derivatives of the general formula H—C≡C—C(=O)—X, in which X denotes a leaving group, preferably a halogen residue, particularly preferably chlorine or bromine, as described in Diagram 1, Stage 2, to yield compounds of the general formula IX.

In stage 2, compounds of the above-mentioned general formula IX are converted with compounds of the general formula $R^9$—X, in which $R^9$ has the above-mentioned meaning with the exception of hydrogen and X denotes a leaving group, preferably a halogen residue or a sulphonic acid ester, particularly preferably iodine, bromine or triflate, in a reaction medium, preferably in a reaction medium selected from the group comprising methanol, ethylacetate, ethanol, isopropanol, n-butanol, diethylether, dioxane, tetrahydrofuran, chloroform, dichloromethane, dimethylformamide, acetonitrile, pyridine, dimethylsulphoxide, water, toluol and corresponding mixtures, preferably in dimethylformamide, water, ethylacetate, tetrahydrofuran and corresponding mixtures, optionally in the presence of at least one catalyst, preferably in the presence of at least one catalyst selected from the group comprising palladium chloride [$PdCl_2$], palladium acetate [$Pd(OAc)_2$], tetrakistriphenylphosphine palladium [$Pd(PPh_3)_4$], bistriphenylphosphine palladium-dichloride [$Pd(PPh_3)_2Cl_2$] and bistriphenylphosphine palladium acetate [$Pd(PPh_3)_2(OAc)_2$], particularly preferably in the presence of a catalyst selected from the group comprising $Pd(PPh_3)_4$, $Pd(PPh_3)_2Cl_2$ and $Pd(PPh_3)_2(OAc)_2$, optionally in the presence of at least one ligand, preferably in the presence of at least one ligand selected from the group comprising triphenylphosphine, triphenylarsine and tri-2-furyl-phosphine, preferably in the presence of triphenylphosphine, optionally in the presence of at least one inorganic salt, preferably in the presence of at least one inorganic salt selected from the group comprising lithium chloride and zinc chloride, optionally in the presence of at least one copper salt, preferably in the presence of copper iodide, optionally in the presence of at least one organic or inorganic base, preferably in the presence of at least one base selected from the group comprising triethylamine, [1,4]-diazabicyclo-[2.2.2]-octane, diisopropylamine, diisopropylethylamine, potassium carbonate and sodium hydrogencarbonate, preferably at a temperature between −70° C. and 300° C. to yield a compound of the general formula I. Compounds of the general formula $R^9$—I or $R^9$—Br are particularly preferably converted with compounds of the general formula IX into dimethylformamide in the presence of $Pd(PPh_3)_2Cl_2$, copper(I) iodide and diisopropylamine or triethylamine.

A further method according to the invention for producing substituted propiolic acid amides of the above-mentioned general formula I is also indicated in following Diagram 4.

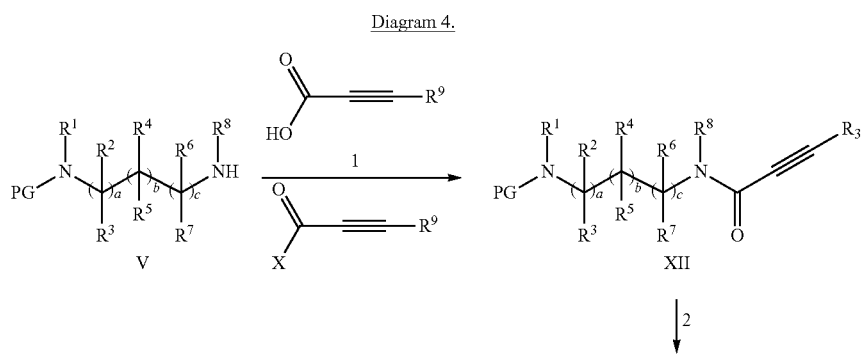

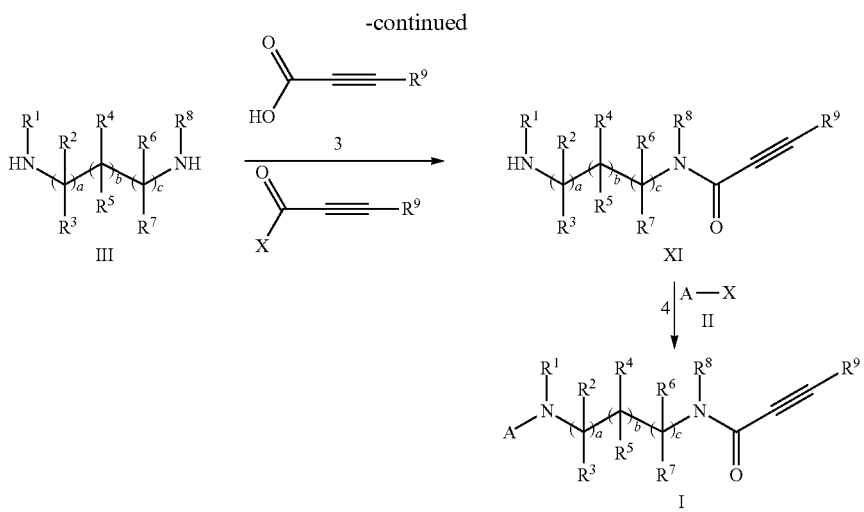

In stage 1, compounds of the general formula V, in which PG denotes a protective group, preferably a protective group selected from the group comprising tert-butyloxycarbonyl, benzyl, benzyloxycarbonyl and 9-fluorenylmethyloxycarbonyl, are converted with compounds of the general formula $R^9$—C≡C—C(=O)—OH or $R^9$—C≡C—C(=O)—X, in which X denotes a leaving group, preferably a halogen residue, particularly preferably chlorine or bromine, as in Diagram 1, Stage 2, to yield compounds of the general formula XII.

In stage 2, compounds of the general formula XII, in which PG denotes a protective group, preferably a protective group selected from the group comprising tert-butyloxycarbonyl, benzyl, benzyloxycarbonyl and 9-fluorenylmethyloxycarbonyl, as described in Diagram 2, Stage 2, are converted to yield compounds of the general formula XI.

In stage 3, compounds of the above-mentioned general formula III are converted with propiolic acid H—C≡C—C(=O)—OH or with carbonic acid derivatives of the above-mentioned general formula H—C≡C—C(=O)—X, in which X denotes a leaving group, preferably a halogen residue, particularly preferably chlorine or bromine, as described in Diagram 1, Stage 2, to yield compounds of the general formula XI.

In stage 4, compounds of the general formula XI are converted with compounds of the general formula II as described in Diagram 2, Step 1 to yield compounds of the general formula I.

Compounds of the general formula I, in which $R^1$ and $R^8$ each denote a hydrogen residue, referred to below as compounds of the general formula XV, can be transferred into compounds of the general formula I, in which $R^3$ and $R^8$ form a cyclic residue with the —N—$(CR^2R^3)_a$—$(CR^4R^5)_b$—$(CR^6R^7)_c$—N group joining them together, referred to below as compounds of the general formula XVI.

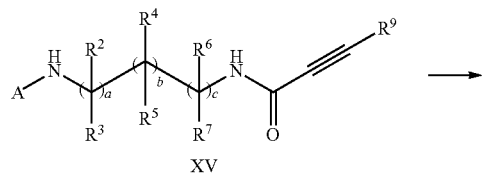

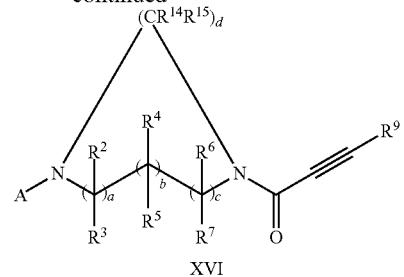

Compounds of the general formula XV can be converted with compounds of the general formula Y—$(CR^{14}R^{15})_d$—W, in which Y and W mutually independently in each case denote a leaving group, preferably a halogen residue or a sulphonic acid ester selected from the group comprising mesylate, triflate and tosylate, particularly preferably a chlorine or bromine atom, optionally in a reaction medium, preferably selected from the group comprising methanol, ethanol, isopropanol, n-butanol, diethylether, tetrahydrofuran, dichloromethan, chloroform, dimethylformamide, acetonitrile, pyridine, dioxane, ethylacetate, dimethylsulphoxide, toluol and corresponding mixtures, particularly preferably in a reaction medium selected from the group comprising acetontirile, dichloroethane, chloroform, dimethylformamide, tetrahydrofuran and diethylether, optionally in the presence of at least one organic or inorganic base, preferably selected from the group comprising triethylamine, sodium hydrogencarbonate, dimethylaminopyridine, potassium carbonate and sodium hydroxide, and/or optionally in the presence of at least one metallo-organic compound or a metal hydride reagent, preferably selected from the group comprising n-butyllithium, phenyllithium, sodium hydride, potassium-tert-butanolate, potassium hydride and sodium amide, preferably at temperatures of −71° C. to 300° C., particularly preferably at temperatures of −70° C. to 150° C., to yield compounds of the general formula XVI.

The conversion of compounds of the general formula XV is likewise preferably performed with paraformaldehyde to yield compounds of the general formula XVI, in which $R^{14}$ and $R^{15}$ in each case denote H and d is equal to 1, in a reaction medium, particularly preferably in a reaction medium selected from the group comprising acetonitrile, toluol, dichloromethane, tetrahydrofuran or diethylether, particularly preferably in toluol, and corresponding mixtures, in the presence of pyridinium-4-toluolsulphonate, preferably at a temperature of 0° C. to 150° C.

Compounds of the general formula XV can likewise be transferred into compounds of

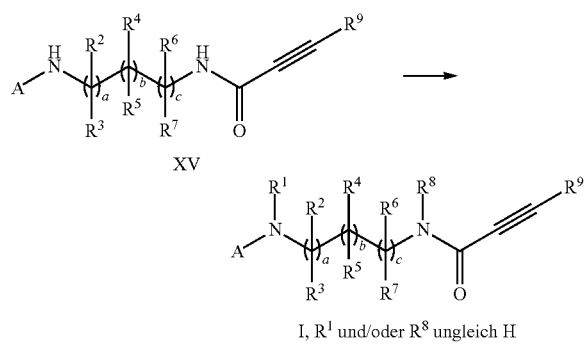

I, $R^1$ und/oder $R^8$ ungleich H the general formula I, in which at least one of residues $R^1$ and $R^8$ does not denote a hydrogen residue.

Compounds of the general formula XV can be converted with compounds of the general formula $R^1$—X or $R^8$—X, in which X denotes a leaving group, preferably a halogen residue or a sulphonic acid ester selected from the group comprising mesylate, triflate and tosylate, particularly preferably a chlorine or bromine atom, optionally in a reaction medium, preferably selected from the group comprising methanol, ethanol, isopropanol, n-butanol, diethylether, tetrahydrofuran, dichloromethane, chloroform, dimethylformamide, acetonitrile, pyridine, dioxane, ethylacetate, dimethylsulphoxide, toluol and corresponding mixtures, particularly preferably in a reaction medium selected from the group comprising acetonitrile, dichloroethane, chloroform, dimethylformamide, tetrahydrofuran and diethylether, optionally in the presence of at least one organic or inorganic base, preferably selected from the group comprising triethylamine, sodium hydrogencarbonate, dimethylaminopyridine, potassium carbonate and sodium hydroxide, and/or optionally in the presence of at least one metallo-organic compound or one metal hydride reagent, preferably selected from the group comprising n-butyllithium, phenyllithium, sodium hydride, potassium-tert-butanolate, potassium hydride and sodium amide, preferably at temperatures of −70° C. to 300° C., particularly preferably at temperatures of −70° C. to 150° C., to yield compounds of the general formula I, in which at least one of the residues $R^1$ and $R^8$ does not denote a hydrogen residue.

The compounds of the above-mentioned formulae II, III, V, VII, VIII, and of the general formulae Y—(CR$^{14}$R$^{15}$)$_d$—W, $R^9$—C≡C—C(=O)—OH, $R^9$—X, $R^1$—X, $R^8$—X, $R^9$—C≡C—C(=O)—X and H—C≡C—C(=O)—X are in each case available for purchase on the market and/or can be produced according to the conventional methods known to the person skilled in the art.

The conversions described above can in each case be performed under normal conditions familiar to the person skilled in the art, for example, in terms of pressure or the sequence of the addition of components. The optimum performance of the method according to the respective conditions can optionally be determined by the person skilled in the art by simple preliminary tests.

The intermediate and end products obtained according to the conversions described above can in each case, if desired and/or necessary, be purified and/or isolated according to conventional methods known to the person skilled in the art. Suitable purification methods are, for example, extraction methods and chromatographic methods such as column chromatography or preparative chromatography.

All of the method steps described above and in each case also the purification and/or isolation of intermediate or end products can partially or entirely be performed under an inert gas atmosphere, preferably under a nitrogen atmosphere.

In so far as the substituted propiolic acid amides according to the invention of the above-mentioned general formula I can be obtained after their production in the form of a mixture of the stereoisomers thereof, preferably in the form of the racemates thereof or other mixtures of the various enantiomers and/or diastereomers thereof, these can be separated and optionally isolated according to conventional methods known to the person skilled in the art. Chromatographic separating methods, in particular liquid chromatography methods under normal pressure or under increased pressure, preferably MPLC and HPLC methods, and methods of fractionated crystallisation are cited by way of example. Therein, in particular individual enantiomers, e.g. diastereomeric salts formed by means of HPLC on the chiral phase or by means of crystallisation with chiral acids such as (+) tartaric acid, (−) tartaric acid or (+) 10-camphor sulphonic acid, can be separated from one another.

The substituted propiolic acid amides according to the invention of the above-mentioned genera formula I and optionally in each case corresponding stereoisomers can be obtained according to conventional methods known to the person skilled in the art in the form of corresponding salts, preferably in the form of corresponding hydrochlorides, particularly in the form of corresponding physiologically acceptable salts, whereby the medicament according to the invention can have one or more salts or several of these compounds.

The respective salts of the substituted propiolic acid amides according to the invention of the above-mentioned general formula I and corresponding stereoisomers can, for example, be obtained by conversion with one or more inorganic acids and/or one or more organic acids. Suitable acids can be preferably selected from the group comprising perchloric acid, hydrochloric acid, hydrobromic acid, sulphuric acid, methanesulphonic acid, formic acid, acetic acid, oxalic acid, succinic acid, tartaric acid, mandelic acid, fumaric acid, lactic acid, citric acid, glutamic acid, saccharin acid, cyclohexanesulphonamide acid, aspartame, monomethylsebacic acid, 5-oxo-proline, hexane-1-sulphonic acid, nicotinic acid, 2-aminobenzoic acid, 3-aminobenzoic acid or 4-aminobenzoic acid, 2,4,6-trimethylbenzoic acid, α-lipoic acid, acetylglycine, hippuric acid, phosphoric acid, maleic acid, malonic acid and asparaginic acid.

The substituted propiolic acid amides according to the invention of the above-mentioned general formula I and optionally corresponding stereoisomers and in each case their physiologically acceptable salts can be obtained according to conventional methods known to the person skilled in the art also in the form of the solvates thereof, in particular in the form of the hydrates thereof.

It has been surprisingly found that the substituted propiolic acid amides according to the invention of the above-mentioned general formula I are suitable for mGluR5 receptor regulation and can therefore be used in particular as active pharmaceutical ingredients in medicaments for the prevention and/or treatment of disorders or illnesses related to these receptors or processes.

The substituted propiolic acid amides according to the invention of the above-mentioned general formula I and optionally corresponding stereoisomers and in each case the corresponding salts and solvates appear to be toxicologically safe and are therefore suitable as active pharmaceutical ingredients in medicaments.

A further subject matter of the present invention is therefore a medicament containing at least one substituted propiolic acid amide according to the invention of the above-mentioned general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

The medicament according to the invention is suitable for mGluR5 receptor regulation, in particular for inhibition of the mGluR5 receptor.

The medicament according to the invention is particularly suitable for the prevention and/or treatment of disorders and/or illnesses which are at least partially mediated by mGluR5 receptors.

The medicament according to the invention is therefore particularly preferably suitable for the treatment and/or prevention of pain, preferably of pain selected from the group consisting of acute pain, chronic pain, neuropathic pain and visceral pain; migraine; depression; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably Attention Deficit Disorder (ADD); anxiety states; panic attacks; epilepsy; coughing; urinary incontinence; diarrhoea; pruritus; schizophrenia; cerebral ischaemia; muscle spasms; cramps; lung illnesses, preferably selected from the group comprising asthma and pseudo-croup; regurgitation (vomiting); stroke; dyskinesia; retinopathy; listlessness; laryngitis; disorders of food intake, preferably selected from the group consisting of bulimia, cachexia, anorexia and obesity; dependency on alcohol; dependency on medicines; dependency on drugs, preferably dependency on nicotine and/or cocaine; alcohol abuse; abuse of medication; drug abuse; preferably nicotine and/or cocaine abuse; withdrawal symptoms associated with dependency on alcohol, medications and/or drugs (in particular nicotine and/or cocaine); development of tolerance to medications, preferably to natural or synthetic opioids; stomach-esophagus-reflux-syndrome; gastroesophagal reflux; irritable bowel syndrome; for diuresis; for antinatriuresis; for influencing the cardiovascular system; for increasing vigilance; for increasing libido; for modulating locomotor activity or for local anaesthesia.

The medicament according to the invention is very particularly preferably suitable for the prevention of pain, preferably of pain selected from the group consisting of acute pain, chronic pain, neuropathic pain and visceral pain; anxiety states; panic attacks; dependency on alcohol; dependency on medicines; disorders of food intake, preferably selected from the group consisting of bulimia, cachexia, anorexia and obesity; dependency on drugs, preferably dependency on nicotine and/or cocaine; alcohol abuse; abuse of medication; drug abuse; preferably nicotine and/or cocaine abuse; withdrawal symptoms associated with dependency on alcohol, medications and/or drugs (in particular nicotine and/or cocaine); development of tolerance to medications and/or drugs, preferably to natural or synthetic opioids; stomach-esophagus-reflux-syndrome; gastroesophagal reflux and irritable bowel syndrome.

The medicament according to the invention is even more preferably suitable for the prevention and/or the treatment of pain, preferably of pain selected from the group consisting of acute pain, chronic pain, neuropathic pain and visceral pain; anxiety states and panic attacks.

The medicament according to the invention is most preferably suitable for the prevention and/or the treatment of pain, preferably of acute pain, chronic pain, neuropathic pain and visceral pain.

A further subject matter of the present invention is the use of at least one substituted propiolic acid amide according to the invention of the above-mentioned general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a medicament for mGluR5 receptor regulation, preferably for inhibition of the mGluR5 receptor.

The use of at least one substituted propiolic acid amide according to the invention of the above-mentioned general formula I is preferred, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a medicament for the prevention and/or treatment of disorders and/or illnesses which are at least partially mediated by mGluR5 receptors.

The use of at least one substituted propiolic acid amide according to the invention of the above-mentioned general formula I is particularly preferred, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a medicament for the prevention and/or treatment of pain, preferably of pain selected from the group consisting of acute pain, chronic pain, neuropathic pain and visceral pain; migraine; depression; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably Attention Deficit Disorder (ADD); anxiety states; panic attacks; epilepsy; coughing; urinary incontinence; diarrhoea; pruritus; schizophrenia; cerebral ischaemia; muscle spasms; cramps; lung illnesses, preferably selected from the group comprising asthma and pseudo-croup; regurgitation (vomiting); stroke; dyskinesia; retinopathy; listlessness; laryngitis; disorders of food intake, preferably selected from the group consisting of bulimia, cachexia, anorexia and obesity; dependency on alcohol; dependency on medicines; dependency on drugs, preferably dependency on nicotine and/or cocaine; alcohol abuse; abuse of medication; drug abuse; preferably nicotine and/or cocaine abuse; withdrawal symptoms associated with dependency on alcohol, medications and/or drugs (in particular nicotine and/or cocaine); development of tolerance to medications, preferably to natural or synthetic opioids; stomach-esophagus-reflux-syndrome; gastroesophagal reflux; irritable bowel syndrome; for diuresis; for antinatriuresis; for influencing the cardiovascular system; for increasing vigilance; for increasing libido; for modulating locomotor activity or for local anaesthesia.

The use of at least one substituted propiolic acid amide according to the invention of the above-mentioned general formula I is very particularly preferred, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a medicament for the prevention and/or treatment of pain, preferably of pain selected from the group consisting of acute pain, chronic pain, neuropathic pain and visceral pain; anxiety states; panic attacks; dependency on alcohol; dependency on medicines; disorders of food intake, preferably selected from the group consisting of bulimia, cachexia, anorexia and obesity; dependency on drugs, preferably dependency on nicotine and/or cocaine; alcohol abuse; abuse of medication; drug abuse; preferably nicotine and/or cocaine abuse; withdrawal symptoms associated with dependency on alcohol, medications and/or drugs (in particular nicotine and/or cocaine); development of tolerance to medications and/or drugs, particularly to natural or synthetic opioids; stomach-esophagus-reflux-syndrome; gastroesophagal reflux and irritable bowel syndrome.

The use of at least one substituted propiolic acid amide according to the invention of the above-mentioned general formula I is even more preferred, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a medicament for the prevention and/or treatment of pain, preferably of pain selected from the group consisting of acute pain, chronic pain, neuropathic pain and visceral pain; anxiety states and panic attacks.

The medicament according to the invention is suitable for administration to adults and childrens including infants.

The medicament according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example, in the form of pellets or granules, optionally pressed into tablets, packaged in capsules or suspended in a liquid, and may also be administered as such.

In addition to at least one substituted propiolic acid amide according to the invention of the above-mentioned general formula I, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or optionally in the form of a corresponding salt or in each case in the form of a corresponding solvate, the medicament according to the invention conventionally contains further physiologically acceptable pharmaceutical auxiliary substances, which are preferably selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the medicament is to be administered orally, subcutaneously, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

The substituted propiolic acid amide used in the medicament according to the invention of the above-mentioned general formula I in a depot in dissolved form or in a dressing, optionally with the addition of skin penetration promoters, are suitable percutaneous administration preparations.

Orally or percutaneously administrable formulations may also release the respective propiolic acid amides of the above-mentioned general formula I in a delayed manner.

Production of the medicaments according to the invention proceeds with the assistance of conventional means, devices, methods and processes well known from the prior art, such as are described for example in "Remington's Pharmaceutical Sciences", ed. A. R. Gennaro, 17th ed., Mack Publishing Company, Easton, Pa. (1985), in particular in part 8, chapters 76 to 93. The corresponding description is hereby introduced as a reference and is deemed to be part of the disclosure.

The quantity of the respective substituted propiolic acid amide of the above-mentioned general formula I to be administered to the patient may vary and is for example dependent on the weight or age of the patient and on the mode of administration, the indication and the severity of the complaint. Conventionally, 0.05 to 100 mg/kg, preferably 0.05 to 10 mg/kg of patient body weight of at least one such compound are administered.

Pharmacological Methods:

I. Method for Determining the Inhibition of the [$^3$H]-MPEP Bond in the mGluR5 Receptor Bond Assay Pig brain homogenate is produced by homogenisation (Polytron PT 3000, Kinematica AG, 10,000 rpm for 90 seconds) of pig brain halves without medulla, cerebellum and pons in buffer pH 8.0 (30 mM Hepes, Sigma, order no. H3375+1 tablet complete to 100 ml, Roche Diagnostics, order no. 1836145) in ratio 1:20 (brain weight/volume) and differential centrifugation at 900×g and 40,000×g. In each case, 450 µg protein from brain homogenate is incubated with 5 nM $^3$[H]-MPEP (Tocris, order no. R1212) (MPEP=2-methyl-6-(3-methoxyphenyl)-ethynylpyridine) in 250 µl incubation batches in 96 well microtitration plates and the compounds to be tested (10 µM in the test) in buffer (as above) at room temperature for 60 min.

Thereafter, the batches are filtered with the help of a Brandel Cell Harvester (Brandel, TYP Robotic 9600) on unifilter plates with glass fibre filter mats (Perkin Elmer, order no. 6005177) and subsequently washed with buffer (as above) 3 times with in each case 250 µl per sample. The filter plates are subsequently dried for 60 min at 55° C. 30 µL Ultima Gold™ scintillator is subsequently added per well (Packard Bio-Science, order no. 6013159) and the samples are measured after 3 hours on the β-counter (Mikrobeta, Perkin Elmer). The unspecific bond is determined by addition of 10 μM MPEP (Tocris, order no. 1212).

II. Method for Determining the $Ca^{2+}$ Influx in the mGluR5 Receptor Assay

An agonistic and/or antagonistic effect of substances can be determined on the mGluR5 receptor of the rat species with the following assay. According to this assay, the intracellular $Ca^{2+}$ release is quantified after activation of the mGluR5 receptor with the help of a $Ca^{2+}$-sensitive dye (type Fluo-4, Molecular Probes Europe BV, Leiden Netherlands) in the FlexStation (Molecular Devices, Sunnyvale, USA).

Preparation of Cortical Neurons:

Cortical neurons are prepared under sterile conditions from postnatal rats (P2-6). To this end, the cortex is removed and transferred directly into collagenase solution (PAA Laboratories GmbH, Cölbe, Germany) and incubated for 45 minutes in a heated separator (37° C., 300 rpm). The collagenase solution is subsequently removed and culture medium is added to the tissue.

Culture Medium (100 ml):

Neurobasal medium (Gibco Invitrogen GmbH, Karlsruhe, Germany)

2 mM L-glutamine (Sigma, Taufkirchen, Germany)

1 Vol-% antibiotic/antimycotic solution (PAA Laboratories GmbH, Cölbe, Germany)

15 ng/ml NGF (Gibco Invitrogen GmbH, Karlsruhe, Germany)

1 ml B27 Supplement (Gibco Invitrogen GmbH, Karlsruhe, Germany)

1 ml ITS Supplement (Sigma, Taufkirchen, Germany)

The cells are separated by resuspension and centrifuged after addition of 15 ml neurobasal medium through a 70 μm filter insert (BD Biosciences, Heidelberg, Germany). The resultant cell pellet is received in culture medium. The cells are subsequently plated out on poly-D-lysine-coated, black 96-hole-plates with a clear base (BD Biosciences, Heidelberg, Germany), which were previously coated with laminin (2 μg/cm², Gibco Invitrogen GmbH, Karlsruhe, Germany). The cell density is 15,000 cells/hole. The cells are incubated at 37° C. and 5% $CO_2$ and a change of medium is performed on the $2^{nd}$ or $3^{rd}$ day after preparation. Depending on cell growth, the functional investigation can be performed on the $3^{rd}$-$7^{th}$ day after preparation.

Description of the Functional $Ca^{2+}$ Influx Assay 20,000 CHO-hmGluR5 cells/well (Euroscreen, Gosselies, Belgium) are pipetted into 96 well plates (BD Biosciences, Heidelberg, Germany, Ref 356640, clear bottom, 96 well, Poly-D-Lysine) and incubated overnight in HBSS buffer (Gibco No.14025-050) with the following additions: 10% FCS (GIBCO, 10270-106) and doxycycline (BD Biosciences Clontech 631311 600 ng/ml).

For the functional investigation, the cells were loaded with 2 μM fluo-4 and 0.01 Vol % Pluronic F127 (Molecular Probes Europe BV, Leiden Netherlands) in HBSS buffer (Hank's buffered saline solution, Gibco Invitrogen GmbH, Karlsruhe, Germany) with probenicide (Sigma P8761, 0.69 mg/ml) for 30 min at 37° C.

The cells are then washed 3 times with washing buffer (HBSS buffer, Gibco No. 14025-050, with probenicide (Sigma P8761, 0.69 mg/ml) and subsequently received with the same buffer ad 100 μl. After 15 min., the plates are transferred into a Fluorometric Imaging Plate Reader (FLIPR, Molecular Devices, Sunnyvale, Calif.) for the determination of $Ca^{2+}$ measurements in the presence of DHPG ((S)-3,5-dihydroxyphenylglycine, Tocris Biotrend Chemikalien GmbH, Cologne, Germany, final DHPG concentration: 10 μM) and in the presence or absence of test substances.

In this case, the $Ca^{2+}$-dependent fluorescence is measured before and after addition of test substances. Quantification is performed by measurement of the maximum fluorescence intensity over time.

After recording the fluorescence base line for 10 sec., 50 μl test substance solution (various test substance concentrations in HBSS buffer with 1% DMSO and 0.02% Tween 20, Sigma) is added and the fluorescence signal is measured for 6 min. 50 μl DHPG solution ((S)-3,5-dihydroxyphenylglycine, Tocris Biotrend Chemikalien GmbH, Cologne, Germany, final DHPG concentration: 10 μM) is subsequently added and the inflow of $Ca^{2+}$ is simultaneously measured for 60 sec. The final DMSO concentration is 0.25% and the final Tween 20 content is 0.005%. The data are analysed with Microsoft Excel and GraphPad Prism. The dose-effect curves are calculated with non-linear regression and $IC_{50}$ values determined. Each data point is determined 3 times and $IC_{50}$ values are averaged from a minimum of 2 independent measurements.

Ki values are calculated according to the following formula: $Ki=IC50/(1+(AG_{Conc.}/EC50))$.

$AG_{Conc.}=10$ μM; EC50 corresponds to the DHPG concentration which is required for half the maximum inflow of $Ca^{2+}$.

III. Formaline Test in Rats:

The formaline test (Dubuisson, D. and Dennis, S. G., 1977, Pain, 4, 161-174) represents a model for acute and chronic pain. A biphasic nociceptive reaction, which is recorded by observation of three clearly differentiable behavioural patterns, is induced by a single formaline injection into the dorsal side of a rear paw in freely mobile test animals. The reaction has two phases: Phase 1=Immediate reaction (duration up to 10 min; paw shaking, licking), Phase 2=Late reaction (after a rest phase; likewise, paw shaking, licking; duration up to 60 min). The $1^{st}$ phase reflects a direct stimulation of the peripheral nocisensors with high spinal nociceptive input or glutamate release (acute pain phase); the $2^{nd}$ phase reflects a spinal and peripheral hypersensitisation (chronic pain phase). In the investigations presented here, the chronic pain component (phase 2) was evaluated.

Formaline with a volume of 50 μl and a concentration of 5% is administered subcutaneously into the dorsal side of the right rear paw of each animal. The substances to be tested are administered for 30 min before the formaline injection orally (p.o.), intravenously (i.v.) or intraperitoneally (i.p.). The specific changes in behaviour such as lifting and shaking the paw, shifts in weight of the animal as well as biting and licking reactions are observed and registered in the period of observation from 21 to 27 min after formaline injection. The various forms of behaviour are summarised in the so-called pain rate (PR), which, relative to the sub-intervals of 3 min, represents the calculation of an average nociception reaction. The calculation of PR is performed on the basis of a numerical weighting (=in each case factor 1, 2, 3) of the observed forms of behaviour (corresponding behavioural score 1, 2, 3) and is calculated with the following formula:

$$PR=[(T_0\times 0)+(T_1\times 1)+(T_2\times 2)+(T_3\times 3)]/180$$

whereby $T_0$, $T_1$, $T_2$, and $T_3$ in each case corresponds to the time in seconds in which the animal demonstrates modes of behaviour 0, 1, 2 or 3. The group size is 10 animals (n=10).

The following examples serve to explain the invention and do not restrict the general concept of the invention.

EXAMPLES

The yields of the produced compounds are not optimised. All temperatures are uncorrected.

The chemicals and solvents used were commercially acquired from the normal suppliers (Acros, Avocado, Aldrich, Bachem, Fluka, Lancaster, Maybridge, Merck, Sigma, TCI, etc.) or synthesised according to methods known to the person skilled in the art.

Silica gel 60 (0.040-0.063 mm) from E. Merck, Darmstadt was used as the stationary phase for the column chromatography.

The thin layer chromatographic tests were carried out with HPTLC ready plates, silica gel 60 F 254, from E. Merck, Darmstadt.

The mixture ratios of solvents, mobile solvents or for chromatographic investigations are always indicated in volume/volume.

Analysis was performed by mass spectroscopy and NMR.

Abbreviations:

aq. aqueous

Brine saturated aqueous NaCl solution

BuLi n-butyllithium

DCE 1,2-dichloroethane

DCM dichloromethane

DIC N,N'-diisopropylcarbodiimide

DIPE diisopropylether

DMF N,N-dimethylformamide

AE acetic acid ethylester

Ether diethylether

HOBt 1-hydroxy-1H-benzotriazol hydrate sol. solution

M molar

MeOH methanol

PL-EDC polymer-bound carbodiimide with following structure:

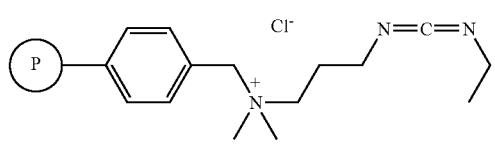

Loading: ~1.4 mmol/g

Particle size: 300-500 μm

PS— carbodiimide a polymer-bound carbodiimide with the following structure:

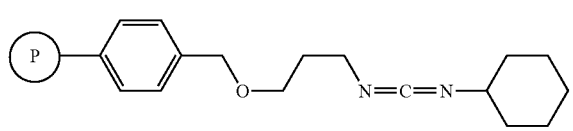

Loading: 0.9-1.4 mmol/g

Particle size: 75-150 μm

RT room temperature

CC Column chromatography

TFA Trifluoroacetic acid

Example 1

1-(3-phenyl-propiolyl)-4-(thiophene-3-yl)-piperazine hydrochloride

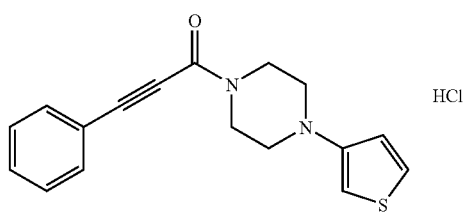

a) Synthesis of tert-butyl 4-(3-phenylpropiolyl)piperazine-1-carboxylate 0.80 ml (5.1 mmol) DIC and 0.69 g (5.1 mmol) HOBt were added to a solution of 750 mg (5.1 mmol) phenylpropiolic acid and 955 mg (5.1 mmol) tert-butylpiperazine-1-carboxylate in DMF (4 ml) and the reaction solution was stirred for 18 h at RT. 1 molar aq. $Na_2CO_3$ sol. (2 ml) was subsequently added and dilution with n-hexane (5 ml) was performed. The solid precipitated in this process (1.7 g) was sucked up, washed with n-hexane and used in the next stage without further purification.

b) Synthesis of 1-(phenylpropiolyl)-piperazine

A solution of 500 mg of the raw product obtained in example 1a) in DCM (2 ml) was cooled to 0° C. (ice bath) and 1.65 ml (21.5 mmol) TFA was slowly added, whereby the temperature did not exceed 5° C. After the end of addition, the solution was stirred for 1 h at RT. The mixture was subsequently poured onto ice water and alkalically adjusted with a 25% aq. $NH_3$ sol. (pH>10). Extraction was then performed with DCM (3×150 ml). The collected organic phases were washed with brine, dried over $MgSO_4$, filtered and the solvent removed in a vacuum. CC ($SiO_2$, MeOH/DCM 1:9) was performed with the residue, whereby 170 mg (0.8 mmol, 53% over 2 stages) of 1-(phenylpropiolyl)-piperazine was obtained.

c) Synthesis of 1-(3-phenyl-propiolyl)-4-(thiophene-3-yl)-piperazine 246 mg (2.57 mmol) sodium-tert.-butoxide and 0.22 ml (2.33 mmol) 3-bromothiophene were consecutively added to a solution of 500 mg (2.33 mmol) 1-(phenylpropiolyl)-piperazine in 1,2,4-trimethylbenzol (2 ml). A suspension of 66 mg (0.12 mmol) bis(dibenzylidenacetone)palladium(0) and 345 ml (0.12 mmol, 10% in hexane) tri-tert.-butylphosphine in 1,2,4-trimethylbenzol (1.2 ml) was added to the reaction solution. The mixture was subsequently stirred for 18 h at 120° C., diluted with AE and filtered over diatomite. The filtrate was concentrated in a vacuum and CC ($SiO_2$, DCM/DIPE 1:2) was performed with the residue, whereby 300 mg (1.01 mmol, 43%) 1-(3-phenyl-propiolyl)-4-(thiophene-3-yl)-piperazine was obtained.

d) Synthesis of 1-(3-phenyl-propiolyl)-4-(thiophene-3-yl)-piperazine hydrochloride 300 mg (1.01 mmol) 1-(3-phenyl-propiolyl)-4-(thiophene-3-yl)-piperazine was dissolved in acetone (10 ml) and 9 µl (0.51 mmol) water and 128 µl (1.0 mmol) trimethylchlorosilane were consecutively added. The resultant precipitation was sucked up and washed with acetone. In this process, 0.193 g (0.58 mmol, 57%) 1-(3-phenyl-propiolyl)-4-(thiophene-3-yl)-piperazine hydrochloride was obtained.
MS: [MH$^+$] 297.1

Example 3

1-(3-phenyl-propiolyl)-4-(1-methyl-imidazol-2-yl)-piperazine hydrochloride

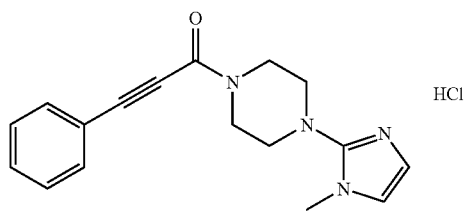

a) Synthesis of 1-(1-methyl-1H-imidazol-2-yl)piperazine 1.0 g (6.2 mmol) 2-bromine-1-methyl-1H-imidazol was fused with 3.2 ml (37.0 mmol) piperazine at 145° C. and stirred for 18 h at this temperature. After cooling to RT, the residue was received in 10% aq. hydrochloric acid and washed with AE. Alkalic adjustment was subsequently performed with a 10% aq. NaOH sol. (pH>12) and extraction with DCM. The organic phase was dried over MgSO$_4$, filtered and concentrated in a vacuum. In this process, 780 mg (4.7 mmol, 76%) 1-(1-methyl-1H-imidazol-2-yl)piperazine was obtained.

b) Synthesis of 1-(3-phenyl-propiolyl)-4-(1-methyl-imidazol-2-yl)-piperazine 0.64 ml (4.1 mmol) DIC and 0.55 g (4.1 mmol) HOBt were added to a solution of 600 mg (4.1 mmol) phenylpropiolic acid and 680 mg (4.1 mmol)
1-(1-methyl-1H-imidazol-2-yl)piperazine in DMF (3.3 ml) and the mixture was stirred for 18 h at RT. A 1 molar aq. Na$_2$CO$_3$ sol. (5 ml) was subsequently added and extracted with DCM. The organic phase was dried over MgSO$_4$, filtered and the solvent removed in a vacuum. CC (SiO$_2$, EE/MeOH 9:1) was performed with the residue, whereby 720 mg (2.4 mmol, 60%) 1-(3-phenyl-propiolyl)-4-(1-methyl-imidazol-2-yl)-piperazine was obtained.

c) Synthesis of 1-(3-phenyl-propiolyl)-4-(1-methyl-imidazol-2-yl)-piperazine hydrochloride 720 mg (2.40 mmol) 1-(3-phenyl-propiolyl)-4-(1-methyl-imidazol-2-yl)-piperazine were dissolved in acetone (20 ml) and 22 µl (1.22 mmol) water and 310 µl (2.45 mmol) trimethylchlorosilane were consecutively added. The resultant precipitation was sucked off and washed with acetone. In this process, 440 mg (1.3 mmol, 32%) 1-(3-phenyl-propiolyl)-4-(1-methyl-imidazol-2-yl)-piperazine hydrochloride was obtained.
MS: [MH$^+$] 295.1

Example 4

(R)-2-methyl-1-(3-(3-chloro-phenyl)-propiolyl)-4-(thiazol-4-yl)-piperazine

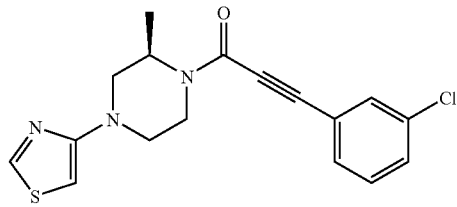

a) Synthesis of 4-bromothiazol

A solution of 10.0 g (41.2 mmol) 2,4-dibromothiazol in ether (210 ml) was cooled to −78° C. and 28.3 ml (45.3 mmol, 15% in hexane) n-butyllithium was added in drops at this temperature. After 30 min of stirring, 3.3 ml (82.3 mmol) methanol was added at −78° C. to the reaction mixture. Heating was subsequently performed to RT over a period of 16 h. The reaction mixture was filtered over silica gel and washed with a n-hexane/AE mixture (2:1). The filtrate was concentrated in a vacuum, whereby 6.7 g (40.9 mmol, 99%) 4-bromothiazol was obtained.

b) Synthesis of (R)-4-(3-methylpiperazine-1-yl)thiazol 10.0 g (100 mmol) (R)-2-methylpiperazine were fused at 100° C. 2.7 g (16.8 mmol) 4-bromothiazol was added in portions to this fusion over a period of 2 h. Stirring was subsequently performed for 18 h at 100° C. After cooling to RT, the residue was received in 10% aq. hydrochloric acid and washed with AE. Alkalic adjustment was subsequently performed with a 10% aq. NaOH sol. (pH>12) and extracted with DCM. The organic phase was dried over MgSO$_4$, filtered and concentrated in a vacuum. CC (SiO$_2$, DCM/MeOH 9:1) was performed with the residue, whereby 277 mg (1.5 mmol, 9%) (R)-4-(3-methylpiperazine-1-yl)thiazol was obtained.

c) Synthesis of (R)-2-methyl 1-(3-(3-chloro-phenyl)-propiolyl)-4-(thiazol-4-yl)-piperazine 0.23 ml (1.50 mmol) DIC and 0.20 g (1.50 mmol) HOBt were added to a solution of 270 mg (1.50 mmol) 3-(3-chloro-phenyl)propiolic acid and 270 mg (1.50 mmol) (R)-4-(3-methylpiperazine-1-yl)thiazol in DMF (1.2 ml) and the mixture was stirred for 18 h at RT. A 1 molar Na$_2$CO$_3$ sol (3 ml) was subsequently added and extracted with DCM. The organic phase was dried over MgSO$_4$, filtered and concentrated in a vacuum. CC (SiO$_2$, DCM/EE 19:1) was performed with the residue, whereby 60 mg (0.17 mmol, 12%) (R)-2-methyl 1-(3-(3-chloro-phenyl)-propiolyl)-4-(thiazol-4-yl)-piperazine was obtained.
MS: [MH$^+$] 346.1

Example 5

2-methyl 1-(3-(3-chloro-phenyl)-propiolyl)-4-(1,3,4-thiadiazol-2-yl)-piperazine

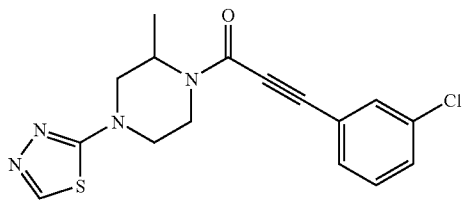

a) Synthesis of 2-(3-methylpiperazine-1-yl)-1,3,4-thiadiazol 2.0 g (12.1 mmol) 2-bromine-[1,3,4]-thiadiazol and 7.2 g (72.7 mmol) 2-methylpiperazine were stirred in n-butanol (10 ml) for 20 min at 120° C. The mixture was subsequently concentrated in a vacuum. CC (SiO$_2$, DCE/EtOH/conc. NH$_4$OH 5:1:0.06) was performed with the residue, whereby 1.7 g (9.3 mmol, 78%) 2-(3-methylpiperazine-1-yl)-1,3,4-thiadiazol was obtained.

b) Synthesis of 2-methyl 1-(3-(3-chloro-phenyl)-propiolyl)-4-(1,3,4-thiadiazol-2-yl)-piperazine 2.5 g (≅3.5 mmol) PL-EDC (polymer-bound carbodiimide resin) was added to a solution of 276 mg (1.50 mmol) 2-(3-methylpiperazine-1-yl)-1,3,4-thiadiazol and 406 mg (2.25 mmol) 3-(3-chloro-phenyl)propiolic acid in DCM (30 ml) and the reaction solution was shaken for 16 h at RT. The resin was subsequently filtered off and the filtrate was concentrated in a vacuum. CC (SiO$_2$, DCE/EtOH 10:1) was performed with the residue, whereby 140 mg (0.45 mmol, 30%) 2-(3-methylpiperazine-1-yl)-1,3,4-thiadiazol was obtained.

MS: [MH$^+$] 347.1

The synthesis of example 2 1-(3-Phenyl-propiolyl)-4-(thiazol-4-yl)-piperazine was performed according to the methods described in examples 4b) and c).

MS: [MH$^+$] 298.1

In this case, it is apparent to the person skilled in the art which starting compounds and intermediate products have to be used in each case in order to arrive at the corresponding example.

Example 6

3-(3-chlorophenyl)-N-(2-(methyl(1,3,4-thiadiazol-2-yl)amino)ethyl)propiolamide

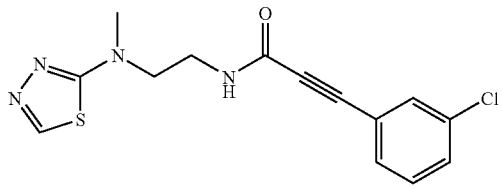

a) Synthesis of N$^1$-methyl-N$^1$-(1,3,4-thiadiazol-2-yl)ethane-1,2-diamine 70 mg (1.1 mmol) copper and 328 mg (3.3 mmol) copper(I) chloride were added to a solution of 3.3 g (20.0 mmol) 2-bromothiadiazol and 10.6 ml (120.0 mmol) N-methyl-ethylenediamine in isopropanol (114 ml). Heating was subsequently performed at 1 h to 70° C. After cooling to RT, filtration was performed through silica gel and the filtrate was concentrated in a vacuum. 1.05 g (6.6 mmol, 33%) N$^1$-methyl-N$^1$-(1,3,4-thiadiazol-2-yl)ethane-1,2-diamine was obtained by CC (DCE/EtOH/conc. aq. NH$_4$OH sol. 4:4:0.25) with the residue.

b) Synthesis of 3-(3-chlorophenyl)-N-(2-(methyl(1,3,4-thiadiazol-2-yl)amino)ethyl)propiolamide 3.25 g (≅4.0 mmol) PS carbodiimide was added to a solution of 317 mg (2.0 mmol) N$^1$-methyl-N$^1$-(1,3,4-thiadiazol-2-yl)ethane-1,2-diamine and 542 mg (3.0 mmol) 3-(3-chlorophenyl)propiolic acid in DCM (20 ml) and the reaction solution was shaken for 16 h at RT. The resin was subsequently filtered off, washed with DCM and ethanol and the filtrate concentrated in a vacuum. CC (chloroform) was performed with the residue, whereby 165 mg (0.51 mmol, 26%) 3-(3-chlorophenyl)-N-(2-(methyl(1,3,4-thiadiazol-2-yl)amino)ethyl)propiolamide was obtained.

MS: [MH$^+$] 321.0

Example 7

3-(3-chlorophenyl)-N-(2-(methyl(thiazol-5-yl)amino)ethyl)propiolamide

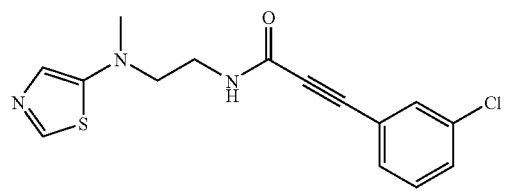

a) Synthesis of N$^1$-methyl-N$^1$-(thiazol-5-yl)ethane-1,2-diamine 37 mg (0.6 mmol) copper and 172 mg (1.7 mmol) copper(I) chloride were added to a solution of 1.15 ml (10.5 mmol) 5-bromothiazol and 5.6 ml (63.0 mmol) N-methyl-ethylenediamine in isopropanol (6 ml). Heating was subsequently performed for 1 h to 70° C. Concentration was subsequently performed in a vacuum. The residue was received with brine (40 ml) and DCM (20 ml) and the phases were separated. The organic phase was dried over MgSO$_4$, filtered and concentrated in a vacuum. CC (DCE/EtOH/conc. NH$_4$OH 5:1:0.06) was performed with the residue, whereby 104 mg (0.7 mmol, 6%) N$^1$-methyl-N$^1$-(thiazol-5-yl)ethane-1,2-diamine was obtained.

b) Synthesis of 3-(3-chlorophenyl)-N-(2-(methyl(thiazol-5-yl)amino)ethyl)propiolamide 1.5 g (≅1.8 mmol) PS carbodiimide was added to a solution of 146 mg (0.93 mmol) N$^1$-methyl-N$^1$-(thiazol-5-yl)ethane-1,2-diamine and 252 mg (1.39 mmol) 3-(3-chlorophenyl)

propiolic acid in DCM (10 ml) and the reaction solution was shaken for 16 h at RT. The resin was subsequently filtered off, washed with DCM and ethanol and the filtrate concentrated in a vacuum. CC (DCE/EtOH 10:1) was performed with the residue, whereby 63 mg (0.20 mmol, 21%) 3-(3-chlorophenyl)-N-(2-(methyl(thiazol-5-yl)amino)ethyl)propiolamide was obtained.

MS: [MH$^+$] 320.1

Example 8

3-(3-chlorophenyl)-N-(2-(methyl(1-methyl-1H-imidazol-2-yl)amino)ethyl)propiolamide

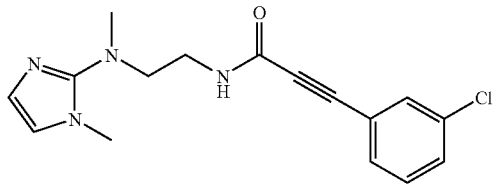

a) Synthesis of 2-iodine-1-methyl-imidazol 7.97 ml (100.0 mmol) 1-methyl-imidazol was dissolved in THF (100 ml) and cooled to −78° C. 40 ml (2.5 M in hexane, 100 mmol) BuLi was added in drops at this temperature. After the end of addition, heating was performed for 5 min to 0° C., followed immediately by cooling to −78° C. A solution of 27.9 g (110.0 mmol) iodine (I$_2$) in THF (60 ml) was added in drops at this temperature and stirring was performed for 20 min at RT. Quenching was subsequently performed with a 5% aq. Na$_2$S$_2$O$_3$ sol (120 ml) and extraction with DCM (4×50 ml). The collected organic phases were dried over MgSO$_4$, filtered and concentrated in a vacuum. 11.5 g (55.2 mmol, 55%) 2-iodine-1-methyl-imidazol was obtained by crystallisation of the residue from diethylether.

b) Synthesis of N$^1$-methyl-N$^1$-(1-methyl-1H-imidazol-2-yl)ethane-1,2-diamine A mixture of 4.8 g (23.0 mmol) 2-iodine-1-methyl-imidazol, 12.2 ml (138.0 mmol) N-methyl-ethylene-diamine, 80 mg (1.3 mmol) copper and 374 mg (3.8 mmol) copper(I) chloride was heated for 1 h to 70° C. erhitzt. After cooling to RT, the solution was received with brine and DCM and the phases were separated. The organic phase was dried over MgSO$_4$, filtered and concentrated in a vacuum. CC (DCE/EtOH/conc. aq. NH$_4$OH sol. 5:1:0.06) was performed with the residue, whereby 215 mg (1.4 mmol, 6%) N$^1$-methyl-N$^1$-(1-methyl-1H-imidazol-2-yl)ethane-1,2-diamine was obtained.

c) Synthesis of 3-(3-chlorophenyl)-N-(2-(methyl(1-methyl-1H-imidazol-2-yl)amino)ethyl)-propiolamide 2.3 g (≅2.8 mmol) PS carbodiimide was added to a solution of 215 mg (1.4 mmol) N$^1$-methyl-N$^1$-(1-methyl-1H-imidazol-2-yl)ethane-1,2-diamine and 378 mg (2.1 mmol) 3-(3-chloro-phenyl)propiolic acid in DCM (30 ml) and the reaction solution was shaken for 16 h at RT. The resin was subsequently filtered off, washed with DCM and ethanol and the filtrate concentrated in a vacuum. CC (DCE/EtOH 5:1) was performed with the residue, whereby 241 mg (0.8 mmol, 54%) 3-(3-chlorophenyl)-N-(2-(methyl(1-methyl-1H-imidazol-2-yl)amino)ethyl)-propiolamide was obtained.

MS: [MH$^+$] 317.1

Pharmacological Data:

1. The affinity of the substituted propiolic acid amides according to the invention of the general formula I to the mGluR5 receptor was determined as described above (method I and II).

The substituted propiolic acid amides according to the invention exhibit an outstanding affinity to the mGluR5 receptor.

The pharmacological data of substituted propiolic acid amides is reproduced in the following table 1:

| Ex. | K$_i$ mGluR5 receptor (human) Ca$^{2+}$ influx [nM] | IC$_{50}$ mGluR5 receptor (pig) [$^3$H]-MPEP bond [µM] |
| --- | --- | --- |
| 1 | | 1.890 |
| 2 | | 0.630 |
| 3 | | 4.840 |
| 4 | 0.0033 | 0.016 |
| 5 | 0.0048 | 0.027 |
| 6 | | 0.0210 |
| 7 | 0.0008 | 0.0005 |
| 8 | | 0.3500 |

2. The substituted propiolic acid amides according to the invention exhibit an effective inhibition of the pain reaction in the formaline test in rats in the case of an i.v. administration of 21.5 mg/kg.

| Ex. | Formaline test (rat) i.v. Reduction in nociceptive behaviour over control at 10 mg/kg [%] |
| --- | --- |
| 4 | 75 |

The invention claimed is:

1. A substituted propiolic acid amide of the formula I,

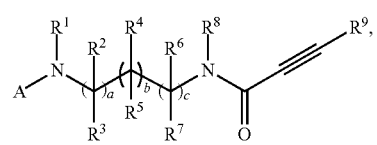

in which a, b and c, mutually independently, in each case denote 0 or 1, wherein the sum of a, b and c is equal to 1, 2 or 3;

A denotes one of the following residues

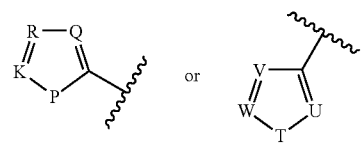

Q and U respectively denote CR$^{10}$ or N;
R and V respectively denote CR$^{11}$ or N;
K and W respectively denote CR$^{12}$ or N;
P and T respectively denote O, S or NR$^{13}$;

with the proviso that compounds are excluded in which P denotes S, Q denotes N, R denotes $CR^{11}$ and K denotes $CR^{12}$ or N;

$R^1$ and $R^8$, mutually independently, in each case denote H; —C(=O)—$R^{28}$; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)- cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl or -(heteroalkenylene)-heteroaryl;

$R^2$, $R^3$, $R^4$, $R^5$, $R^6$, $R^7$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$, mutually independently, in each case denote H; F; Cl; Br; I; —$NO_2$; —CN; —$NH_2$; —OH; —SH; —C(=O)—OH; —C(=O)—H; —NH—C(=O)—H; —C(=O)—$R^{28}$; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; —NH—$R^{35}$; —$NR^{36}R^{37}$; —O—C(=O)—$R^{38}$; —NH—C(=O)—$R^{39}$; —$NR^{40}$—C(=O)—$R^{41}$; —O—$R^{42}$, —S—$R^{43}$; —NH—C(=O)—NH—$R^{44}$; —NH—C(=S)—NH—$R^{45}$; —NH—S(=O)$_2$—$R^{46}$; —$NR^{47}$—S(=O)$_2$—$R^{48}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted -(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl;

or $R^2$ and $R^3$ or $R^4$ and $R^5$ or $R^6$ and $R^7$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$, mutually independently, jointly denote a residue selected from the group consisting of an oxo group (=O) and a thioxo group (=S);

or $R^1$ and $R^8$ together with the —N—$CR^2R^3$—$(CR^4R^5)_b$—$(CR^6R^7)_c$ group joining them together form a residue of the formula B,

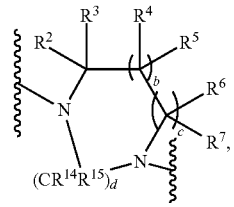

B wherein d denotes 1, 2 or 3 and b denotes 0 or 1 and c denotes 0 or 1;

or $R^1$ and R2 together with the —N—$CR^3$ group joining them together form a residue of the formula C,

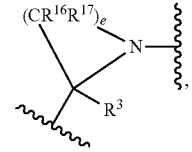

C wherein e denotes 1, 2, 3 or 4 and, in this case, b denotes 0 or 1 and c denotes 0;

or $R^1$ and $R^4$ together with the —N—$CR^2R^3$—$CR^5$ group joining them together form a residue of the formula D,

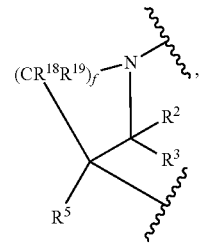

D wherein f denotes 1, 2, 3 or 4, and, in this case, c denotes 0;

or $R^1$ and $R^6$ together with the —N—$CR^2R^3$—$CR^4R^5$—$CR^7$ group joining them together form a residue of the formula E,

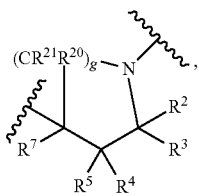

E wherein g denotes 1, 2 or 3;
or $R^6$ and $R^8$ together with the —N—$CR^7$ group joining them together form a residue of the formula F

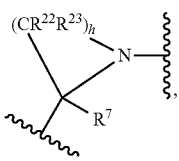

F wherein h denotes 1, 2, 3 or 4 and, in this case, b denotes 0 or 1 and a denotes 0;
or $R^4$ and $R^8$ together with the —N—$CR^6R^7$—$CR^5$ group joining them together form a residue of the formula G,

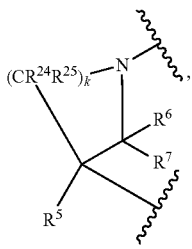

G wherein k denotes 1, 2, 3 or 4, and, in this case, a denotes 0;
or $R^2$ and $R^8$ together with the —N—$CR^6R^7$—$CR^4R^5$—$CR^3$ group joining them together form a residue of the formula H,

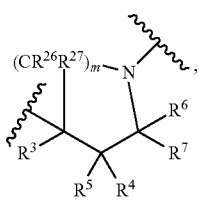

H wherein m denotes 1, 2 or 3;
$R^9$ denotes unsubstituted or substituted aryl or unsubstituted or substituted heteroaryl;
$R^{10}$, $R^{11}$ and $R^{12}$, mutually independently, in each case denote H; F; Cl; Br; I; —$NO_2$; —CN; —$NH_2$; —OH; —SH; —C(=O)—OH; —C(=O)—H; —NH—C(=O)—H; —C(=O)—$R^{28}$; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; —NH—$R^{35}$; —$NR^{36}R^{37}$; —O—C(=O)—$R^{38}$; —NH—C(=O)—$R^{39}$; —$NR^{40}$—C(=O)—$R^{41}$; —O—$R^{42}$; —S—$R^{43}$; —NH—C(=O)—NH—$R^{44}$; —NH—C(=S)—NH—$R^{45}$; —NH—S(=O)$_2$—$R^{46}$; —$NR^{47}$—S(=O)$_2$—$R^{48}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted -(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl;

$R^{13}$ denotes H; —C(=O)—OH; —C(=O)—H; —C(=O)—$R^{28}$; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted -(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl;

and $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$, mutually independently, in each case denote unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;

in each case optionally in the form of one of the pure stereoisomers thereof, in the form of one of the racemates thereof or in the form of a mixture of stereoisomers in any mixing ratio, or in each case in the form of a corresponding salt.

2. A compound according to claim 1, wherein
a, b and c, mutually independently, in each case denote 0 or 1, wherein the sum of a, b and c is equal to 1, 2 or 3;
A denotes one of the following residues

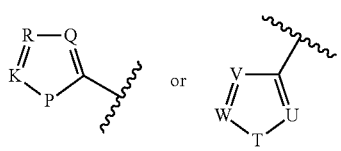

Q and U respectively denote $CR^{10}$ or N;
R and V respectively denote $CR^{11}$ or N;
K and W respectively denote $CR^{12}$ or N;
P and T respectively denote O, S or $NR^{13}$;
with the proviso that compounds are excluded in which P denotes S, Q denotes N, R denotes $CR^{11}$ and K denotes $CR^{12}$ or N;
$R^1$ and $R^8$, mutually independently, in each case denote H; —C(=O)—$R^{28}$; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)- cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;

$R^2$, $R^3$, $R^4$, $R^5$, $R^6$, $R^7$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$, mutually independently, in each case denote H; F; Cl; Br; I; —$NO_2$; —CN; —$NH_2$; —OH; —SH; —C(=O)—OH; —C(=O)—H; —NH—C(=O)—H; —C(=O)—$R^{28}$; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; —NH—$R^{35}$; —$NR^{36}R^{37}$; —O—C(=O)—$R^{38}$; —NH—C(=O)—$R^{39}$; —$NR^{40}$—C(=O)—$R^{41}$; —O—$R^{42}$; —S—$R^{43}$; —NH—C(=O)—NH—$R^{44}$; —NH—C(=S)—NH—$R^{45}$; —NH—S(=O)$_2$—$R^{46}$; —$NR^{47}$—S(=O)$_2$—$R^{48}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted -(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl;

or $R^2$ and $R^3$ or $R^4$ and $R^5$ or $R^6$ and $R^7$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$, mutually independently, jointly denote a residue selected from the group consisting of an oxo group (=O) and a thioxo group (=S);

or $R^1$ and $R^8$ together with the —N—$CR^2R^3$—$(CR^4R^5)_b$—$(CR^6R^7)_c$ group joining them together form a residue of the formula B,

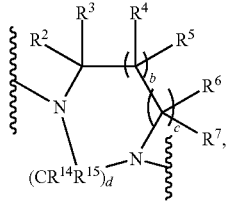

B wherein d denotes 1, 2 or 3 and b denotes 0 or 1 and c denotes 0 or 1;

or $R^1$ and $R^2$ together with the —N—$CR^3$ group joining them together form a residue of the formula C,

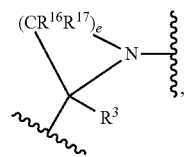

C wherein e denotes 1, 2, 3 or 4 and, in this case, b denotes 0 or 1 and c denotes 0;

or $R^1$ and $R^4$ together with the —N—$CR^2R^3$—$CR^5$ group joining them together form a residue of the formula D,

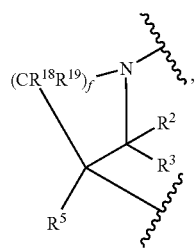

D wherein f denotes 1, 2, 3 or 4, and, in this case, c denotes 0;

or $R^1$ and $R^6$ together with the —N—$CR^2R^3$—$CR^4R^5$—$CR^7$ group joining them together form a residue of the formula E,

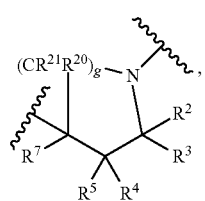

E wherein g denotes 1, 2 or 3;

or $R^6$ and $R^8$ together with the —N—$CR^7$ group joining them together form a residue of the formula F

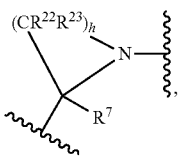

F wherein h denotes 1, 2, 3 or 4 and, in this case, b denotes 0 or 1 and a denotes 0;

or $R^4$ and $R^8$ together with the —N—$CR^6R^7$—$CR^5$ group joining them together form a residue of the formula G,

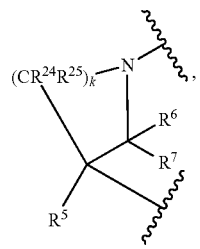

G wherein k denotes 1, 2, 3 or 4, and, in this case, a denotes 0;

or $R^2$ and $R^8$ together with the —N—$CR^6R^7$—$CR^4R^5$—$CR^3$ group joining them together form a residue of the formula H,

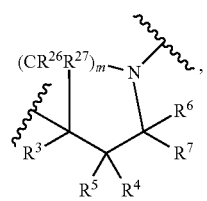

H wherein m denotes 1, 2 or 3;

$R^9$ denotes unsubstituted or substituted aryl or unsubstituted or substituted heteroaryl;

$R^{10}$, $R^{11}$ and $R^{12}$, mutually independently, in each case denote H; F; Cl; Br; I; —$NO_2$; —CN; —$NH_2$; —OH; —SH; —C(=O)—OH; —C(=O)—H; —NH—C(=O)—H; —C(=O)—$R^{28}$; —C(=O)—O—$R^{29}$; —C(=O)—$NH_2$; —C(=O)—NH—$R^{30}$; —C(=O)—$NR^{31}R^{32}$; —S(=O)—$R^{33}$; —S(=O)$_2$—$R^{34}$; —NH—$R^{35}$; —$NR^{36}R^{37}$; —O—C(=O)—$R^{38}$; —NH—C(=O)—$R^{39}$; —$NR^{40}$—C(=O)—$R^{41}$; —O—$R^{42}$; —S—$R^{43}$; —NH—C(=O)—NH—$R^{44}$; —NH—C(=S)—NH—$R^{45}$; —NH—S(=O)$_2$—$R^{46}$; —$NR^{47}$—S(=O)$_2$—$R^{48}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted -(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl;

$R^{13}$ denotes H; —C(=O)—OH; —C(=O)—H; —C(=O)—$R^{28}$; —C(=O)—O—$R^{29}$; —C(=O)—NH$_2$; —C(=O)—NH—$R^{30}$; —C(=O)—NR$^{31}$R$^{32}$; —S(=O)—$R^{33}$; —S(=O)$_2$—$R^{34}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted -(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted -(alkylene)-aryl, -(alkenylene)-aryl, -(alkynylene)-aryl, -(heteroalkylene)-aryl or -(heteroalkenylene)-aryl; or unsubstituted or at least monosubstituted -(alkylene)-heteroaryl, -(alkenylene)-heteroaryl, -(alkynylene)-heteroaryl, -(heteroalkylene)-heteroaryl or -(heteroalkenylene)-heteroaryl;

and $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$, mutually independently, in each case denote unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;

wherein the above-mentioned alkyl residues are in each case branched or straight-chained and have 1, 2, 3, 4, 5, 6, 7, 8, 9, 10, 11 or 12 carbon atoms as chain members;

the above-mentioned alkenyl residues are in each case branched or straight-chained and have 2, 3, 4, 5, 6, 7, 8, 9, 10, 11 or 12 carbon atoms as chain members;

the above-mentioned alkynyl residues are in each case branched or straight-chained and have 2, 3, 4, 5, 6, 7, 8, 9, 10, 11 or 12 carbon atoms as chain members;

the above-mentioned heteroalkyl residues, heteroalkenyl residues and heteroalkynyl residues are in each case 2-, 3-, 4-, 5-, 6-, 7-, 8-, 9-, 10-, 11- or 12-membered;

the above-mentioned heteroalkyl residues, heteroalkenyl residues and heteroalkynyl residues in each case have optionally 1, 2 or 3 heteroatom(s) mutually independently selected from the group consisting of oxygen, sulphur and nitrogen as the chain member(s);

the above-mentioned alkyl residues, alkenyl residues, alkynyl residues, heteroalkyl residues, heteroalkenyl residues and heteroalkynyl residues can in each case be substituted with optionally 1, 2, 3, 4 or 5 substituents mutually independently selected from the group consisting of F, Cl, Br, I, —NO$_2$, —CN, —OH, —SH, —NH$_2$, —N(C$_{1-5}$-alkyl)$_2$, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, wherein the phenyl residues can be substituted with 1, 2, 3, 4 or 5 substituents mutually independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl;

the above-mentioned cycloalkyl residues in each case have 3, 4, 5, 6, 7, 8 or 9 carbon atoms as ring members;

the above-mentioned cycloalkenyl residues in each case have 3, 4, 5, 6, 7, 8 or 9 carbon atoms as ring members;

the above-mentioned heterocycloalkyl residues are in each case 3-, 4-, 5-, 6-, 7-, 8- or 9-membered;

the above-mentioned heterocycloalkenyl residues are in each case 4-, 5-, 6-, 7-, 8- or 9-membered;

the above-mentioned heterocycloalkyl residues and heterocycloalkenyl residues in each case have optionally 1, 2 or 3 heteroatom(s) mutually independently selected from the group consisting of oxygen, sulphur and nitrogen (NH) as the ring member(s);

the above-mentioned cycloalkyl residues, heterocycloalkyl residues, cycloalkenyl residues or heterocycloalkenyl residues can in each case be substituted with optionally 1, 2, 3, 4 or 5 substituents mutually independently selected from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl, —C(=O)—CF$_3$, —S(=O)$_2$—C$_{1-5}$-alkyl, —S(=O)—C$_{1-5}$-alkyl, —S(=O)$_2$-phenyl, oxo (=O), thioxo (=S), —N(C$_{1-5}$-alkyl)$_2$, —N(H)(C$_{1-5}$-alkyl), —NO$_2$, —S—CF$_3$, —C(=O)—OH, —NH—C(=O)—C$_{1-5}$-alkyl, —C(=O)—H, —C(=O)—C$_{1-5}$-alkyl, —C(=O)—NH$_2$, —C(=O)—N(C$_{1-5}$-alkyl)$_2$, —C(=O)—N(H)(C$_{1-5}$-alkyl) and phenyl, wherein the phenyl residues can respectively be unsubstituted or substituted with 1, 2, 3, 4 or 5 substituents mutually independently selected from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkenyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl and —C(=O)—CF$_3$, wherein the above-mentioned phenyl residues can optionally be substituted with 1, 2, 3, 4 or 5 substituents mutually independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl;

the above-mentioned alkylene residues are in each case branched or straight-chained and have 1, 2, 3, 4, 5, 6, 7, 8, 9, 10, 11 or 12 carbon atoms as chain members;

the above-mentioned alkenylene residues are in each case branched or straight-chained and have 2, 3, 4, 5, 6, 7, 8, 9, 10, 11 or 12 carbon atoms as chain members;

the above-mentioned alkynylene residues are in each case branched or straight-chained and have 2, 3, 4, 5, 6, 7, 8, 9, 10, 11 or 12 carbon atoms as chain members;

the above-mentioned heteroalkylene residues and heteroalkenylene residues are in each case 2-, 3-, 4-, 5-, 6-, 7-, 8-, 9-, 10-, 11- or 12-membered;

the above-mentioned heteroalkylene and heteroalkenylene groups have in each case optionally 1, 2 or 3 heteroatom(s) mutually independently selected from the group consisting of oxygen, sulphur and nitrogen (NH) as the chain member(s);

the above-mentioned alkylene, alkenylene, alkynylene, heteroalkylene or heteroalkenylene group can in each case be unsubstituted or substituted with optionally 1, 2, 3, 4 or 5 substituents mutually independently selected from the group consisting of phenyl, F, Cl, Br, I, —NO$_2$, —CN, —OH, —O-phenyl, —O—CH$_2$-phenyl, —SH, —S-phenyl, —S—CH$_2$-phenyl, NH$_2$, —N(C$_{1-5}$-alkyl)$_2$, —NH-phenyl, —N(C$_{1-5}$-alkyl) (phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, wherein the phenyl residues can be substituted with 1, 2, 3, 4 or 5 substituents mutually independently selected from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

the above-mentioned aryl residues are mono- or bicyclic and have 6, 10 or 14 carbon atoms;

the above-mentioned heteroaryl residues are mono-, bi- or tricyclic and 5-, 6-, 7-, 8-, 9-, 10-, 11-, 12-, 13- or 14-membered;

the above-mentioned 5- to 14-membered heteroaryl residues in each case have optionally 1, 2, 3, 4 or 5 heteroatom(s) mutually independently selected from the group consisting of oxygen, sulphur and nitrogen (NH) as the ring member(s);

and the above-mentioned aryl residues and heteroaryl residues can in each case be substituted with optionally 1, 2, 3, 4 or 5 substituents mutually independently selected from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, N(C$_{1-5}$-alkyl)$_2$, —C(=O)—O—C$_{1-5}$-alkyl, —C(=O)—O-phenyl, —C(=O)—H, —C(=O)—C$_{1-5}$-alkyl, —CH$_2$—O—C(=O)-phenyl, —O—C(=O)-phenyl, —O—C(=O)—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, —C(=O)—N(C$_{1-5}$-alkyl)(phenyl), —C(=O)—NH-phenyl, cyclopropyl, cyclobutyl, cyclopentyl, cyclohexyl, pyrazolyl, phenyl, furyl (furanyl), thiazolyl, thiadiazolyl, thiophenyl (thienyl), benzyl and phenethyl, wherein the cyclic substituents or the cyclic residues of these substituents themselves can be substituted with optionally 1, 2, 3, 4 or 5 substituents mutually independently selected from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

in each case optionally in the form of one of the pure stereoisomers thereof, in the form of one of the racemates thereof or in the form of a mixture of stereoisomers in any mixing ratio, or in each case in the form of a corresponding salt.

3. A compound according to claim 1, wherein A denotes a residue selected from the group consisting of

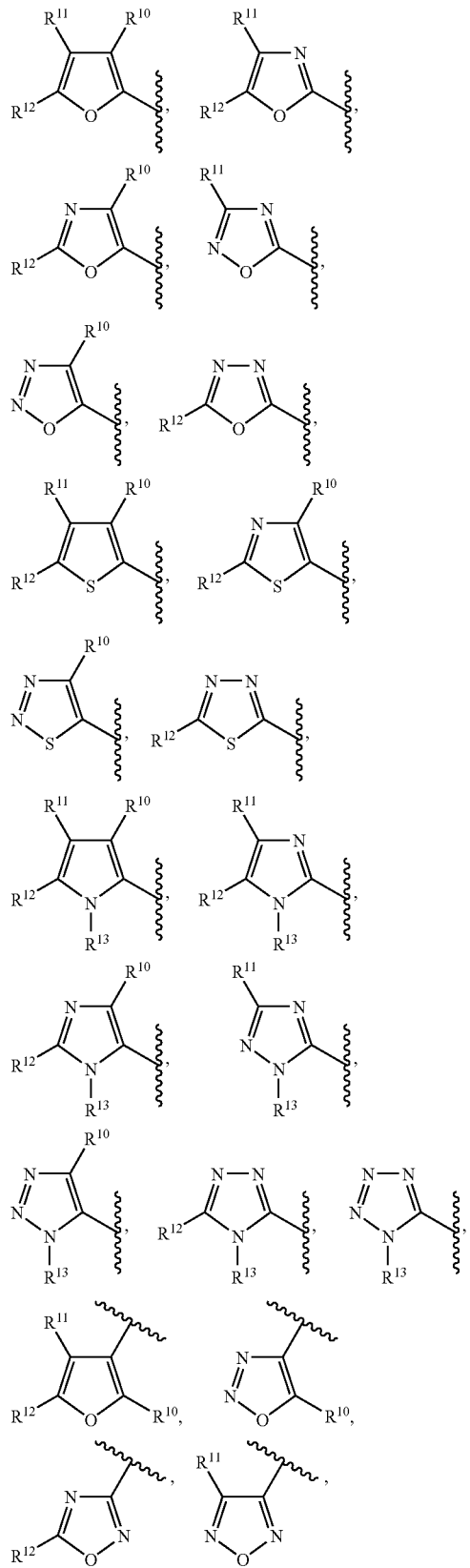

4. A compound according to claim 1, wherein
R$^1$ and R$^8$, mutually independently, in each case denote H; —C(=O)—R$^{28}$; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; C$_{1-6}$-alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$;

C$_{3-8}$-cycloalkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$;

or a phenyl residue, which can be bound in each case via a C$_{1-3}$-alkylene-, C$_{2-3}$-alkenylene - or C$_{2-3}$-alkynylene group or is unsubstituted or substituted with 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$.

5. A compound according to claim 1, wherein $R^2$, $R^3$, $R^4$, $R^5$, $R^6$, $R^7$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$, mutually independently, in each case denote H; F; Cl; Br; I; —NO$_2$; —CN; —NH$_2$; —OH; —SH; —C(=O)—OH; —C(=O)—R$^{28}$; —O(=O)—O—R$^{29}$; —NH—R$^{35}$; —NR$^{36}$R$^{37}$; —O—R$^{42}$; —S—R$^{43}$; C$_{1-6}$-alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-7}$-cycloalkyl, C$_{5-6}$-cycloalkenyl, 5- to 7-membered heterocycloalkyl or 5- to 7-membered heterocycloalkenyl, which can be bound in each case via a C$_{1-3}$-alkylene-, C$_{2-3}$-alkenylene- or C$_{2-3}$-alkynylene group or unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denote a residue selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, chinolinyl, isochinolinyl and chinazolinyl, which can be bound in each case via a C$_{1-3}$-alkylene, C$_{2-3}$-alkenylene or C$_{2-3}$ alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

or $R^2$ and $R^3$ or $R^4$ and $R^5$ or $R^6$ and $R^7$ or $R^{14}$ and $R^{15}$ or $R^{16}$ and $R^{17}$ or $R^{18}$ and $R^{19}$ or $R^°$ and $R^{21}$ or $R^{22}$ and $R^{23}$ or $R^{24}$ and $R^{25}$ or $R^{26}$ and $R^{27}$, mutually independently, jointly in each case denote a residue selected from the group consisting of an oxo group (=O) and a thioxo group (=S).

6. A compound according to claim 1, wherein $R^1$ and $R^8$ together with the —N—CR$^2$R$^3$—(CR$^4$R$^5$)$_b$—(CR$^6$R$^7$)$_c$ group joining them together form a residue selected from the group consisting of

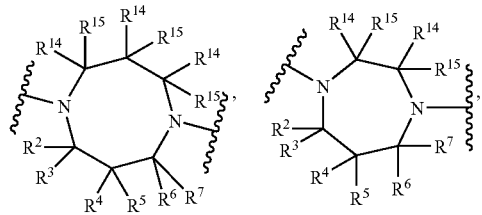,

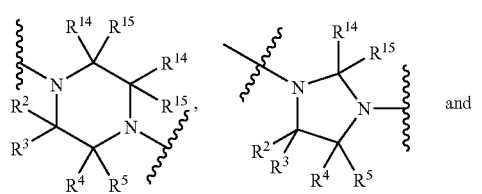 and

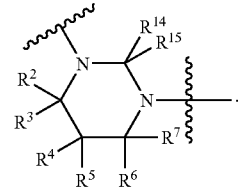.

7. A compound according to claim 1, wherein $R^1$ and $R^2$ together with the —N—CR$^3$ group joining them together form a residue selected from the group consisting of

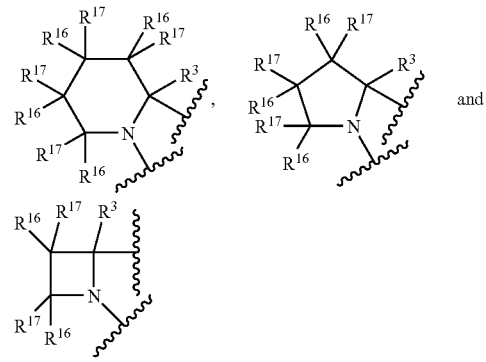

wherein, in this case, b denotes and c denotes 0.

8. A compound according to claim 1, wherein $R^1$ and $R^4$ together with the —N—CR$^2$R$^3$—CR$^5$ group joining them together form a residue selected from the group consisting of

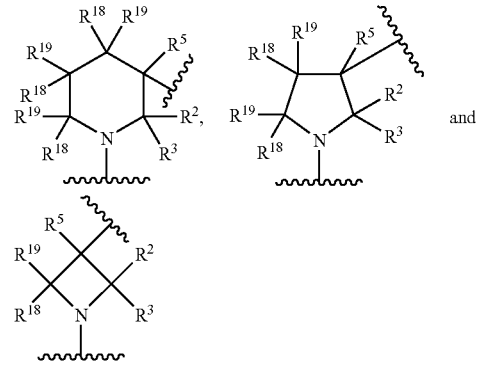

wherein, in this case, c denotes 0.

9. A compound according to claim 1, wherein $R^1$ and $R^6$ together with the —N—CR$^2$R$^3$—CR$^4$R$^5$—CR$^7$ group joining them together form a residue selected from the group consisting of

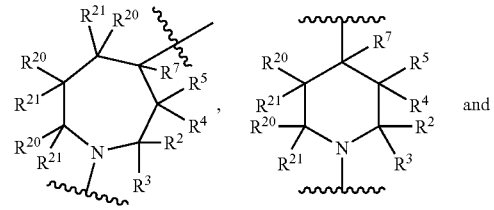 and

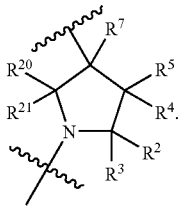

10. A compound according to claim 1, wherein $R^6$ and $R^8$ together with the —N—$CR^7$ group joining them together form a residue selected from the group consisting of

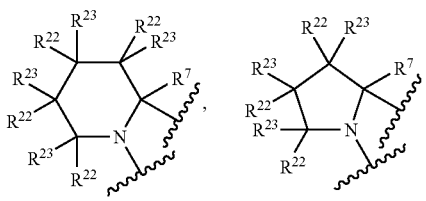

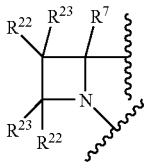

wherein, in this case, b denotes 1 and a denotes 0.

11. A compound according to claim 1, wherein $R^4$ and $R^8$ together with the —N—$CR^6R^7$—$CR^5$ group joining them together form a residue selected from the group consisting of

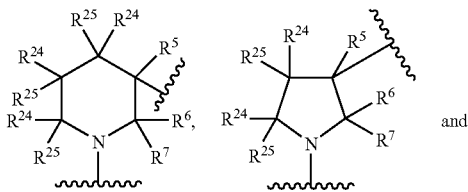

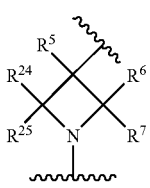

wherein, in this case, a denotes 0.

12. A compound according to claim 1, wherein $R^2$ and $R^8$ together with the —N—$CR^6R^7$—$CR^4R^5$—$CR^3$ group joining them together form a residue selected from the group consisting of

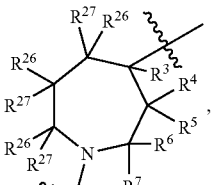, 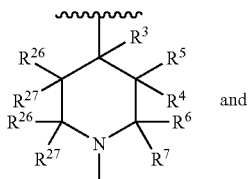 and

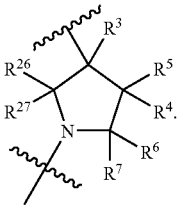

13. A compound according to claim 1, wherein
$R^9$ denotes a residue selected from the group consisting of phenyl, naphthyl, anthracenyl, furyl, thienyl, pyrazolyl, pyrazinyl, pyrimidinyl, pyridazinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, chinolinyl, isochinolinyl and chinazolinyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, cyclopropyl, cyclobutyl, cyclopentyl, cyclohexyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl.

14. A compound according to claim 1, wherein $R^{10}$, $R^{11}$ and $R^{12}$, mutually independently, in each case denote H; F; Cl; Br; I; —NO$_2$; —CN; —NH$_2$; —OH; —SH; —C(=O)—OH; —C(=O)—H; —NH—C(=O)—H; —C(=O)—R$^{28}$; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; —NH—R$^{35}$; —NR$^{36}$R$^{37}$; —O—C(=O)—R$^{38}$; —NH—C(=O)—R$^{39}$; —NR$^{40}$—C(=O)—R$^{41}$; —O—R$^{42}$; —S—R$^{43}$—NH—C(=O)—NH—R$^{44}$; —NH—C(=S)—NH—R$^{45}$; —NH—S(=O)$_2$—R$^{46}$; —NR$^{47}$—S(=O)$_2$—R$^{48}$; C$_{1-6}$-alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{2-6}$-alkenyl; C$_{2-6}$-alkynyl; C$_{3-7}$-cycloalkyl, C$_{5-6}$-cycloalkenyl, 5- to 7-membered heterocycloalkyl or 5- to 7-membered heterocycloalkenyl, which can in each case be bound via a C$_{1-3}$-alkylene, C$_{2-3}$-alkenylene or C$_{2-3}$-alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denote a residue selected from the group consisting of phenyl, naphthyl, anthracenyl, thienyl, furyl, pyridinyl, thiazolyl, thiadiazolyl, oxazolyl, oxadiazolyl and isoxazolyl, which in each case can be bound via a C$_{1-3}$-alkylene-, C$_{2-3}$-alkenylene- or C$_{2-3}$-alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$.

15. A compound according to claim 1, wherein
R$^{13}$ denotes H; —C(=O)—R$^{28}$; —C(=O)—H; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; C$_{1-6}$-alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-7}$-cycloalkyl, C$_{5-6}$-cycloalkenyl, 5- to 7-membered heterocycloalkyl or 5- to 7-membered heterocycloalkenyl, which in each case can be bound via a C$_{1-3}$-alkylene, C$_{2-3}$-alkenylene or C$_{2-3}$-alkynylene group or is unsubstituted or is substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denotes a residue selected from the group consisting of phenyl, naphthyl, anthracenyl, thienyl, furyl, pyridinyl, thiazolyl, thiadiazolyl, oxazolyl, oxadiazolyl and isoxazolyl, which in each case can be bound via a C$_{1-3}$-alkylene, C$_{2-3}$-alkenylene or C$_{2-3}$-alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$.

16. A compound according to claim 1, wherein
R$^{28}$, R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$ and R$^{48}$, mutually independently, in each case denote C$_{1-6}$-alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-7}$-cycloalkyl, C$_{5-6}$-cycloalkenyl, 5- to 7-membered heterocycloalkyl or 5- to 7-membered heterocycloalkenyl, which can in each case be bound via a C$_{1-3}$-alkylene, C$_{2-3}$-alkenylene or C$_{2-3}$-alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denote a residue selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, chinolinyl, isochinolinyl and chinazolinyl, which in each case can be bound via a C$_{1-3}$-alkylene, C$_{2-3}$-alkenylene or C$_{2-3}$-alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —NH—S(=O)$_2$—CH$_3$, —C(=O)—OH, —C(=O)—CH$_3$, —C(=O)—C$_2$H$_5$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$ and —C(=O)—O—C$_2$H$_5$.

17. A compound according to claim 1, wherein a, b and c, mutually independently, in each case denote 0 or 1, wherein the sum of a, b and c is equal to 1, 2 or 3;

A denotes a residue selected from the group consisting of

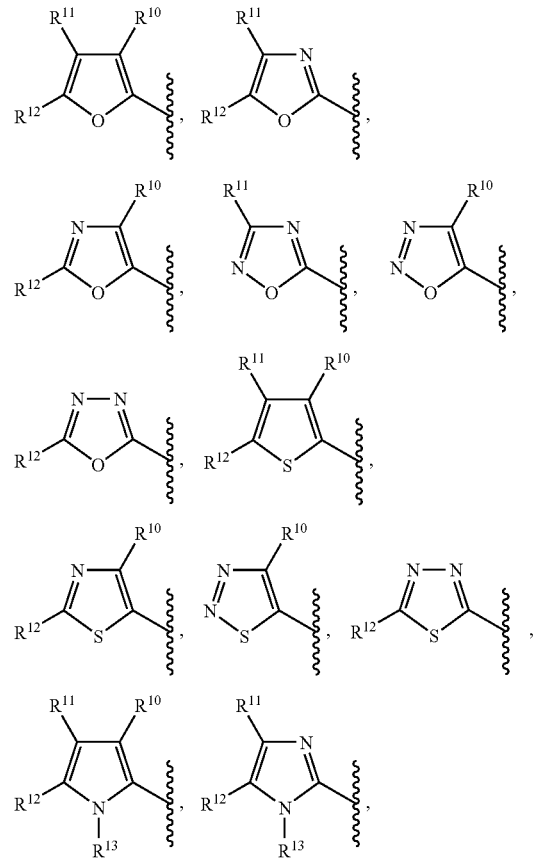

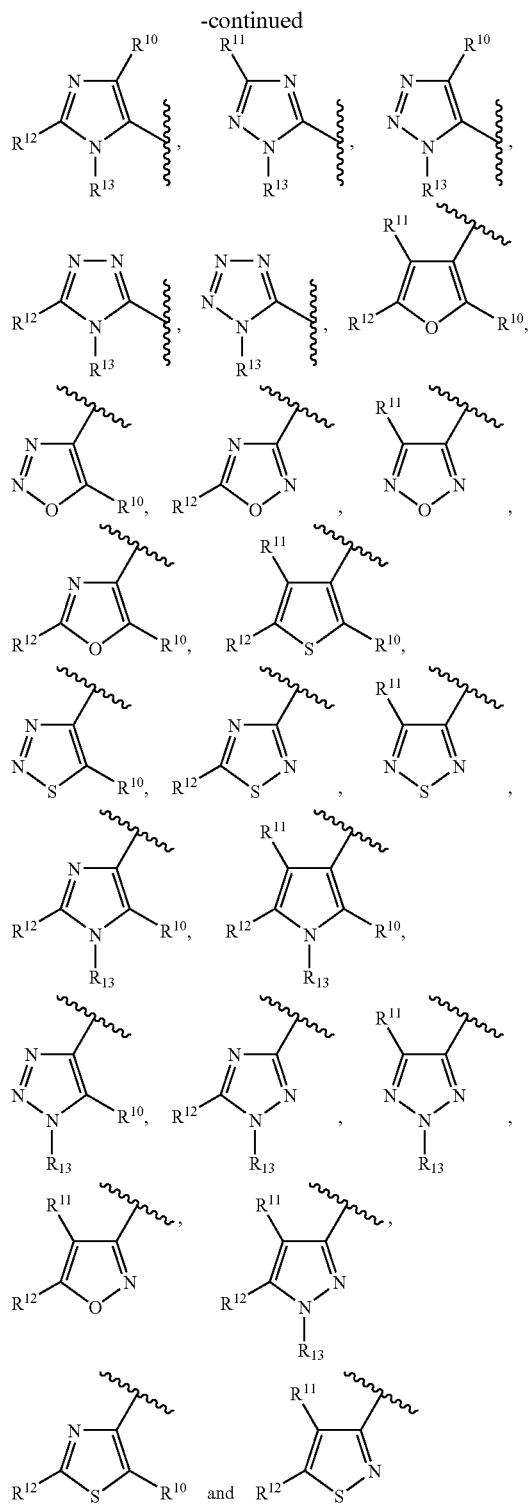

stituents mutually independently selected from the group consisting of F, Cl, Br, I, —NO$_2$, —CN, —OH, —SH and —NH$_2$;

or a phenyl residue, which can be bound in each case via a C$_{1-3}$-alkylene-, C$_{2-3}$-alkenylene - or C$_{2-3}$-alkynylene group or is unsubstituted or substituted with 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

R$^2$, R$^3$, R$^4$, R$^5$, R$^6$, R$^7$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$ and R$^{27}$, mutually independently, in each case denote H; F; Cl; Br; I; —NO$_2$; —CN; —NH$_2$; —OH; —SH; —C(=O)—OH; —C(=O)—R$^{28}$; —C(=O)—O—R$^{29}$; —NH—R$^{35}$; —NR$^{36}$R$^{37}$; —O—R$^{42}$; —S—R$^{43}$; C$_{1-6}$-alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-7}$-cycloalkyl, C$_{5-6}$-cycloalkenyl, 5- to 7-membered heterocycloalkyl or 5- to 7-membered heterocycloalkenyl, which can be bound in each case via a C$_{1-3}$-alkylene-, C$_{2-3}$-alkenylene- or C$_{2-3}$-alkynylene group or unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denote a residue selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, chinolinyl, isochinolinyl and chinazolinyl, which can be bound in each case via a C$_{1-3}$-alkylene, C$_{2-3}$-alkenylene or C$_{2-3}$ alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

or R$^2$ and R$^3$ or R$^4$ and R$^5$ or R$^6$ and R$^7$ or R$^{14}$ and R$^{15}$ or R$^{16}$ and R$^{17}$ or R$^{18}$ and R$^{19}$ or R$^o$ and R$^{21}$ or R$^{22}$ and R$^{23}$ or R$^{24}$ and R$^{25}$ or R$^{26}$ and R$^{27}$, mutually independently, jointly in each case denote a residue selected from the group consisting of an oxo group (=O) and a thioxo group (=S);

or R$^1$ and R$^8$ together with the —N—CR$^2$R$^3$—(CR$^4$R$^5$)$_b$— (CR$^6$R$^7$)$_c$ group joining them together form a residue selected from the group consisting of R$^1$ and R$^8$, mutually independently, in each case denote H; —C(=O)—R$^{28}$; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; C$_{1-6}$-alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-8}$-cycloalkyl, which is unsubstituted or substituted with optionally 1, 2, 3, 4 or 5 sub-

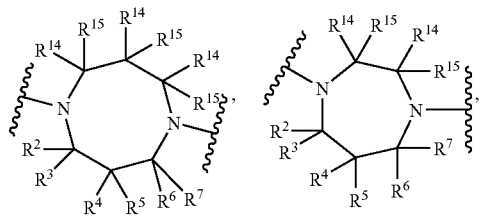

-continued

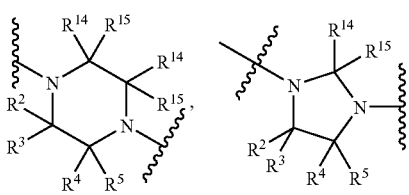

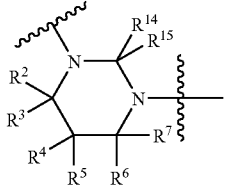

or R¹ and R² together with the —N—CR³ group joining them together form a residue selected from the group consisting of

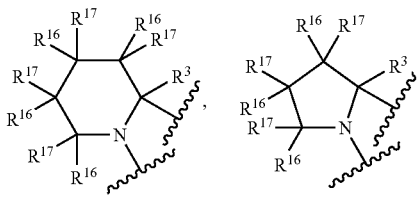

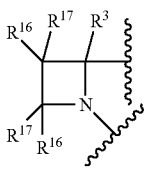

wherein, in this case, b denotes 1 and c denotes 0;
or R¹ and R⁴ together with the —N—CR²R³—CR⁵ group joining them together form a residue selected from the group consisting of

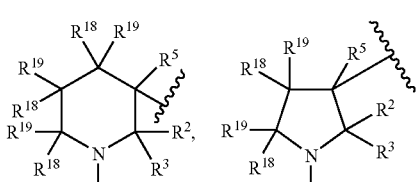

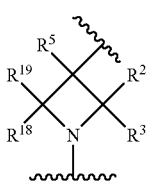

wherein, in this case, c denotes 0;
R¹ and R⁶ together with the —N—CR²R³—CR⁴R⁵ group joining them together form a residue selected from the group consisting of

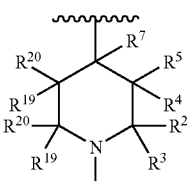 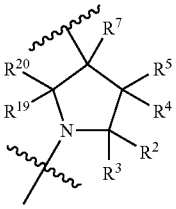

or R⁶ and R⁸ together with the —N—CR⁷ group joining them together form a residue selected from the group consisting of

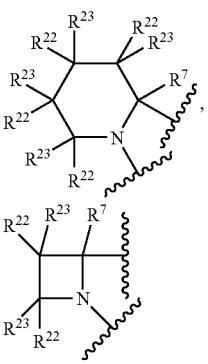 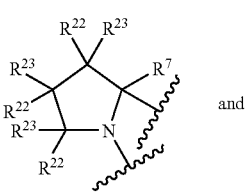

wherein, in this case, b denotes 1 and a denotes 0;
or R⁴ and R⁸ together with the —N—CR⁶R⁷—CR⁵ group joining them together form a residue selected from the group consisting of

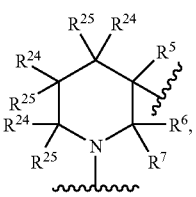 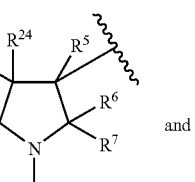

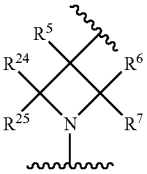

wherein, in this case, a denotes 0;
or R² and R⁸ together with the —N—CR⁶R⁷—CR⁴R⁵—CR³ group joining them together form a residue selected from the group consisting of

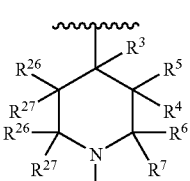 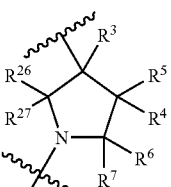

$R^9$ denotes a residue selected from the group consisting of phenyl, naphthyl, anthracenyl, furyl, thienyl, pyrazolyl, pyrazinyl, pyrimidinyl, pyridazinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, chinolinyl, isochinolinyl and chinazolinyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, cyclopropyl, cyclobutyl, cyclopentyl, cyclohexyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

$R^{10}$, $R^{11}$ and $R^{12}$, mutually independently, in each case denote H; F; Cl; Br; I; —NO$_2$; —CN; —NH$_2$; —OH; —SH; —C(=O)—OH; —C(=O)—H; —NH—C(=O)—H; —C(=O)—R$^{28}$; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; —NH—R$^{35}$; —NR$^{36}$R$^{37}$; —O—C(=O)—R$^{38}$; —NH—C(=O)—R$^{39}$; —NR$^{40}$—C(=O)—R$^{41}$; —O—R$^{42}$; —S—R$^{43}$—NH—C(=O)—NH—R$^{44}$; —NH—C(=S)—NH—R$^{45}$; —NH—S(=O)$_2$—R$^{46}$; —NR$^{47}$—S(=O)$_2$—R$^{48}$; C$_{1-6}$-alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{2-6}$-alkenyl; C$_{2-6}$-alkynyl; C$_{3-7}$-cycloalkyl, C$_{5-6}$-cycloalkenyl, 5- to 7-membered heterocycloalkyl or 5- to 7-membered heterocycloalkenyl, which can in each case be bound via a C$_{1-3}$-alkylene, C$_{2-3}$-alkenylene or C$_{2-3}$-alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH; —S—CH$_3$ and —S—C$_2$H$_5$; or denote a residue selected from the group consisting of phenyl, naphthyl, anthracenyl, thienyl, furyl, pyridinyl, thiazolyl, thiadiazolyl, oxazolyl, oxadiazolyl and isoxazolyl, which in each case can be bound via a C$_{1-3}$-alkylene-, C$_{2-3}$-alkenylene- or C$_{2-3}$-alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$;

$R^{13}$ denotes H; —C(=O)—R$^{28}$; —C(=O)—H; —C(=O)—O—R$^{29}$; —C(=O)—NH$_2$; —C(=O)—NH—R$^{30}$; —C(=O)—NR$^{31}$R$^{32}$; —S(=O)—R$^{33}$; —S(=O)$_2$—R$^{34}$; C$_{1-6}$-alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-7}$-cycloalkyl, C$_{5-6}$-cycloalkenyl, 5- to 7-membered heterocycloalkyl or 5- to 7-membered heterocycloalkenyl, which in each case can be bound via a C$_{1-3}$-alkylene, C$_{2-3}$-alkenylene or C$_{2-3}$-alkynylene group or is unsubstituted or is substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denotes a residue selected from the group consisting of phenyl, naphthyl, anthracenyl, thienyl, furyl, pyridinyl, thiazolyl, thiadiazolyl, oxazolyl, oxadiazolyl and isoxazolyl, which in each case can be bound via a C$_{1-3}$-alkylene, C$_{2-3}$-alkenylene or C$_{2-3}$-alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$;

and $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$, mutually independently, in each case denote C$_{1-6}$-alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-7}$-cycloalkyl, C$_{5-6}$-cycloalkenyl, 5- to 7-membered heterocycloalkyl or 5- to 7-membered heterocycloalkenyl, which can in each case be bound via a C$_{1-3}$-alkylene, C$_{2-3}$-alkenylene or C$_{2-3}$-alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denote a residue selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, chinolinyl, isochinolinyl and chinazolinyl, which in each case can be bound via a C$_{1-3}$-alkylene, C$_{2-3}$-alkenylene or C$_{2-3}$-alkynylene group or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF₃, —S—CF₃, —SH, —NH—S(=O)₂—CH₃, —C(=O)—OH, —C(=O)—CH₃, —C(=O)—C₂H₅, —C(=O)—N(CH₃)₂, —C(=O)—NH—CH₃, —NH—C(=O)—CH₃, —NH—C(=O)—C₂H₅, —C(=O)—O—CH₃ and —C(=O)—O—C₂H₅;

in each case optionally in the form of one of the pure stereoisomers thereof, in the form of one of the racemates thereof or in the form of a mixture of stereoisomers in any mixing ratio, or in each case in the form of a corresponding salt.

18. A compound according to claim 1, wherein a, b and c, mutually independently, in each case denote 0 or 1, wherein the sum of a, b and c is equal to 1, 2 or 3;

A denotes a residue selected from the group consisting of

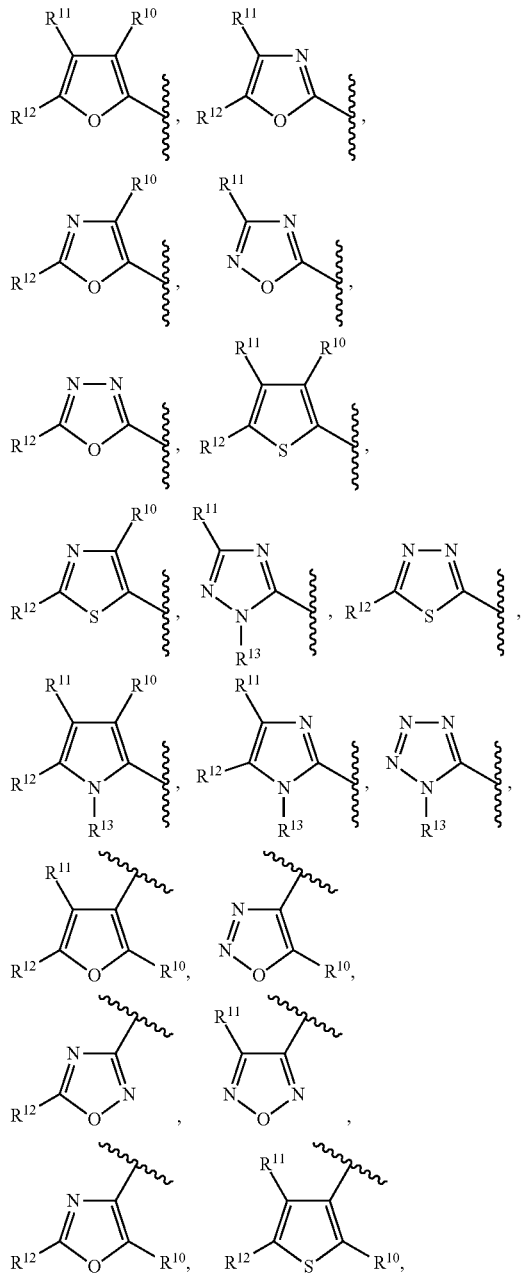

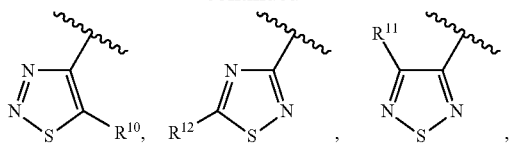

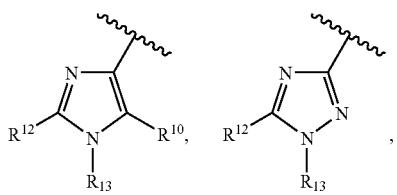

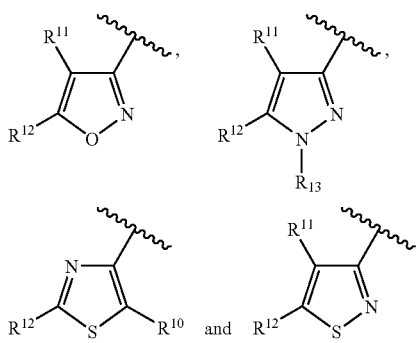

R¹ and R⁸, mutually independently, in each case denote H; —C(=O)—R²⁸; —C(=O)—O—R²⁹; S(=O)—R³³; —S(=O)₂—R³⁴; an alkyl residue selected from the group consisting of methyl, ethyl, n-propyl, isopropyl, n-butyl, 2-butyl, isobutyl, tert-butyl, n-pentyl and n-hexyl; a cycloalkyl residue selected from the group consisting of cyclopropyl, cyclobutyl, cyclopentyl and cyclohexyl; or a benzyl or phenethyl residue, which is unsubstituted or is substituted with 1, 2, 3, 4 or 5 substituents mutually independently selected from the group consisting of F, Cl, Br, methyl, ethyl, n-propyl, isopropyl, n-butyl, 2-butyl, isobutyl, tert-butyl, —OH, —O—CH₃, —O—C₂H₅ and —O—C₃H₇;

R², R³, R⁴, R⁵, R⁶, R⁷, R¹⁴, R¹⁵, R¹⁶, R¹⁷, R¹⁸, R¹⁹, R²⁰, R²¹, R²², R²³, R²⁴, R²⁵, R²⁶ and R²⁷, mutually independently, in each case denote H; F; Cl; Br; I; —NH₂; —OH; —SH; —CN; —NO₂; —CF₃; —NH—R³⁵; —NR³⁶R³⁷; —O—R⁴²; —S—R⁴³; an alkyl residue selected from the group consisting of methyl, ethyl, n-propyl, isopropyl, n-butyl, 2-butyl, isobutyl, tert-butyl, n-pentyl and n-hexyl; or a residue selected from the group consisting of cyclopropyl, cyclobutyl, cyclopentyl and cyclohexyl;

or R² and R³ or R⁴ and R⁵ or R⁶ and R⁷ or R¹⁴ and R¹⁵ or R¹⁶ and R¹⁷ or R¹⁸ and R¹⁹ or R²⁰ and R²¹ or R²² and R²³ or R²⁴ and R²⁵ or R²⁶ and R²⁷, mutually independently, jointly in each case denote a residue selected from the group consisting of an oxo group (=O) and a thioxo group (=S);

or R¹ and R⁸ together with the —N—CR²R³—(CR⁴R⁵)ᵦ—(CR⁶R⁷)ᵧ group joining them together form a residue selected from the group consisting of

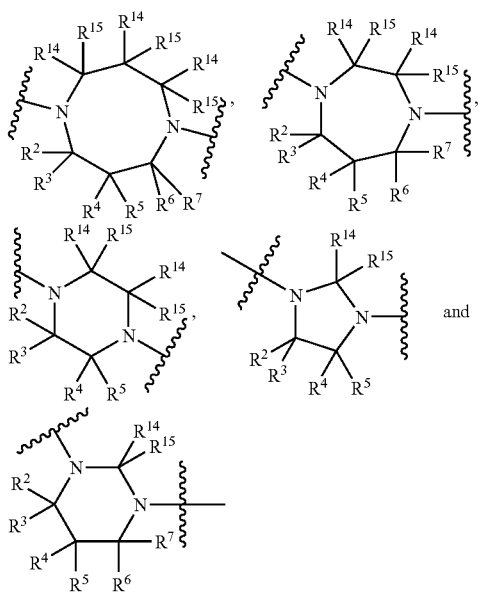

or R¹ and R² together with the —N—CR³ group joining them together form a residue selected from the group consisting of

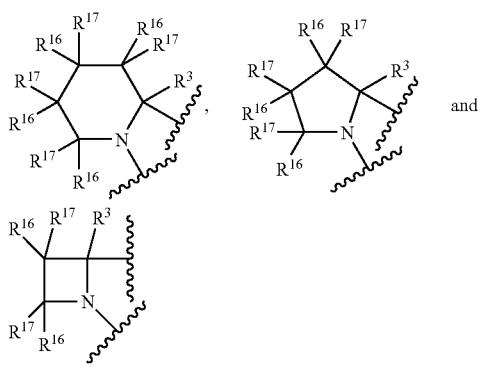

wherein, in this case, b denotes 1 and c denotes 0;
or R¹ and R⁴ together with the —N—CR²R³—CR⁵ group joining them together form a residue selected from the group consisting of

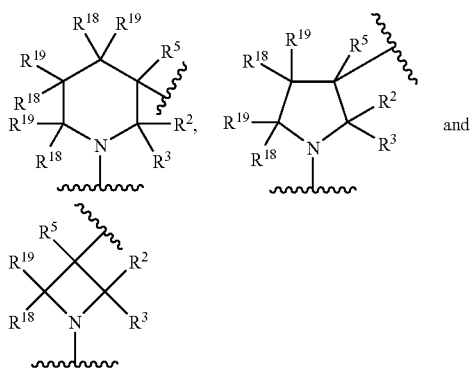

wherein, in this case, c denotes 0;

R¹ and R⁶ together with the —N—CR²R³—CR⁴R⁵—CR⁷ group joining them together form a residue selected from the group consisting of

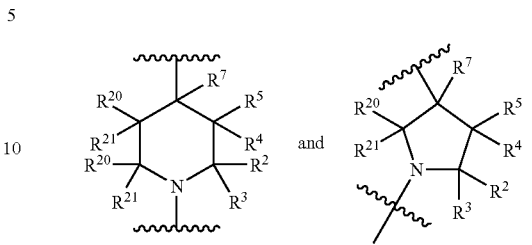

or R⁶ and R⁸ together with the —N—CR⁷ group joining them together form a residue selected from the group consisting of

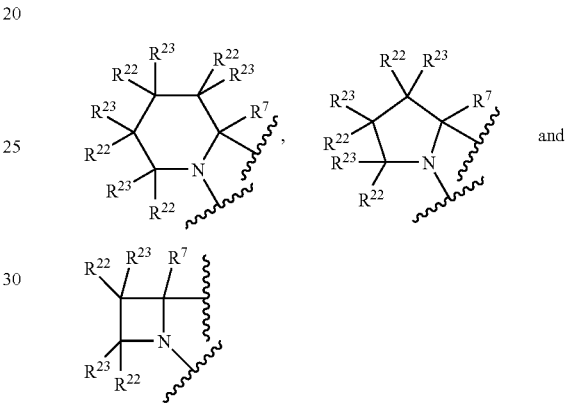

wherein, in this case, b denotes 1 and a denotes 0;
or R⁴ and R⁸ together with the —N—CR⁶R⁷—CR⁵ group joining them together form a residue selected from the group consisting of

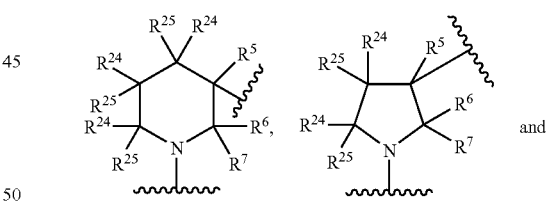

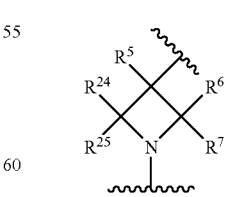

wherein, in this case, a denotes 0;
or R² and R⁸ together with the —N—CR⁶R⁷—CR⁴R⁵—CR³ group joining them together form a residue selected from the group consisting of

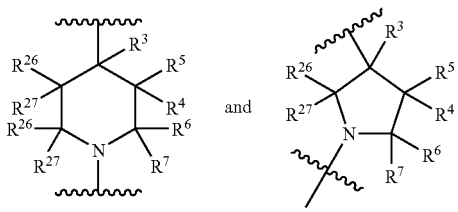

R[9] denotes a residue selected from the group consisting of phenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl and imidazolyl, which in each case is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, cyclopropyl, cyclobutyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

R[10], R[11] and R[12], mutually independently, in each case denote H; F; Cl; Br; I; —CF$_3$; —NO$_2$; —CN; —C(=O)—OH; —C(=O)—O—R[29]; —C(=O)—NH$_2$; —C(=O)—NH—R[30]; —C(=O)—NR[31]R[32]; —S(=O)—R[33]; —S(=O)$_2$—R[34]; —O—R[42]; —S—R[43]; an alkyl residue selected from the group consisting of methyl, ethyl, n-propyl, isopropyl, n-butyl, 2-butyl, isobutyl and tert-butyl; a residue selected from the group consisting of ethenyl, ethynyl, allyl and propynyl; a residue selected from the group consisting of cyclopropyl, cyclobutyl and cyclopentyl; or a residue selected from the group consisting of phenyl, benzyl, phenethyl, oxadiazolyl, 2-pyridyl, 3-pyridyl, 4-pyridyl, 2-thienyl, 3-thienyl, 2-furyl and 3-furyl, which in each case is unsubstituted or substituted with optionally 1, 2, 3, 4 or 5 substituents mutually independently selected from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

R[13] denotes H; —C(=O)—R[28]; —C(=O)—H; —C(=O)—O—R[29]; —S(=O)—R[33]; —S(=O)$_2$—R[34]; an alkyl residue selected from the group consisting of methyl, ethyl, n-propyl, isopropyl, n-butyl, 2-butyl, isobutyl and tert-butyl; a residue selected from the group consisting of cyclopropyl, cyclobutyl, cyclopentyl and cyclohexyl; or a residue selected from the group consisting of phenyl, benzyl, phenethyl, oxadiazolyl, 2-pyridyl, 3-pyridyl, 4-pyridyl, 2-thienyl, 3-thienyl, 2-furyl and 3-furyl, which in each case can be bound via a C$_{1-3}$-alkylene group or is unsubstituted or substituted with optionally 1, 2, 3, 4 or 5 substituents mutually independently selected from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

and R[28], R[29], R[30], R[31], R[32], R[33], R[34], R[35], R[36], R[37], R[42] and R[43], mutually independently, in each case denote an alkyl residue selected from the group consisting of methyl, ethyl, n-propyl, isopropyl, n-butyl, 2-butyl, isobutyl, tert-butyl, n-pentyl and n-hexyl; —CF$_3$; —C$_2$F$_5$; —CH$_2$—CF$_3$; or a phenyl, benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

in each case optionally in the form of one of the pure stereoisomers thereof, in the form of one of the racemates thereof or in the form of a mixture of stereoisomers in any mixing ratio, or in each case in the form of a corresponding salt.

19. A compound according to claim 1, wherein a, b and c, mutually independently, in each case denote 0 or 1, wherein the sum of a, b and c is equal to 1, 2 or 3;

A denotes a residue selected from the group consisting of

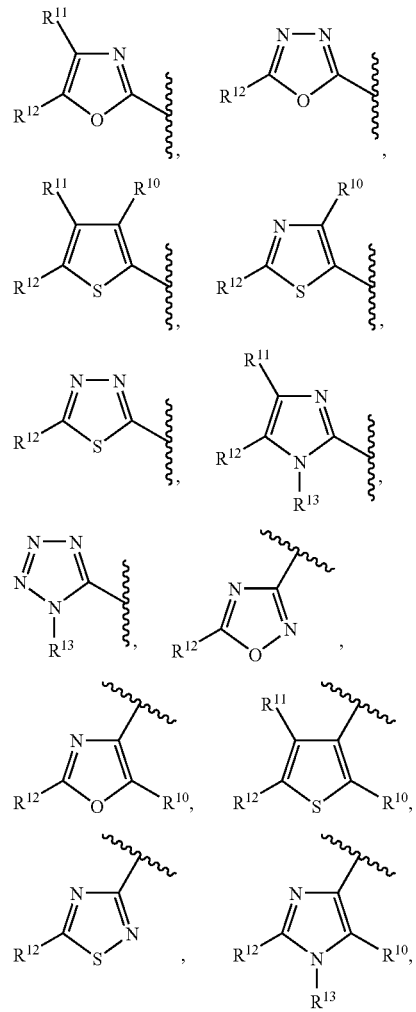

-continued

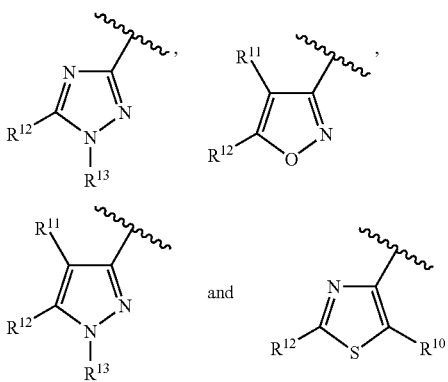

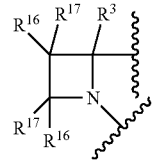

-continued wherein, in this case, b denotes 1 and c denotes 0;

or R¹ and R⁴ together with the —N—CR²R³—CR⁵ group joining them together form a residue selected from the group consisting of R¹ and R⁸, mutually independently, in each case denote H; —C(=O)—R²⁸; —C(=O)—O—R²⁹; an alkyl residue selected from the group consisting of methyl, ethyl, n-propyl, isopropyl, n-butyl, 2-butyl, isobutyl, tert-butyl, n-pentyl and n-hexyl; or a cyclopropyl residue;

R², R³, R⁴, R⁵, R⁶, R⁷, R¹⁴, R¹⁵, R¹⁶, R¹⁷, R¹⁸, R¹⁹, R²², R²³, R²⁴ and R²⁵, mutually independently, in each case denote H; F; Cl; Br; I; —NH₂; —OH; —SH; —CN; —NO₂; —CF₃; —NH—R³⁵; —NR³⁶R³⁷; —O—R⁴²; —S—R⁴³; an alkyl residue selected from the group consisting of methyl, ethyl, n-propyl, isopropyl, n-butyl, 2-butyl, isobutyl, tert-butyl, n-pentyl and n-hexyl; or a cyclopropyl residue;

or R¹ and R⁸ together with the —N—CR²R³—(CR⁴R⁵)ᵦ—(CR⁶R⁷)ᶜ group joining them together form a residue selected from the group consisting of

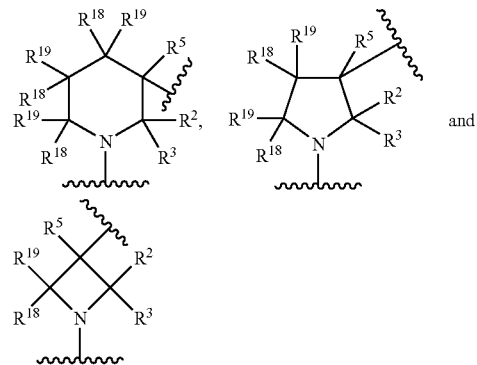

wherein, in this case, c denotes 0;

or R⁶ and R⁸ together with the —N—CR⁷ group joining them together form a residue selected from the group consisting of

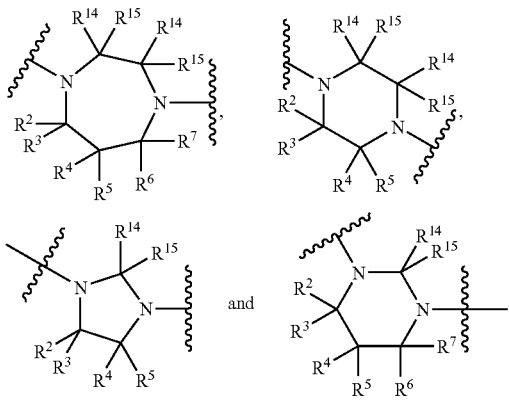

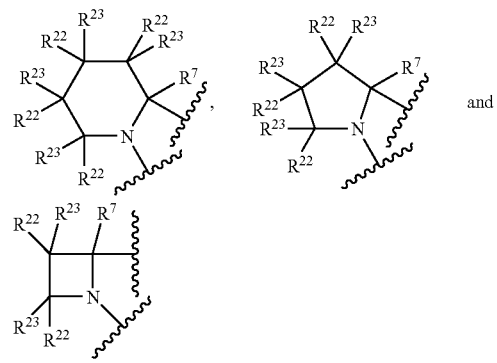

or R¹ and R² together with the —N—CR³ group joining them together form a residue selected from the group consisting of wherein, in this case, b denotes 1 and a denotes 0;

or R⁴ and R⁸ together with the —N—CR⁶R⁷—CR⁵ group joining them together form a residue selected from the group consisting of

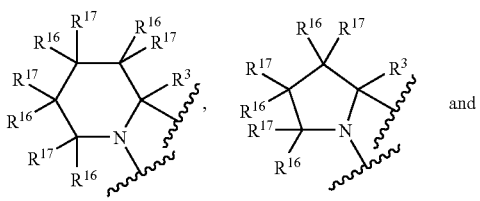

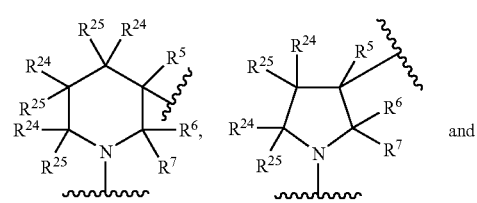

-continued

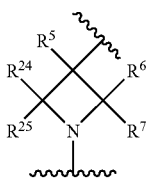

wherein, in this case, a denotes 0;

R$^9$ denotes a residue selected from the group consisting of phenyl, thienyl, pyrazolyl, pyrazinyl, pyridazinyl, pyrimidinyl, pyridinyl, thiazolyl and thiadiazolyl, which in each case is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, cyclopropyl, cyclobutyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

R$^{10}$, R$^{11}$ and R$^{12}$, mutually independently, in each case denote H; F; Cl; Br; I; —CF$_3$; —NO$_2$; —CN; —C(=O)—OH; —C(=O)—O—R$^{29}$; —C(=O)—NH$_2$; —O—R$^{42}$; —S—R$^{43}$; ethenyl; ethynyl; cyclopropyl or an alkyl residue selected from the group consisting of methyl, ethyl, n-propyl, isopropyl, n-butyl, 2-butyl, isobutyl and tert-butyl;

R$^{13}$ denotes H; —C(=O)—R$^{28}$; —C(=O)—H; —C(=O)—O—R$^{29}$; —S(=O)—R$^{33}$; —S(=O)$_2$—R$^{34}$; cyclopropyl; cyclobutyl; or an alkyl residue selected from the group consisting of methyl, ethyl, n-propyl, isopropyl, n-butyl, 2-butyl, isobutyl and tert-butyl;

and R$^{28}$, R$^{29}$, R$^{33}$, R$^{34}$, R$^{35}$, R$^{36}$, R$^{37}$, R$^{42}$ and R$^{43}$, mutually independently, in each case denote an alkyl residue selected from the group consisting of methyl, ethyl, n-propyl, isopropyl, n-butyl, 2-butyl, isobutyl, tert-butyl, n-pentyl and n-hexyl; —CF$_3$; —C$_2$F$_5$; —CH$_2$—CF$_3$; or a phenyl, benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

in each case optionally in the form of one of the pure stereoisomers thereof, in the form of one of the racemates thereof or in the form of a mixture of stereoisomers in any desired ratio, or in each case in the form of a corresponding salt.

20. A compound according to claim 1, wherein a, b and c, mutually independently, in each case denote 0 or 1, wherein the sum of a, b and c is equal to 1 or 2;

A denotes a residue selected from the group consisting of

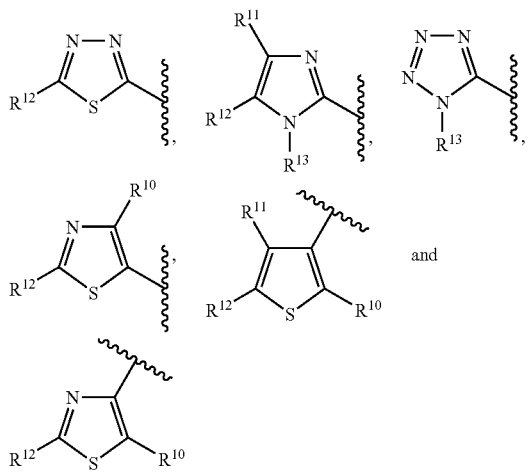

R$^1$ and R$^8$, mutually independently, in each case denote H; —C(=O)—R$^{28}$; an alkyl residue selected from the group consisting of methyl, ethyl, n-propyl, isopropyl, n-butyl, 2-butyl, isobutyl, tert-butyl, n-pentyl and n-hexyl; or a cyclopropyl residue;

R$^2$, R$^3$, R$^4$, R$^5$, R$^6$, R$^7$, R$^{14}$, R$^{15}$, R$^{16}$, R$^{17}$, R$^{22}$, R$^{23}$, R$^{24}$ and R$^{25}$, mutually independently, in each case denote H; F; Cl; Br; I; —CN; —NO$_2$; —CF$_3$; —O—R$^{42}$; an alkyl residue selected from the group consisting of methyl, ethyl, n-propyl, isopropyl, n-butyl, 2-butyl, isobutyl, tert-butyl, n-pentyl and n-hexyl; or a cyclopropyl residue;

or R$^1$ and R$^8$ together with the —N—CR$^2$R$^3$—CR$^4$R$^5$ group joining them together form the following residue

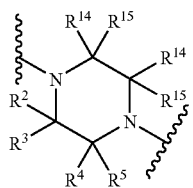

or R$^1$ and R$^2$ together with the —N—CR$^3$ group joining them together form a residue selected from the group consisting of

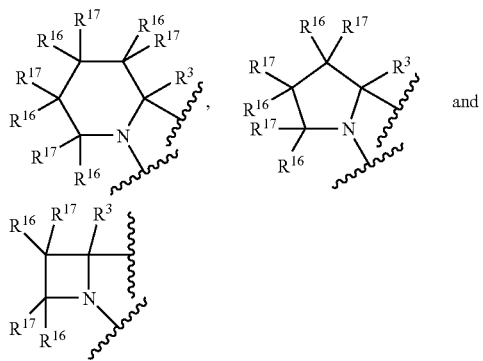

wherein, in this case, b denotes 1 and c denotes 0;

or $R^6$ and $R^8$ together with the —N—$CR^7$ group joining them together form a residue selected from the group consisting of

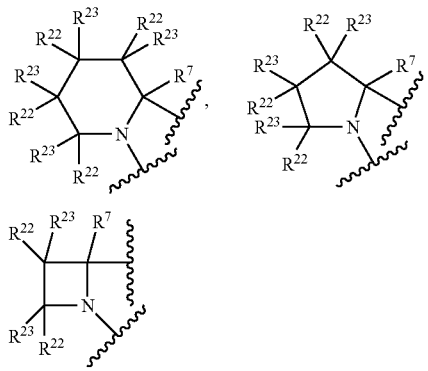

wherein, in this case, b denotes 1 and a denotes 0;

$R^9$ denotes a residue selected from the group consisting of phenyl and thienyl, which in each case is unsubstituted or substituted with 1 or 2 substituents mutually independently selected from the group consisting of F, Cl, Br, I, —CN, methyl, ethyl, n-propyl, isopropyl, n-butyl, 2-butyl, isobutyl, tert-butyl, ethenyl, ethynyl, cyclopropyl, —O—$CH_3$, —O—$C_2H_5$, —O—$C_3H_7$, —$NO_2$, —$CF_3$ and —O—$CF_3$;

$R^{10}$, $R^{11}$ and $R^{12}$, mutually independently, in each case denote H; F; Cl; Br; —$CF_3$; —$NO_2$; —CN; —O—$R^{42}$; an alkyl residue selected from the group consisting of methyl, ethyl, n-propyl, isopropyl, isobutyl and tert-butyl; ethenyl; ethynyl or cyclopropyl; $R^{13}$ denotes H; —C(=O)—H; —C(=O)—$R^{28}$; cyclopropyl; or an alkyl residue selected from the group consisting of methyl, ethyl, n-propyl, isopropyl, n-butyl, 2-butyl, isobutyl and tert-butyl;

and $R^{28}$ and $R^{42}$, mutually independently, in each case denote an alkyl residue selected from the group consisting of methyl, ethyl, n-propyl, isopropyl, n-butyl, 2-butyl, isobutyl and tert-butyl; or —$CF_3$;

in each case optionally in the form of one of the pure stereoisomers thereof, in the form of one of the racemates thereof or in the form of a mixture of stereoisomers in any mixing ratio, or in each case in the form of a corresponding salt.

21. A compound according to claim 1, wherein a, b and c, mutually independently, in each case denote 0 or 1, wherein the sum of a, b and c is equal to 2;

A denotes a residue selected from the group consisting of

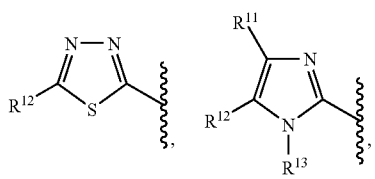

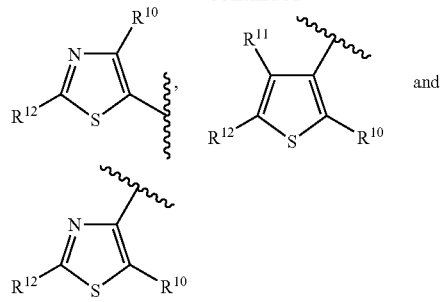

$R^1$ and $R^8$, mutually independently, in each case denote H, —C(=O)—$CH_3$, methyl, isopropyl or cyclopropyl;

$R^2$, $R^3$, $R^4$, $R^5$, $R^6$, $R^7$, $R^{14}$, $R^{15}$, $R^{16}$, $R^{17}$, $R^{22}$ and $R^{23}$, mutually independently, in each case denote H or an alkyl residue selected from the group consisting of methyl, ethyl, n-propyl, isopropyl, n-butyl, 2-butyl, isobutyl, tert-butyl, n-pentyl and n-hexyl;

or $R^1$ and $R^8$ together with the —N—$CR^2R^3$—$CR^4R^5$ group joining them together form the following residue

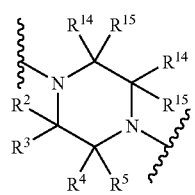

or $R^1$ and $R^2$ together with the —N—$CR^3$ group joining them together form the following residue

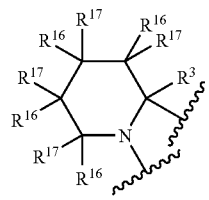

wherein, in this case, b denotes 1 and c denotes 0;

or $R^6$ and $R^8$ together with the —N—$CR^7$ group joining them together form the following residue

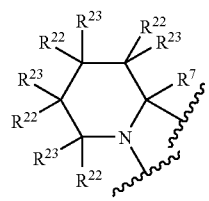

wherein, in this case, b denotes 1 and a denotes 0;

$R^9$ denotes a phenyl residue which in each case is unsubstituted or substituted with 1 or 2 substituents mutually independently selected from the group consisting of F, Cl, Br, I, —CN, methyl, ethyl, n-propyl, isopropyl, n-butyl, 2-butyl, isobutyl, tert-butyl, ethenyl, ethynyl, cyclopropyl, —O—$CH_3$, —O—$C_2H_5$, —O—$C_3H_7$, —$NO_2$, —$CF_3$ and —O—$CF_3$;

$R^{10}$, $R^{11}$ and $R^{12}$, mutually independently, in each case denote H; F; Cl; Br; —$CF_3$; —$NO_2$; —CN; —O—$R^{42}$; an alkyl residue selected from the group consisting of methyl, ethyl, n-propyl, isopropyl, isobutyl and tert-butyl; ethenyl; ethynyl or cyclopropyl;

and $R^{13}$ denotes H or an alkyl residue selected from the group consisting of methyl, ethyl, n-propyl, isopropyl, n-butyl, 2-butyl, isobutyl and tert-butyl;

in each case optionally in the form of one of the pure stereoisomers thereof, in the form of one of the racemates thereof or in the form of a mixture of stereoisomers in any mixing ratio, or in each case in the form of a corresponding salt.

22. A compound according to claim 1, wherein
a, b and c, mutually independently, in each case denote 0 or 1, wherein the sum of a, b and c is equal to 2;
A denotes a residue selected from the group consisting of

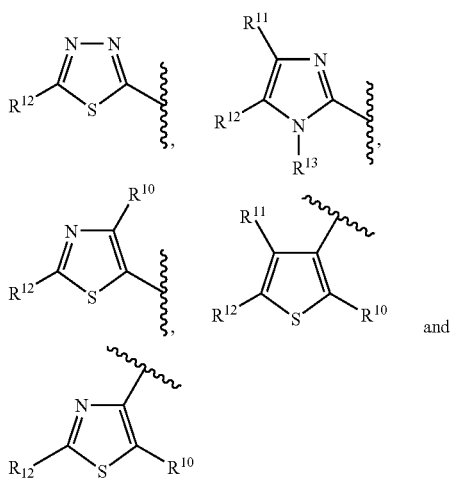

$R^1$ and $R^8$, mutually independently, in each case denote H, methyl or isopropyl;

$R^2$, $R^3$, $R^4$, $R^5$, $R^6$, $R^7$, $R^{14}$ and $R^{15}$, mutually independently, in each case denote H or an alkyl residue selected from the group consisting of methyl and ethyl;

or $R^1$ and $R^8$ together with the —N—$CR^2R^3$—$CR^4R^5$ group joining them together form the following residue

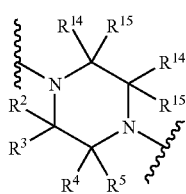

$R^9$ denotes a phenyl residue which in each case is unsubstituted or substituted with 1 or 2 substituents mutually independently selected from the group consisting of F, Cl, Br, I and —CN;

$R^{10}$, $R^{11}$ and $R^{12}$, mutually independently, in each case denote H; or an alkyl residue selected from the group consisting of methyl, ethyl, n-propyl, isopropyl, isobutyl and tert-butyl;

and $R^{13}$ denotes H or an alkyl residue selected from the group consisting of methyl, ethyl, n-propyl, isopropyl, n-butyl, 2-butyl, isobutyl and tert-butyl;

in each case optionally in the form of one of the pure stereoisomers thereof, in the form of one of the racemates thereof or in the form of a mixture of stereoisomersin any mixing ratio, or in each case in the form of a corresponding salt.

23. A compound according to claim 1 selected from the group consisting of

[1] 1-(3-phenyl-propiolyl)-4-(thiophen-3-yl)-piperazine,

[2] 1-(3-phenyl-propiolyl)-4-(thiazol-4-yl)-piperazine,

[3] 1-(3-phenyl-propiolyl)-4-(1-methyl-imidazol-2-yl)-piperazine,

[4] (R)-2-methyl-1-(3-(3-chloro-phenyl)-propiolyl)-4-(thiazol-4-yl)-piperazine,

[5] 2-methyl-1-(3-(3-chloro-phenyl)-propiolyl)-4-(1,3,4-thiadiazol-2-yl)-piperazine,

[6] 3-(3-chlorophenyl)-N-(2-(methyl(1,3,4-thiadiazol-2-yl)amino)ethyl)propiolamide,

[7] 3-(3-chlorophenyl)-N-(2-(methyl(thiazol-5-yl)amino)ethyl)propiolamide and

[8] 3-(3-chlorophenyl)-N-(2-(methyl(1-methyl-1H-imidazol-2-yl)amino)ethyl)-propiolamide;

in each case optionally in the form of one of the pure stereoisomers thereof, in the form of one of the racemates thereof or in the form of a mixture of stereoisomersin any mixing ratio, or in each case in the form of a corresponding salt.

24. A method for producing compounds of the formula I according to claim 1, said method comprising: transferring at least one compound of the formula II,

A-X, in which A has the meaning according to claim 1 and X denotes a leaving group, with at least one compound of the formula III,

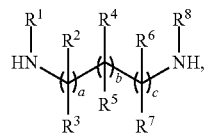

III in which a, b, c, $R^1$, $R^2$, $R^3$, $R^4$, $R^5$, $R^6$, $R^7$ and $R^8$ have the meaning according to claim 1, optionally in a reaction medium, optionally in the presence of at least one base, or at least one metallo-organic compound or at least one metal hydride reagent, or a mixture thereof, or in the presence of at least one copper salt, and optionally in the presence of at least one metal, into at least one corresponding compound of the formula IV, optionally in the form of a corresponding salt,

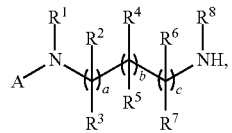

IV in which a, b, c, A, $R^1$, $R^2$, $R^3$, $R^4$, $R^5$, $R^6$, $R^7$ and $R^8$ have the above-mentioned meaning, and this is optionally purified or isolated or both;

or transferring at least one compound of the formula II with at least one compound of the formula V,

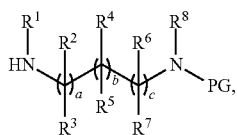

V in which a, b, c, $R^1$, $R^2$, $R^3$, $R^4$, $R^5$, $R^6$, $R^7$ and $R^8$ have the meaning according to claim 1 and PG denotes a protective group, optionally in a reaction medium, optionally in the presence of at least one base, or at least one metallo-organic compound or at least one metal hydride reagent, or a mixture thereof, or in the presence of at least one copper salt and optionally in the presence of at least one metal, or in the presence of at least one catalyst, optionally in the presence of at least one ligand, optionally in the presence of at least one organic or inorganic base selected from the group consisting of potassium-tert-butoxide, sodium-tert-butoxide, tri-potassium phosphate, caesium carbonate, lithiumbis(trimethylsilyl)amide, sodiumbis(trimethylsilyl)amide and potassiumbis(trimethylsilyl)amide, into at least one compound of the formula VI,

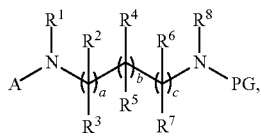

VI in which a, b, c, A, $R^1$, $R^2$, $R^3$, $R^4$, $R^5$, $R^6$, $R^7$, $R^8$ and PG have the above-mentioned meaning, and this is optionally purified or isolated or both;
or transferring at least one compound of the formula VII,

VII in which $R^1$ and A have the meaning according to claims 1, with at least one compound of the formula VIII,

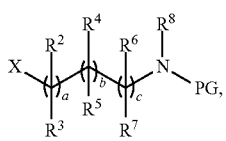

VIII in which a, b, c, $R^2$, $R^3$, $R^4$, $R^5$, $R^6$, $R^7$, $R^8$ and PG have the above-mentioned meaning and X denotes a leaving group, optionally in a reaction medium, optionally in the presence of at least one base, or optionally in the presence of at least one metallo-organic compound, or optionally in the presence of at least one metal hydride compound, into at least one corresponding compound of the formula VI and this is optionally purified or isolated or both;
and transferring at least one compound of the formula VI, in the event that PG denotes a tert-butoxycarbonyl- or 9-fluorenylmethyloxycarbonyl group, in a reaction medium, in the presence of at least one acid, or, in the event that PG denotes a benzyl group or benzyloxycarbonyl group, in a reaction medium, in the presence of hydrogen and in the presence of at least one catalyst, into at least one corresponding compound of the formula IV, optionally in the form of a corresponding salt, and this is optionally purified or isolated or both;
and transferring at least one compound of the formula IV into at least one corresponding compound of the formula I, optionally in the form of a corresponding salt by conversion with at least one compound of the formula $R^9$—C≡C—C(=O)—OH, in which $R^9$ has the meaning according to claim 1, in a reaction medium, optionally in the presence of at least one suitable coupling agent, optionally in the presence of at least one base, or by conversion with at least one compound of the formula $R^9$—C≡C—C(=O)—X, in which $R^9$ has the above-mentioned meaning and X denotes a leaving group, in a reaction medium, optionally in the presence of at least one base,

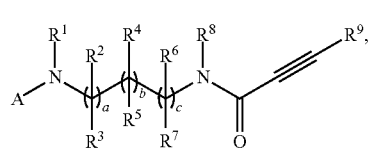

I in which a, b, c, A, $R^1$, $R^2$, $R^3$, $R^4$, $R^5$, $R^6$, $R^7$, $R^8$ and $R^9$ have the above-mentioned meaning, and this is optionally purified or isolated or both;
or transferring at least one compound of the formula IV into at least one corresponding compound of the formula IX, optionally in the form of a corresponding salt by conversion with propionic acid [HC≡C—C(=O)—OH] in a reaction medium, optionally in the presence of at least one suitable coupling agent, optionally in the presence of at least one base, or by conversion with at least one compound of the formula HC≡C—C(=O)—X, in which X denotes a leaving group, in a reaction medium, optionally in the presence of at least one base,

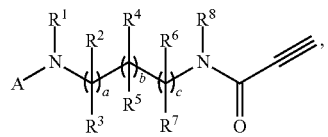

IX in which a, b, c, A, $R^1$, $R^2$, $R^3$, $R^4$, $R^5$, $R^6$, $R^7$ and $R^8$ have the above-mentioned meaning, and this is optionally purified or isolated or both,
and transferring at least one compound of the formula IX into at least one corresponding compound of the formula I, optionally in the form of a corresponding salt by conversion with at least one compound of the formula $R^9$—X, in which $R^9$ has the meaning according to claim 1 and X denotes a leaving group, in a reaction medium, optionally in the presence of at least one catalyst, optionally in the presence of at least one ligand, optionally in the presence of at least one inorganic salt, optionally in the presence of at least one copper salt, optionally in the presence of at least one organic or inorganic base, and this is optionally purified or isolated or both.

25. A method for producing compounds of the formula I according to claim 1, said method comprising: transferring by conversion at least one compound of the formula III,

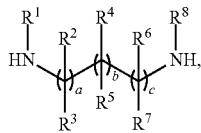

in which a, b, c, $R^1$, $R^2$, $R^3$, $R^4$, $R^5$, $R^6$, $R^7$ and $R^8$ have the meaning according to claim 1,
with at least one compound of the formula $R^9$—C≡C—C(=O)—OH, in which $R^9$ has the meaning according to claim 1, in a reaction medium, optionally in the presence of at least one suitable coupling agent, optionally in the presence of at least one base, or with at least one compound of the formula $R^9$—C≡C—C(=O)—X, in which $R^9$ has the above-mentioned meaning and X denotes a leaving group, in a reaction medium, optionally in the presence of at least one base, into at least one corresponding compound of the formula XI, optionally in the form of a corresponding salt,

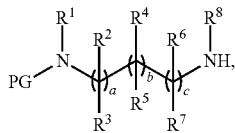

in which a, b, c, $R^1$, $R^2$, $R^3$, $R^4$, $R^5$, $R^6$, $R^7$, $R^8$ and $R^9$ have the above-mentioned meaning, and this is optionally purified or isolated or both;
or by transferring by conversion at least one compound of the formula V,

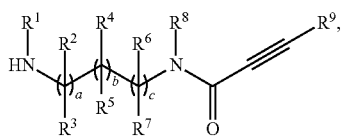

in which a, b, c, $R^1$, $R^2$, $R^3$, $R^4$, $R^5$, $R^6$, $R^7$ and $R^8$ have the meaning according to claim 1 and PG denotes a protective group,
with at least one compound of the formula $R^9$—C≡C—C(=O)—OH, in which $R^9$ has the meaning according to f claim 1, in a reaction medium, optionally in the presence of at least one suitable coupling agent, optionally in the presence of at least one base, or with at least one compound of the formula $R^9$—C≡C—C(=O)—X, in which $R^9$ has the above-mentioned meaning and X denotes a leaving group, in a reaction medium, optionally in the presence of at least one base, into at least one corresponding compound of the formula XII, optionally in the form of a corresponding salt,

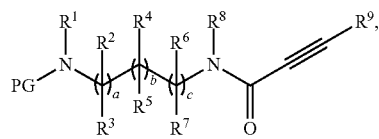

in which a, b, c, $R^1$, $R^2$, $R^3$, $R^4$, $R^5$, $R^6$, $R^7$, $R^8$, $R^9$ and PG have the above-mentioned meaning, and this is optionally purified or isolated or both;
and transferring at least one compound of the formula XII, in the event that PG denotes a tert-butoxycarbonyl or 9-fluorenylmethyloxycarbonyl group, into at least one corresponding compound of the formula XI, optionally in the form of a corresponding salt, in a reaction medium, in the presence of at least one acid, or, in the event that PG denotes a benzyl or benzyloxycarbonyl group, in a reaction medium, in the presence of hydrogen and in the presence of at least one catalyst, and this is optionally purified or isolated or both; and transferring at least one compound of the formula XI into at least one corresponding compound of the formula I, optionally in the form of a corresponding salt by conversion with at least one compound of the formula II,

A-X, in which residue A has the meaning according to claim 1 and X denotes a leaving group, in a reaction medium, optionally in the presence of at least one base, /or at least one metallo-organic compound or at least one metal hydride reagent or a mixture thereof, or in the presence of at least one copper salt, and optionally in the presence of at least one metal, or in the presence of at least one catalyst, optionally in the presence of at least one ligand,

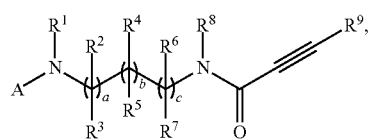

in which a, b, c, A, $R^1$, $R^2$, $R^3$, $R^4$, $R^5$, $R^6$, $R^7$, $R^8$ and $R^9$ have the above-mentioned meaning, and this is optionally purified or isolated or both.

26. A pharmaceutical composition comprising: at least one compound according to claim 1 and optionally one or more physiologically acceptable auxiliary substances.

27. A method for the treatment of disorders or illnesses, which are at least partially mediated by mGluR5 receptors comprising:
administering an effective amount of at least one compound according to claim 1 to a patient in need thereof wherein the disorders or illnesses are selected from the group consisting of pain; migraine; depression; Alzheimer's disease; Parkinson's disease; anxiety states; panic attacks; coughing; urinary incontinence; diarrhoea; pruritis; schizophrenia; cerebral ischaemia; asthma; regurgitation (vomiting); stroke; dyskinesia; retinopathy; listlessness; laryngitis; disorders of food intake; dependency on alcohol; dependency on medicines; alcohol abuse; drug abuse; withdrawal symptoms associated with dependency on alcohol, nicotine, and/or cocaine; stomach-esophagus-reflux syndrome; gastroesophageal reflux; irritable bowel syndrome; diuresis; antinatriuresis; reduced vigilance; and reduced libido.

28. The method according to claim 27, wherein the disorders or illnesses are selected from the group consisting of pain selected from the group consisting of acute pain, chronic pain, neuropathic pain and visceral pain; anxiety states; panic attacks; dependency on alcohol; dependency on medicines; Attention Deficit Disorder (ADD); disorders of food intake selected from the group consisting of bulimia, cachexia, anorexia and obesity; dependency on nicotine and/or cocaine; alcohol abuse; abuse of medication; nicotine and/or cocaine abuse; withdrawal symptoms associated with dependency on alcohol, medications or nicotine and/or cocaine; development of tolerance to to natural or synthetic opioids; stomach-esophagus-reflux-syndrome; gastroesophagal reflux and irritable bowel syndrome.

29. The method according to claim 27, wherein the disorder or illness is pain selected from the group consisting of acute pain, chronic pain, neuropathic pain and visceral pain.

30. The method according to claim 27, wherein the disorder or illness is selected from the group consisting of anxiety states and panic attacks.

31. A method of providing local anaesthesia to a patient in need thereof, said method comprising locally administering to said patient at least one compound according to claim 1.

* * * * *